(12) United States Patent
Shin et al.

(10) Patent No.: US 8,686,406 B2
(45) Date of Patent: Apr. 1, 2014

(54) PYRENE-BASED COMPOUND, ORGANIC LIGHT-EMITTING DIODE COMPRISING THE SAME AND ORGANIC LIGHT-EMITTING APPARATUS COMPRISING THE SAME

(75) Inventors: Dong-Woo Shin, Yongin (KR); O-Hyun Kwon, Yongin (KR); Kyul Han, Yongin (KR); Seul-Ong Kim, Yongin (KR); Byoung-Ki Choi, Yongin (KR)

(73) Assignee: Samsung Display Co., Ltd., Yongin-si (KR)

( * ) Notice: Subject to any disclaimer, the term of this patent is extended or adjusted under 35 U.S.C. 154(b) by 75 days.

(21) Appl. No.: 13/538,690

(22) Filed: Jun. 29, 2012

(65) Prior Publication Data

US 2013/0228752 A1 Sep. 5, 2013

(30) Foreign Application Priority Data

Mar. 2, 2012 (KR) .................. 10-2012-0022036

(51) Int. Cl.
*H01L 21/02* (2006.01)

(52) U.S. Cl.
USPC ...... 257/40; 257/103; 257/E51.024; 428/690; 428/917

(58) Field of Classification Search
USPC ............ 257/40, 103, E51.024; 428/690, 917
See application file for complete search history.

(56) References Cited

U.S. PATENT DOCUMENTS

| | | | |
|---|---|---|---|
| 5,153,073 A | | 10/1992 | Ohnuma et al. |
| 6,852,429 B1* | | 2/2005 | Li et al. .................... 428/690 |
| 7,244,516 B1* | | 7/2007 | Sakamoto et al. ........... 428/690 |
| 2011/0006669 A1 | | 1/2011 | Lee et al. |
| 2011/0156011 A1 | | 6/2011 | Bin et al. |
| 2011/0204354 A1* | | 8/2011 | Sekiguchi et al. ............. 257/40 |
| 2012/0116050 A1* | | 5/2012 | Muellen et al. .............. 528/396 |
| 2012/0228583 A1* | | 9/2012 | Wu et al. ..................... 257/40 |
| 2012/0292605 A1* | | 11/2012 | Park et al. .................... 257/40 |
| 2013/0234118 A1* | | 9/2013 | Kwon et al. .................. 257/40 |

FOREIGN PATENT DOCUMENTS

| | | |
|---|---|---|
| KR | 10-2011-0005516 | 1/2011 |
| KR | 10-2011-0076018 | 7/2011 |
| KR | 10-2011-0081698 | 7/2011 |

\* cited by examiner

*Primary Examiner* — Michael Lebentritt
(74) *Attorney, Agent, or Firm* — Christie, Parker & Hale, LLP

(57) ABSTRACT

A pyrene-based compound, an organic light-emitting diode including the compound and an organic light-emitting apparatus including the compound are disclosed.

20 Claims, 1 Drawing Sheet

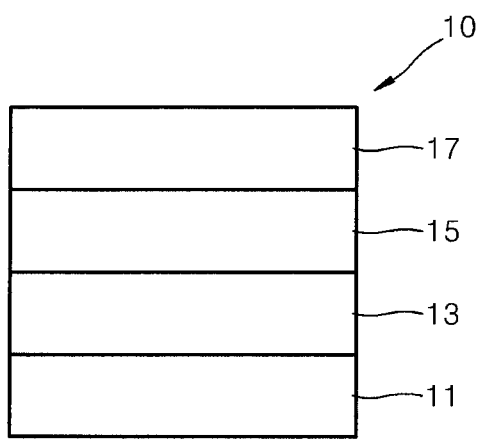

PYRENE-BASED COMPOUND, ORGANIC LIGHT-EMITTING DIODE COMPRISING THE SAME AND ORGANIC LIGHT-EMITTING APPARATUS COMPRISING THE SAME

CROSS-REFERENCE TO RELATED PATENT APPLICATION

This application claims priority to and the benefit of Korean Patent Application No. 10-2012-0022036, filed on Mar. 2, 2012 in the Korean Intellectual Property Office, the entire content of which is incorporated herein by reference.

BACKGROUND

1. Technical Field

The present invention relates to a compound for an organic light-emitting diode (OLED), an OLED, and an organic light-emitting apparatus.

2. Description of the Related Art

Organic light-emitting diodes (OLEDs) are self-emission diodes that have wide viewing angles, high contrast ratios, short response times, and good brightness, driving voltage, and response speed characteristics. Also, OLEDs are capable of generating multi-color images.

In a typical OLED, an anode is formed on a substrate, and a hole transport layer, emission layer, electron transport layer, and cathode are sequentially formed (in that order) on the anode. In this regard, the hole transport layer, the emission layer, and the electron transport layer are organic thin layers that include organic compounds.

The operating principle of an OLED having the above structure will now be described. Holes injected from the anode pass through the hole transport layer and migrate toward the emission layer, and electrons injected from the cathode pass through the electron transport layer and migrate toward the emission layer. Carriers, such as the holes and electrons, are recombined in the emission layer to generate excitons, and then the excitons change from an excited state to a ground state, thereby generating light.

SUMMARY

Embodiments of the present invention provide a pyrene-based compound, an organic light-emitting diode including the compound, and an organic light-emitting apparatus including the compound.

According to an aspect of the present invention, there is provided a pyrene-based compound represented by Formula 1 below:

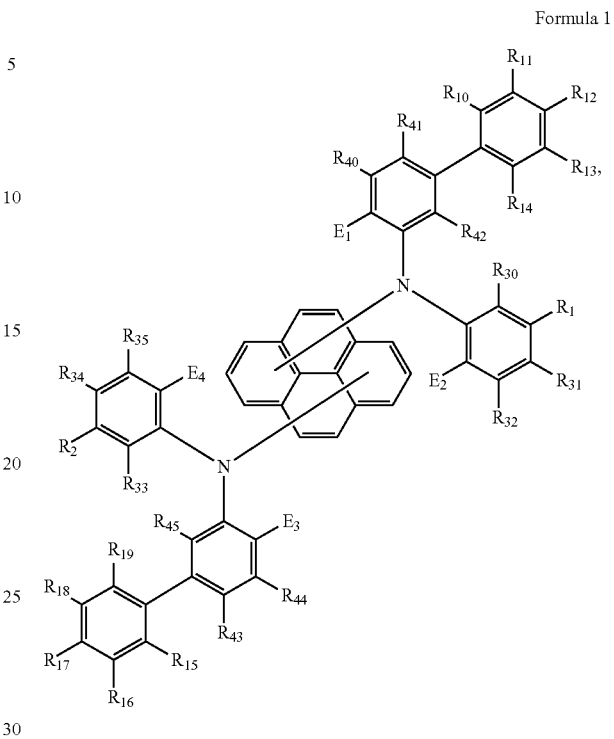

Formula 1

In Formula 1, $E_1$ to $E_4$ may each independently be —F; —CN; or a $C_1$-$C_{60}$ alkyl group substituted with at least one —F. $R_1$, $R_2$, $R_{10}$ to $R_{19}$, $R_{30}$ to $R_{35}$, and $R_{40}$ to $R_{45}$ are each independently one of hydrogen; deuterium; —F; —Cl; —Br; —I; —CN; a hydroxyl group; a nitro group; an amino group; an amidino group; hydrazine; hydrazone; a carboxyl group or a salt thereof; a sulfonic acid group or a salt thereof; a phosphoric acid group or a salt thereof; a $C_1$-$C_{60}$ alkyl group, a $C_1$-$C_{60}$ alkoxy group, a $C_2$-$C_{60}$ alkenyl group, a $C_2$-$C_{60}$ alkynyl group; a $C_1$-$C_{60}$ alkyl group, a $C_1$-$C_{60}$ alkoxy group, a $C_2$-$C_{60}$ alkenyl group, or a $C_2$-$C_{60}$ alkynyl group substituted with at least one of deuterium, —F, —Cl, —Br, —I, —CN, a hydroxyl group, a nitro group, an amino group, an amidino group, hydrazine, hydrazone, a carboxyl group or a salt thereof, a sulfonic acid group or a salt thereof, or a phosphoric acid group or a salt thereof; a $C_3$-$C_{60}$ cycloalkyl group, a $C_3$-$C_{60}$ cycloalkenyl group, a $C_6$-$C_{60}$ aryl group, a $C_2$-$C_{60}$ heteroaryl group, a $C_6$-$C_{60}$ aralkyl group, a $C_6$-$C_{60}$ aryloxy group, or a $C_6$-$C_{60}$ arylthio group; a $C_3$-$C_{60}$ cycloalkyl group, a $C_3$-$C_{60}$ cycloalkenyl group, a $C_6$-$C_{60}$ aryl group, a $C_2$-$C_{60}$ heteroaryl group, a $C_6$-$C_{60}$ aralkyl group, a $C_6$-$C_{60}$ aryloxy group, or a $C_6$-$C_{60}$ arylthio group substituted with at least one of deuterium, —F, —Cl, —Br, —I, —CN, a hydroxyl group, a nitro group, an amino group, an amidino group, hydrazine, hydrazone, a carboxyl group or a salt thereof, a sulfonic acid group or a salt thereof, a phosphoric acid group or a salt thereof, a $C_1$-$C_{60}$ alkyl group, a $C_1$-$C_{60}$ alkyl group substituted with at least one of —F, a $C_1$-$C_{60}$ alkoxy group, a $C_2$-$C_{60}$ alkenyl group, a $C_2$-$C_{60}$ alkynyl group, a $C_6$-$C_{60}$ aryl group, a $C_6$-$C_{60}$ aryl group substituted with at least one —F, and a $C_2$-$C_{60}$ heteroaryl group; —N($Q_1$)($Q_2$); and —Si($Q_3$)($Q_4$)

($Q_5$) (where $Q_1$ to $Q_5$ are each independently one of a $C_1$-$C_{60}$ alkyl group, a $C_1$-$C_{60}$ alkoxy group, a $C_2$-$C_{60}$ alkenyl group, a $C_2$-$C_{60}$ alkynyl group, a $C_3$-$C_{60}$ cycloalkyl group, a $C_3$-$C_{60}$ cycloalkenyl group, a $C_6$-$C_{60}$ aryl group, a $C_2$-$C_{60}$ heteroaryl group, a $C_6$-$C_{60}$ aralkyl group, a $C_6$-$C_{60}$ aryloxy group, or a $C_6$-$C_{60}$ arylthio group).

At least one of $R_1$, $R_{10}$ to $R_{14}$ and $R_{30}$ to $R_{32}$, and at least one of $R_2$, $R_{15}$ to $R_{19}$ and $R_{33}$ to $R_{35}$ are each independently selected from —F; —CN; a $C_1$-$C_{60}$ alkyl group substituted with at least one —F; and a $C_6$-$C_{60}$ aryl group substituted with at least one of —F, —CN, and a $C_1$-$C_{60}$ alkyl group substituted with at least one —F.

According to another aspect of the present invention, there is provided an organic light-emitting diode including a first electrode; a second electrode opposite the first electrode; and an organic layer between the first electrode and the second electrode. The organic layer includes at least one pyrene-based compound represented by Formula 1.

According to another aspect of the present invention, there is provided an organic light-emitting apparatus including a substrate including first subpixels, second subpixels, and third subpixels; a plurality of first electrodes, each separately formed for the first subpixels, the second subpixels, and the third subpixels of the substrate; a second electrode (opposite to the first electrodes) which is a common electrode formed commonly on the first, second, and third subpixels; a first EML between the first electrode of the first subpixels and the second electrode, which emits light of a first color; a second EML between the first electrode of the second subpixels and the second electrode, which emits light of a second color; and a third EML between the first electrode of the third subpixels and the second electrode of the third subpixels which emits light of a third color. The first EML includes at least one pyrene-based compound represented by Formula I. Light resulting from the mixture of the light of the first color, the light of the second color, and the light of the third color is white light, and the light of the first color is blue light.

BRIEF DESCRIPTION OF THE DRAWINGS

The above and other features and advantages of the present invention will become more apparent by reference to the following detailed description, when considered in conjunction with the attached drawing in which:

FIG. 1 is a schematic cross-sectional view of a structure of an organic light-emitting diode according to an embodiment.

DETAILED DESCRIPTION

A pyrene-based compound is represented by Formula 1 below:

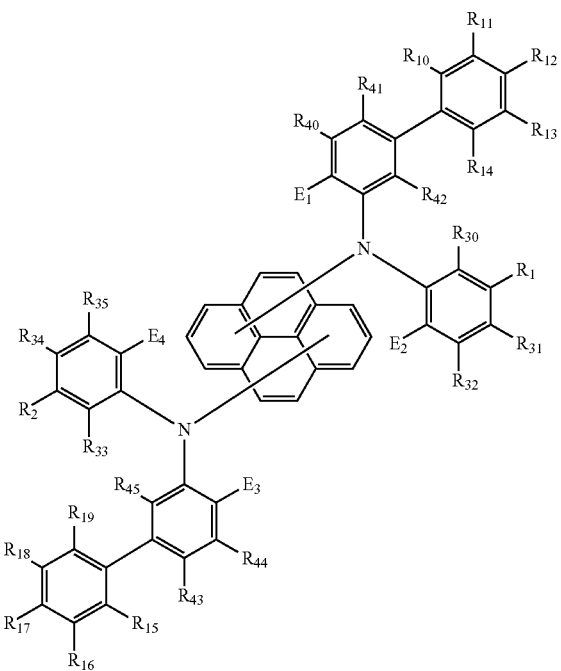

Formula 1

In Formula 1, $E_1$ to $E_4$ are each independently —F; —CN; or a $C_1$-$C_{60}$ alkyl group substituted with at least one —F. For example, $E_1$ to $E_4$ may each independently be —F; —CN; or a $C_1$-$C_{10}$ alkyl group substituted with at least one —F (e.g., methyl, ethyl, propyl, butyl, pentyl, hexyl, or heptyl substituted with at least one —F).

In Formula 1, $E_1$ to $E_4$ may be identical to or different from one another. For example, $E_1$ to $E_4$ may all be —F, but the present disclosure is not limited thereto.

In Formula 1, $R_1$, $R_2$, $R_{10}$ to $R_{19}$, $R_{30}$ to $R_{35}$, and $R_{40}$ to $R_{45}$ are each independently one of hydrogen; deuterium; —F; —Cl; —Br; —I; —CN; a hydroxyl group; a nitro group; an amino group; an amidino group; hydrazine; hydrazone; a carboxyl group or a salt thereof; a sulfonic acid group or a salt thereof; a phosphoric acid group or a salt thereof; a $C_1$-$C_{60}$ alkyl group, a $C_1$-$C_{60}$ alkoxy group, a $C_2$-$C_{60}$ alkenyl group, a $C_2$-$C_{60}$ alkynyl group; a $C_1$-$C_{60}$ alkyl group, a $C_1$-$C_{60}$ alkoxy group, a $C_2$-$C_{60}$ alkenyl group, or a $C_2$-$C_{60}$ alkynyl group substituted with at least one of deuterium, —F, —Cl, —Br, —I, —CN, a hydroxyl group, a nitro group, an amino group, an amidino group, hydrazine, hydrazone, a carboxyl group or a salt thereof, a sulfonic acid group or a salt thereof, or a phosphoric acid group or a salt thereof; a $C_3$-$C_{60}$ cycloalkyl group, a $C_3$-$C_{60}$ cycloalkenyl group, a $C_6$-$C_{60}$ aryl group, a $C_2$-$C_{60}$ heteroaryl group, a $C_6$-$C_{60}$ aralkyl group, a $C_6$-$C_{60}$ aryloxy group, and a $C_6$-$C_{60}$ arylthio group; $C_3$-$C_{60}$ cycloalkyl group, $C_3$-$C_{60}$ cycloalkenyl group, $C_6$-$C_{60}$ aryl group, $C_2$-$C_{60}$ heteroaryl group, $C_6$-$C_{60}$ aralkyl group, $C_6$-$C_{60}$ aryloxy group, or a $C_6$-$C_{60}$ arylthio group substituted with at least one of deuterium, —F, —Cl, —Br, —I, —CN, a hydroxyl group, a nitro group, an amino group, an amidino group, hydrazine, hydrazone, a carboxyl group or a salt thereof, a sulfonic acid group or a salt thereof, a phosphoric acid group or a salt thereof, a $C_1$-$C_{60}$ alkyl group, a $C_1$-$C_{60}$ alkyl group substituted with at least one —F, a $C_1$-$C_{60}$ alkoxy group, a $C_2$-$C_{60}$ alkenyl group, a $C_2$-$C_{60}$ alkynyl group, a $C_6$-$C_{60}$ aryl group, a $C_6$-$C_{60}$ aryl group substituted with at least one —F, and a $C_2$-$C_{60}$ heteroaryl group; —N($Q_1$)($Q_2$); or —Si($Q_3$)($Q_4$)($Q_5$) (where $Q_1$ to $Q_5$ are each independently one of a $C_1$-$C_{60}$ alkyl group, a $C_1$-$C_{60}$ alkoxy group, a $C_2$-$C_{60}$ alkenyl group, a $C_2$-$C_{60}$ alkynyl group, a $C_3$-$C_{60}$ cycloalkyl group, a $C_3$-$C_{60}$ cycloalkenyl group, a $C_6$-$C_{60}$ aryl group, a $C_2$-$C_{60}$ heteroaryl group, a $C_6$-$C_{60}$ aralkyl group, a $C_6$-$C_{60}$ aryloxy group, or a $C_6$-$C_{60}$ arylthio group). At least one of $R_1$, $R_{10}$ to $R_{14}$ and $R_{30}$ to $R_{32}$, and at least one of $R_2$, $R_{15}$ to $R_{19}$ and $R_{33}$ to $R_{35}$ are each independently selected from —F; —CN; a $C_1$-$C_{60}$ alkyl group substituted with at least one —F; and a $C_6$-$C_{60}$ aryl group substituted with at least one of —F, —CN, or a $C_1$-$C_{60}$ alkyl group substituted with at least one —F.

For example, in Formula 1, at least one of $R_{10}$ to $R_{14}$ and at least one of $R_{15}$ to $R_{19}$ may each independently be selected from —F; —CN; a $C_1$-$C_{20}$ alkyl group substituted with at least one —F; a $C_6$-$C_{20}$ aryl group substituted with at least one of —F, —CN, or a $C_1$-$C_{20}$ alkyl group substituted with at least one —F.

According to an embodiment, in Formula 1, at least one of $R_{10}$ to $R_{14}$ and at least one of $R_{15}$ to $R_{19}$ may each independently be selected from —F; —CN; a $C_1$-$C_{10}$ alkyl group substituted with at least one —F; or a phenyl group, a naphthyl group, or an anthryl group substituted with at least one of —F, —CN, or a $C_1$-$C_{10}$ alkyl group substituted with at least one —F, but the present disclosure is not limited thereto.

For example, in Formula 1, $E_1$ to $E_4$ are each independently —F; —CN; or a $C_1$-$C_{10}$ alkyl group substituted with at least one —F. $R_1$, $R_2$, $R_{10}$ to $R_{19}$, $R_{30}$ to $R_{35}$, and $R_{40}$ to $R_{45}$ may each independently be one of hydrogen; deuterium; —F; —Cl; —Br; —I; —CN; a hydroxyl group; a nitro group; an amino group; an amidino group; hydrazine; hydrazone; a carboxyl group or a salt thereof; a sulfonic acid group or a salt thereof; a phosphoric acid group or a salt thereof; a $C_1$-$C_{10}$ alkyl group or a $C_1$-$C_{10}$ alkoxy group; a $C_1$-$C_{10}$ alkyl group or a $C_1$-$C_{10}$ alkoxy group substituted with at least one of deuterium, —F, —Cl, —Br, —I, —CN, a hydroxyl group, a nitro group, an amino group, an amidino group, hydrazine, hydrazone, a carboxyl group or a salt thereof, a sulfonic acid group or a salt thereof, or a phosphoric acid group or a salt thereof; a phenyl group, a naphthyl group, an anthryl group, a fluorenyl group, a dibenzofuranyl group, or a dibenzothiophenyl group; or a phenyl group, a naphthyl group, an anthryl group, a fluorenyl group, a dibenzofuranyl group, or a dibenzothiophenyl group substituted with at least one of deuterium, —F, —Cl, —Br, —I, —CN, a hydroxyl group, a nitro group, an amino group, an amidino group, hydrazine, hydrazone, a carboxyl group or a salt thereof, a sulfonic acid group or a salt thereof, a phosphoric acid group or a salt thereof, a $C_1$-$C_{10}$ alkyl group, a $C_1$-$C_{10}$ alkyl group substituted with at least one —F, a $C_1$-$C_{10}$ alkoxy group, or a phenyl group substituted with at least one —F. At least one of $R_1$, $R_{10}$ to $R_{14}$, and $R_{30}$ to $R_{32}$ and at least one of $R_2$, $R_{15}$ to $R_{19}$, and $R_{33}$ to $R_{35}$ may each independently be selected from —F; —CN; a $C_1$-$C_{10}$ alkyl group substituted with at least one —F; or a phenyl group, a naphthyl group, or an anthryl group substituted with at least one of —F, —CN, or a $C_1$-$C_{10}$ alkyl group substituted with at least one —F.

For example, in Formula 1, $R_1$ and $R_2$ may each independently be one of a phenyl group, a naphthyl group or an anthryl group; or a phenyl group, a naphthyl group or an anthryl group substituted with at least one of —F, —CN, a $C_1$-$C_{10}$ alkyl group substituted with at least one —F, or a phenyl substituted with at least one —F, but the present disclosure is not limited thereto.

In Formula 1,

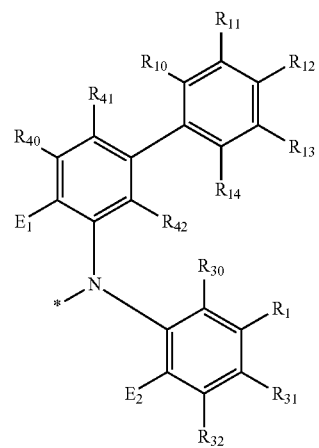

(hereinafter, referred to as "a first diarylamino group") and

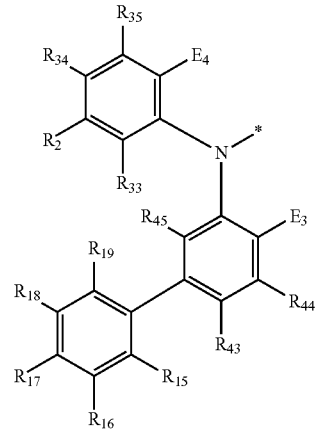

(hereinafter, referred to as "a second diarylamino group") may be identical to each other. Otherwise, in Formula 1, the first diarylamino group and the second diarylamino group may be different from each other (e.g., refer to Compounds 13 and 14 below).

According to the bonding sites of the first diarylamino group and the diarylamino group with the pyrene core, Formula 1 above may be represented by Formulae 1A (in which the first and second diarylamino groups are bound to the 4- and 9-position carbons of the pyrene core), 1B (in which the first diarylamino group and the second diarylamino group are bound to the 2-position carbon and the 7-position carbon of the pyrene core), or 1C (in which the first diarylamino group and the second diarylamino group are bound to the 1-position carbon and the 6-position carbon of the pyrene core). Formulae 1A, 1B and 1C are depicted below.

Formula 1A
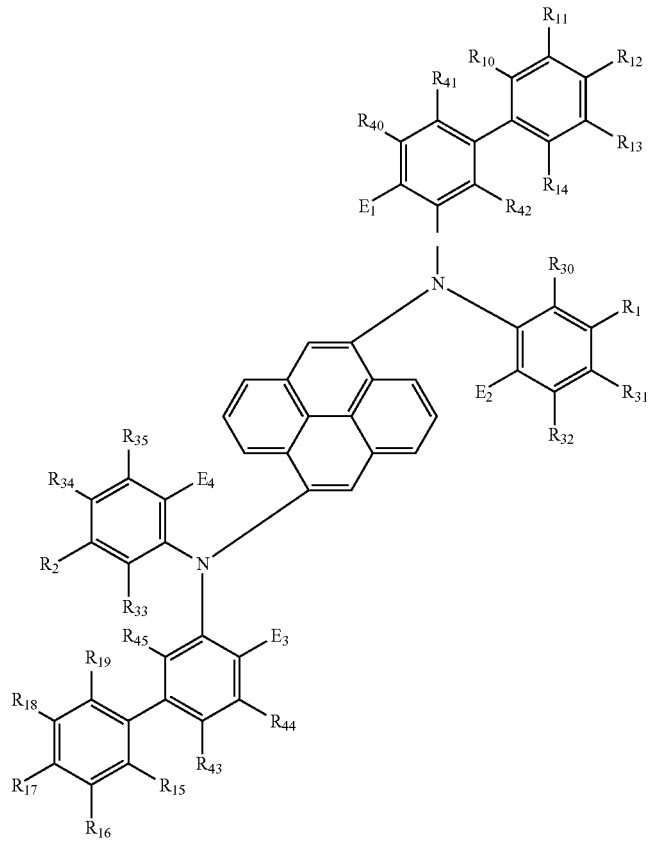
Formula 1B
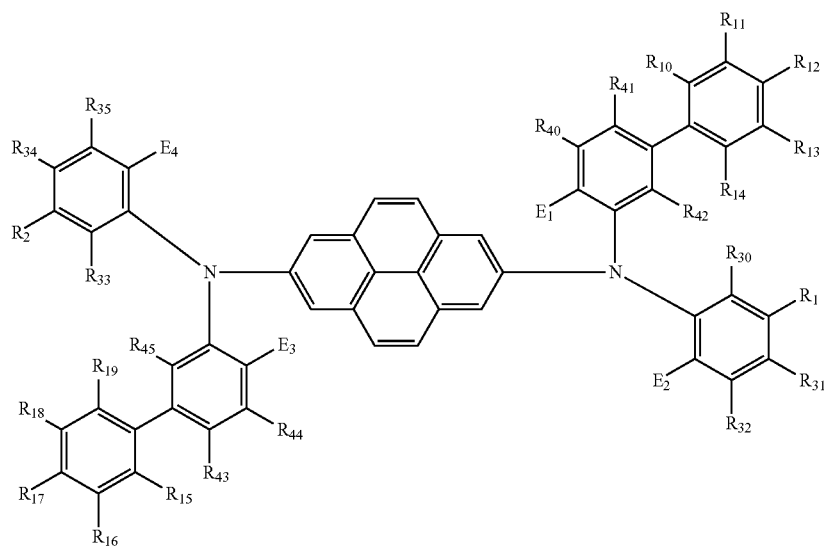
Formula 1C
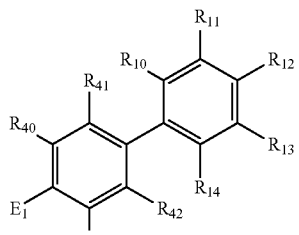

-continued

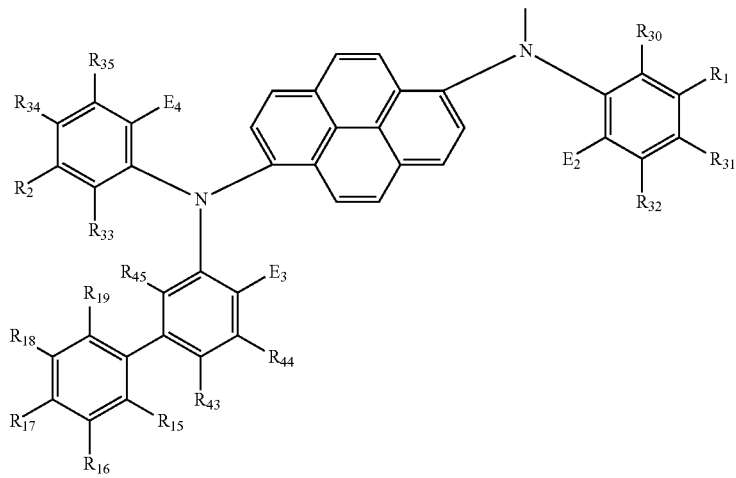

In Formulae 1A, 1B, and 1C, $E_1$ to $E_4$, $R_1$, $R_2$, $R_{10}$ to $R_{19}$, $R_{30}$ to $R_{35}$, and $R_{40}$ to $R_{45}$ are as described above. In Formulae 1A, 1B, and 1C, the first diarylamino group and the second diarylamino group may be identical to or different from each other.

For example, the pyrene-based compound may be represented by Formula 1A, but is not limited thereto.

Meanwhile, the pyrene-based compound may be represented by Formula 1-(1) or 1-(2) below:

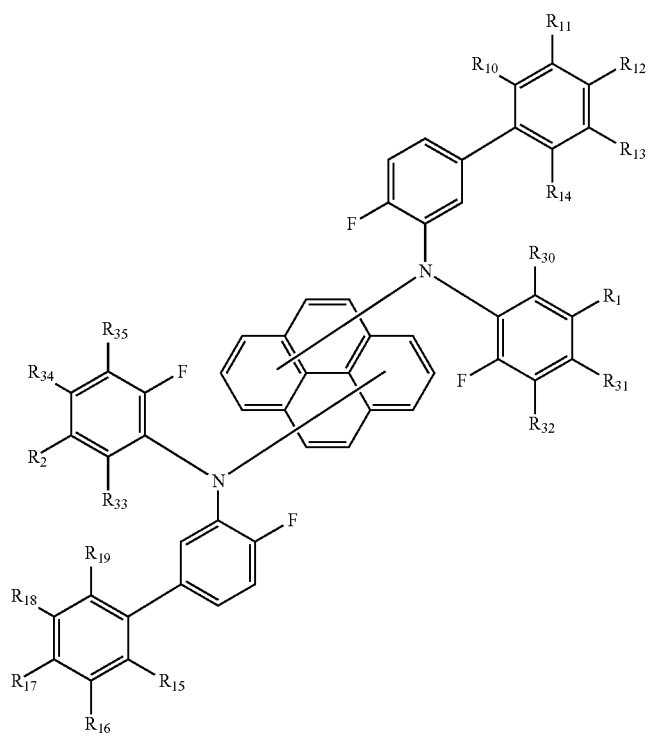

Formula 1-(1)

Formula 1-(2)

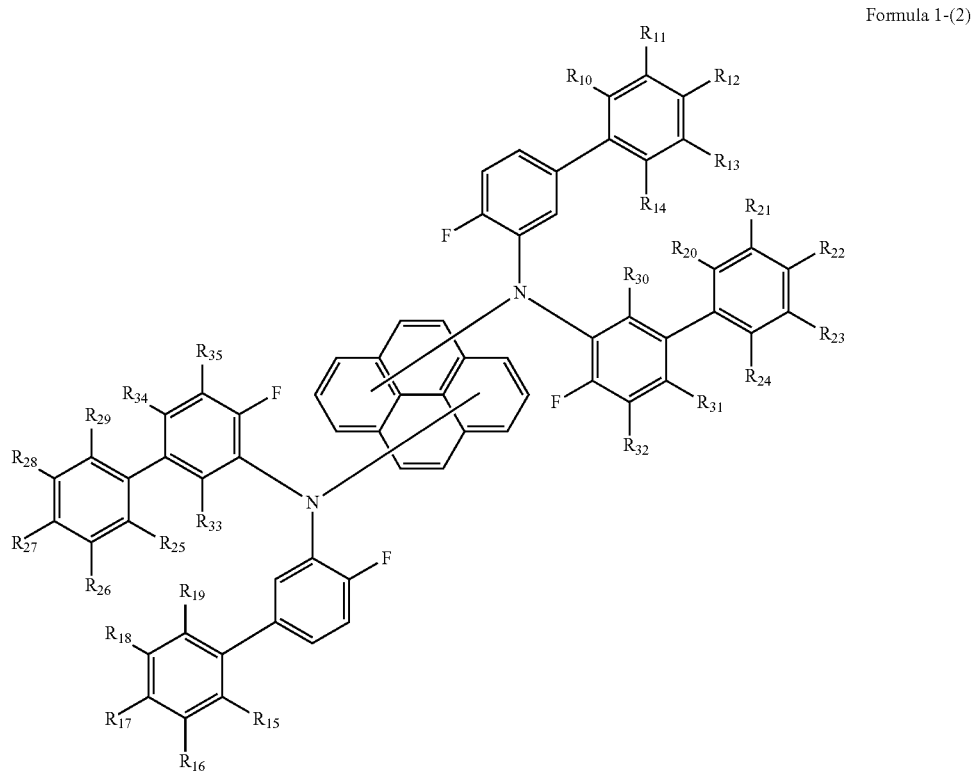

In Formulae 1-(1) and 1-(2), like numbered substituents are the same as described above. Meanwhile, in Formulae 1-(1) and 1-(2), $R_{20}$ to $R_{29}$ are each independently selected from the substituents described above with respect to $R_1$.

In Formula 1-(1), the first diarylamino group and the second diarylamino group may be identical to or different from each other.

In Formula 1-(2), the first diarylamino group and the second diarylamino group may be identical to or different from each other.

In Formulae 1-(1) and 1-(2), the first diarylamino group and the second diarylamino group may be bound to the 4-position carbon and the 9-position carbon of the pyrene core, respectively (see Formula 1A above); to the 2-position carbon and the 7-position carbon of the pyrene core, respectively (see Formula 1B above); or to the 1-position carbon and the 6-position carbon of the pyrene core, respectively (see Formula 1C above), but are not limited thereto.

For example, the pyrene-based compound may be represented by Formula 1-(1) or 1-(2) above, and in Formulae 1-(1) and 1-(2), at least one of $R_{10}$ to $R_{14}$ and at least one of $R_{15}$ to $R_{19}$ are each independently selected from —F; —CN; a $C_1$-$C_{10}$ alkyl group substituted with at least one —F; or a phenyl group, a naphthyl group, or an anthryl group substituted with at least one of —F, —CN, or a $C_1$-$C_{10}$ alkyl group substituted with at least one —F.

According to an embodiment, the pyrene-based compound may be represented by Formula 1-(1) above, and in Formulae 1-(1), at least one of $R_{20}$ to $R_{24}$ and at least one of $R_{25}$ to $R_{29}$ are each independently selected from —F; —CN; a $C_1$-$C_{10}$ alkyl group; a $C_1$-$C_{10}$ alkyl group substituted with at least one —F; or a phenyl group, a naphthyl group, or an anthryl group.

According to another embodiment, the pyrene-based compound may be represented by Formula 1-(2) above, and in Formulae 1-(2), at least one of $R_{20}$ to $R_{24}$ and at least one of $R_{25}$ to $R_{29}$ are each independently selected from —F; —CN; a $C_1$-$C_{10}$ alkyl group; a $C_1$-$C_{10}$ alkyl group substituted with at least one —F; or a phenyl group, a naphthyl group, or an anthryl group; a phenyl group, a naphthyl group, or an anthryl group substituted with at least one of —F, —CN, or a $C_1$-$C_{10}$ alkyl group substituted with at least one —F.

The pyrene-based compound represented by Formula 1 above may be, for example, one of Compounds 1 to 50, but is not limited thereto.

13
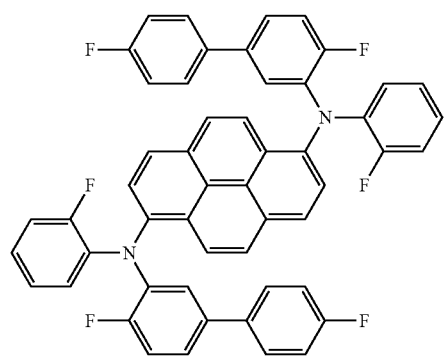
1
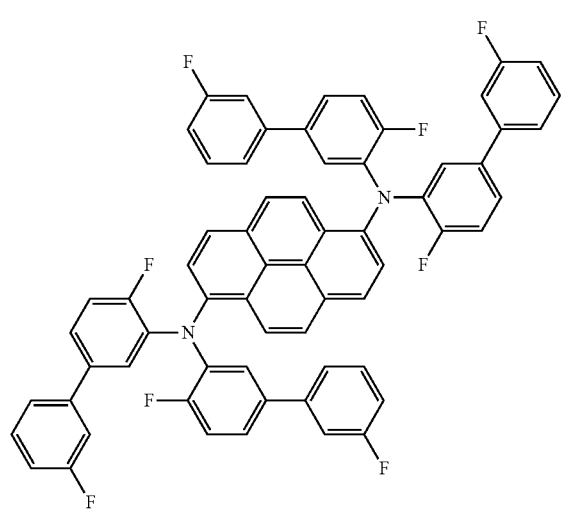
3
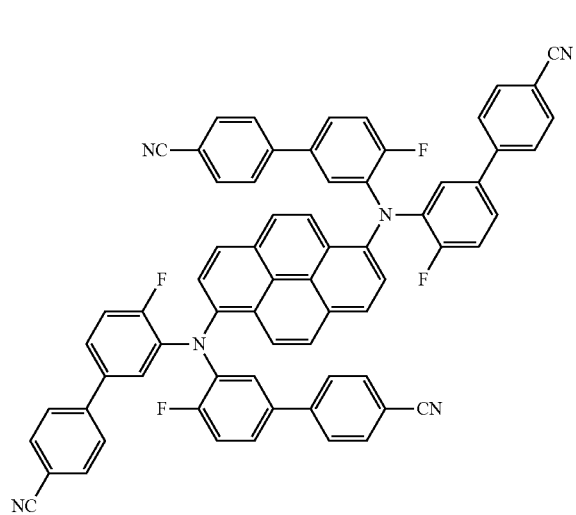
5
14
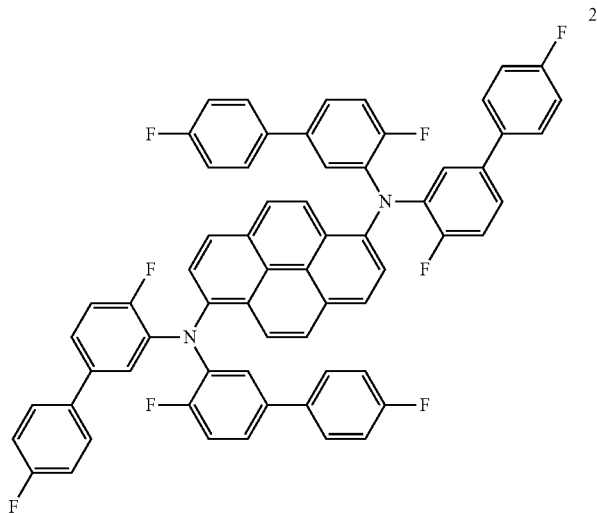
2
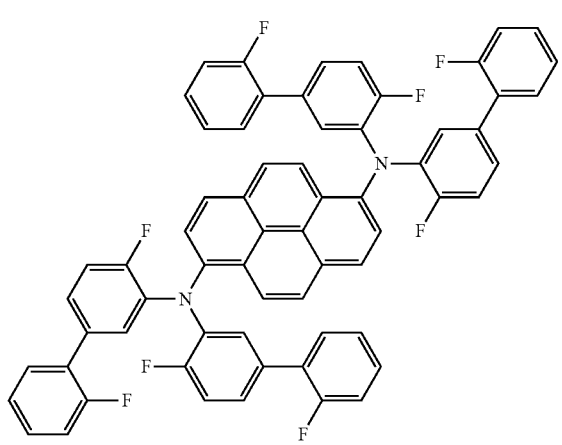
4
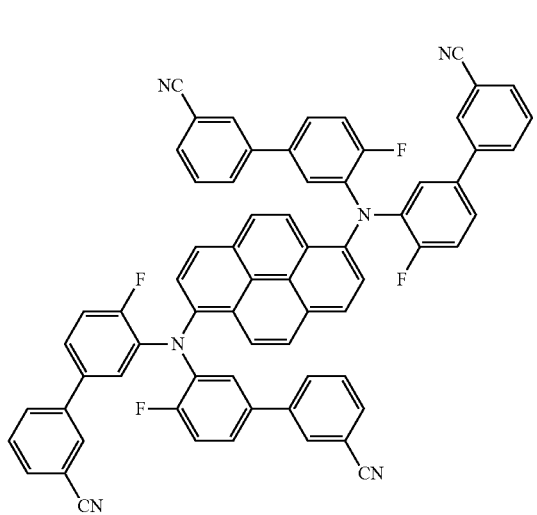
6

-continued
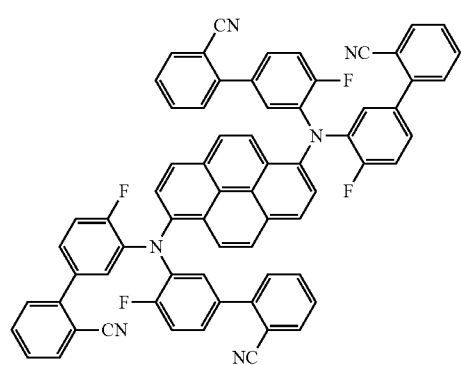
7
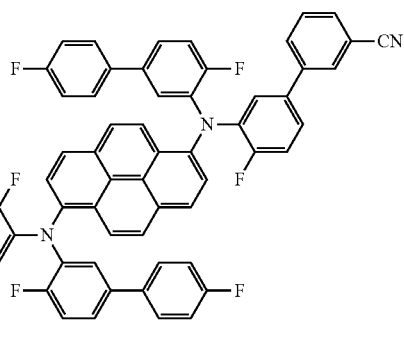
8
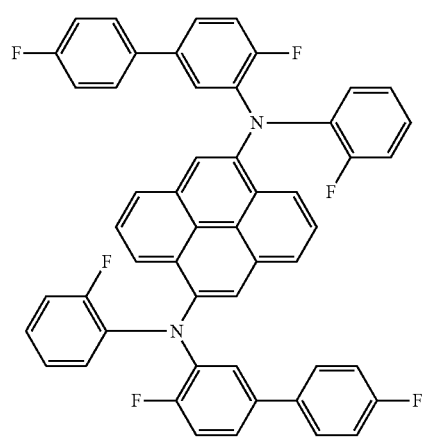
9
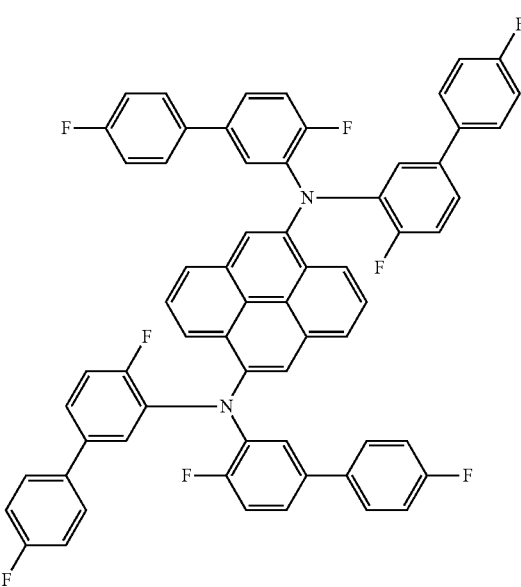
10
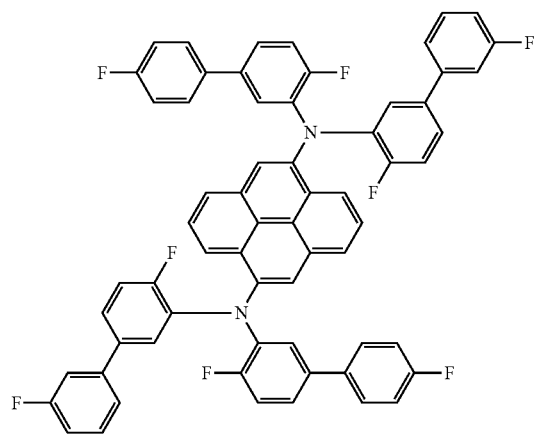
11
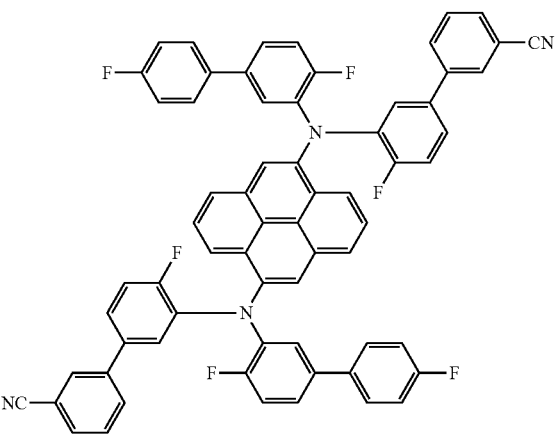
12

-continued
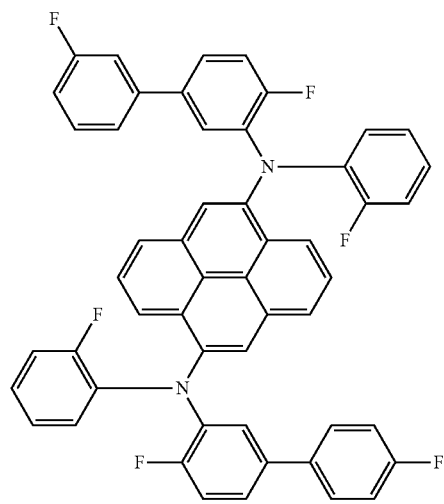
13
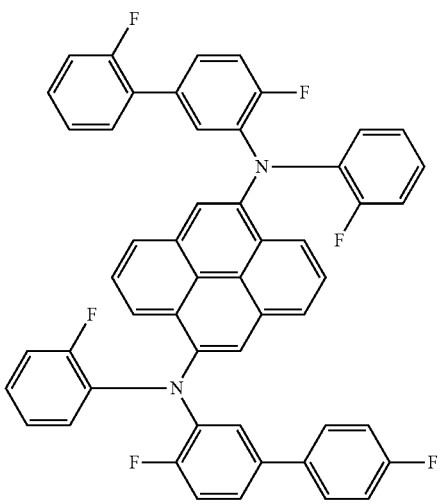
14
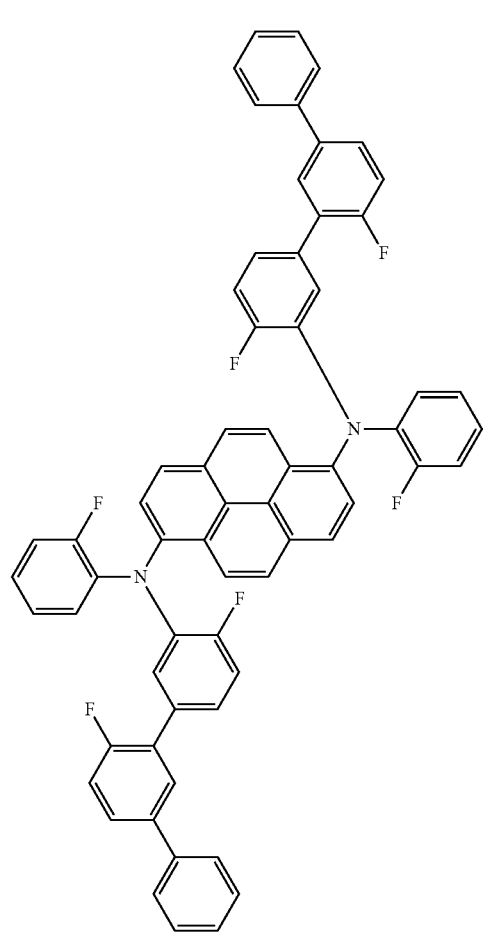
15
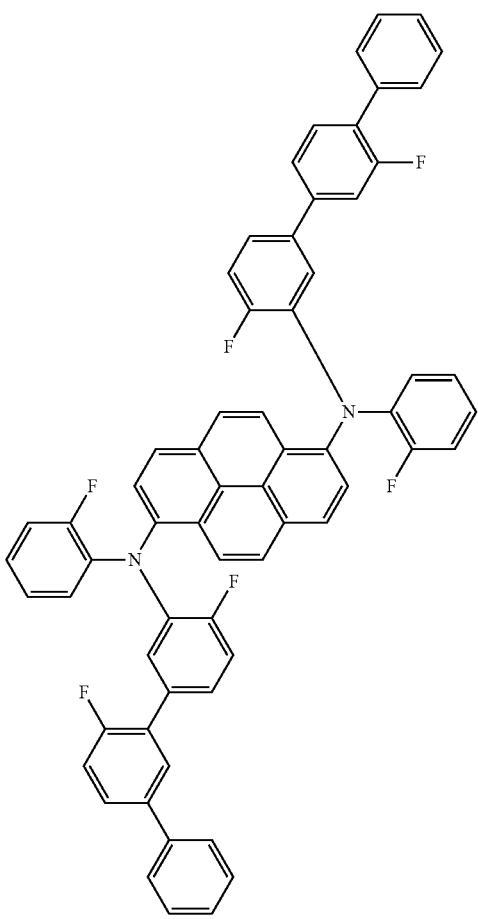
16

-continued
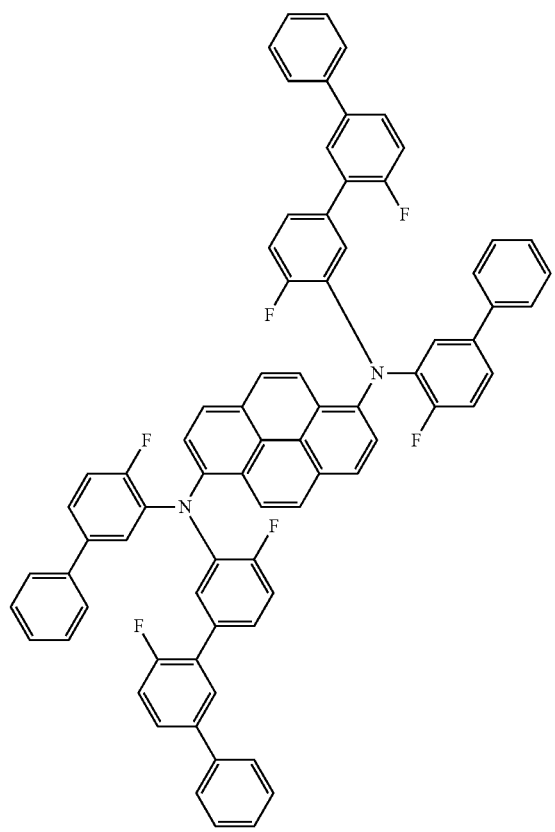
17
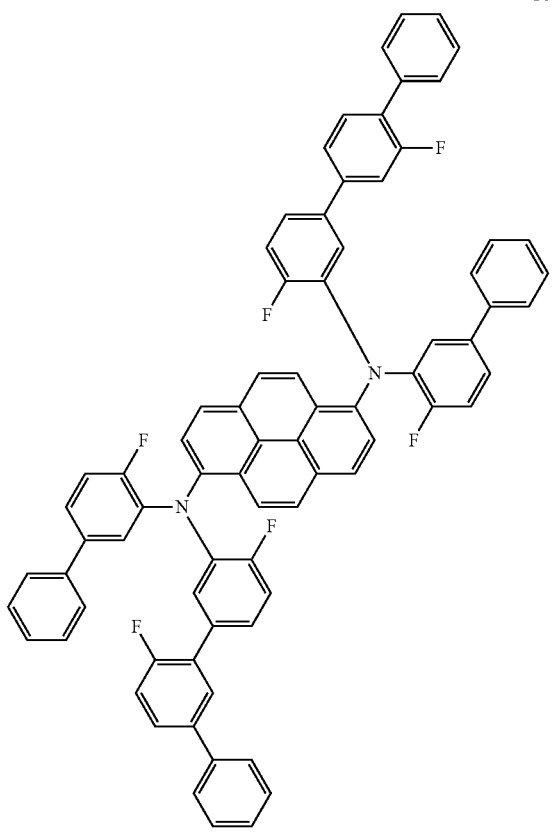
18

-continued
19
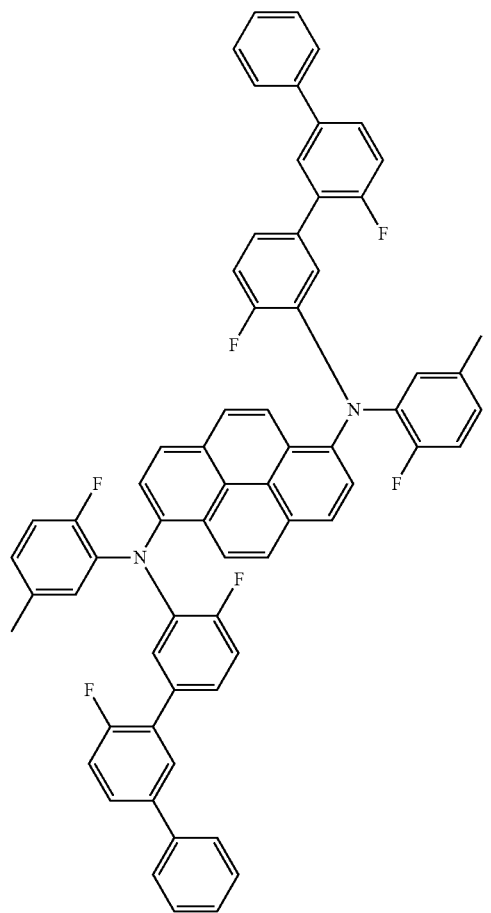
20
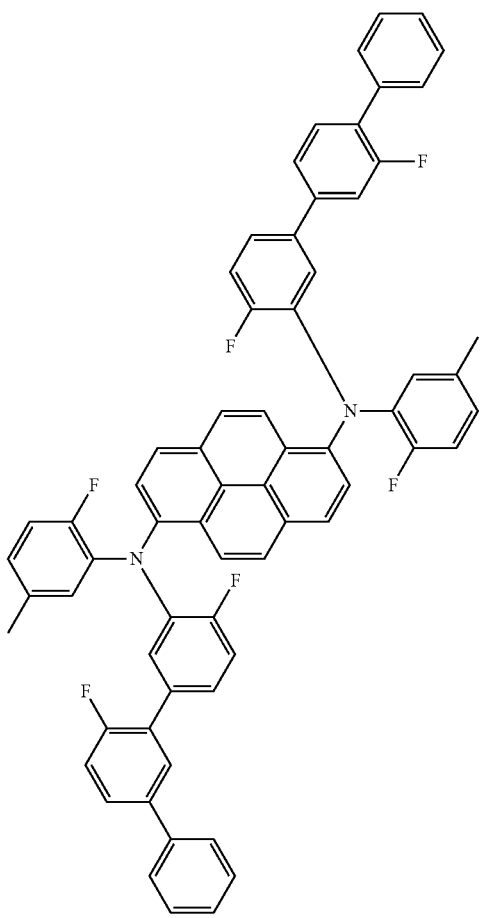

-continued
21
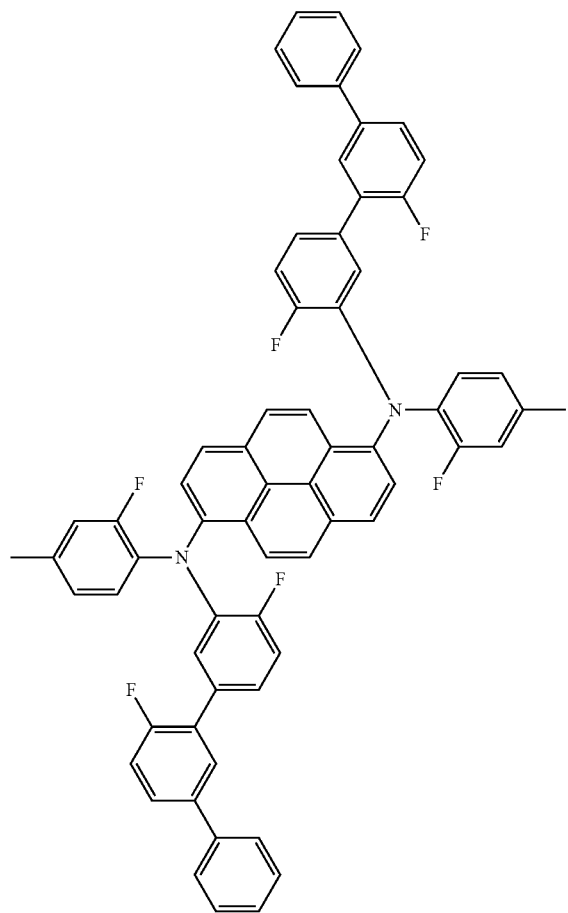
22
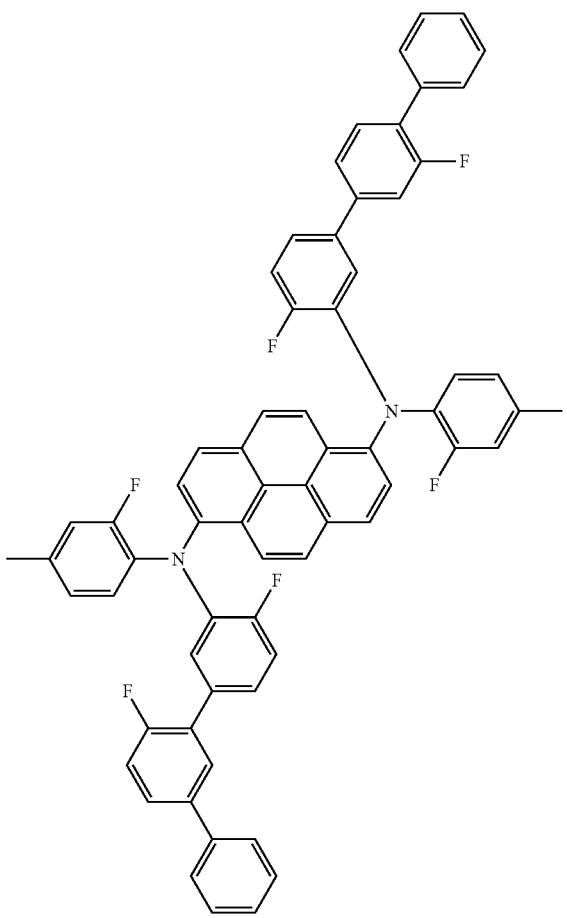

-continued
23
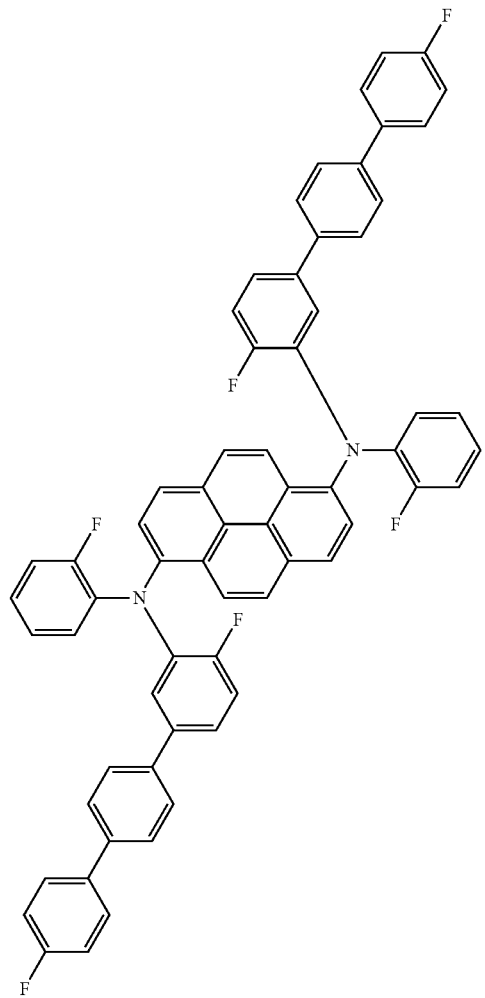
24
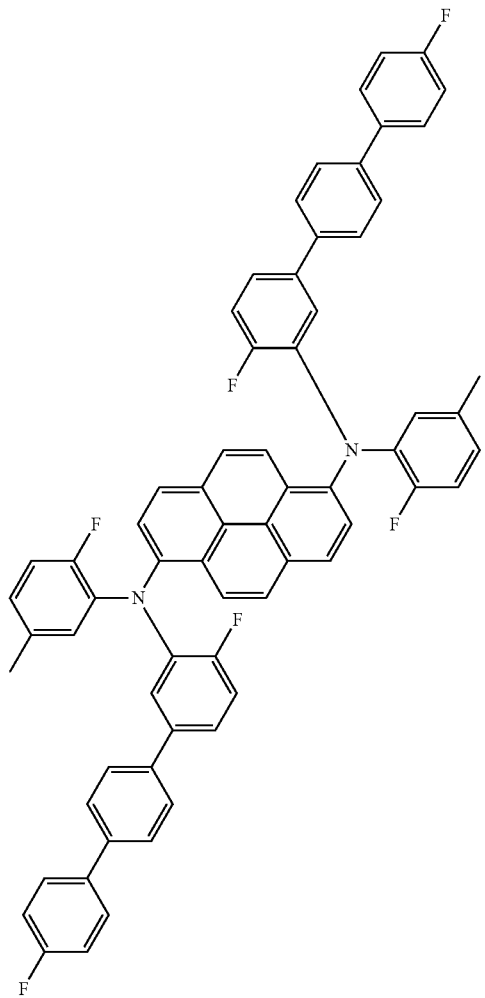

-continued
25
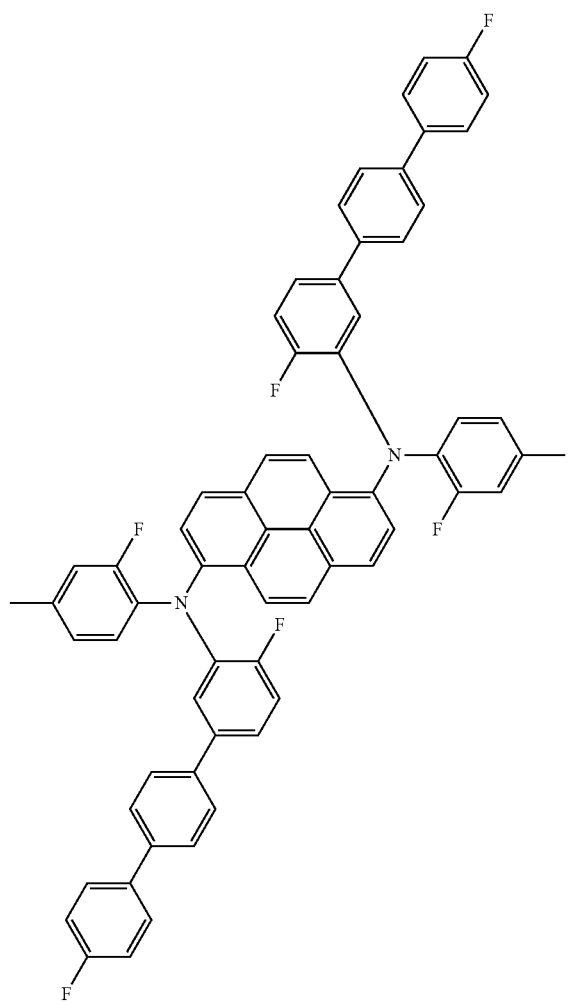
26
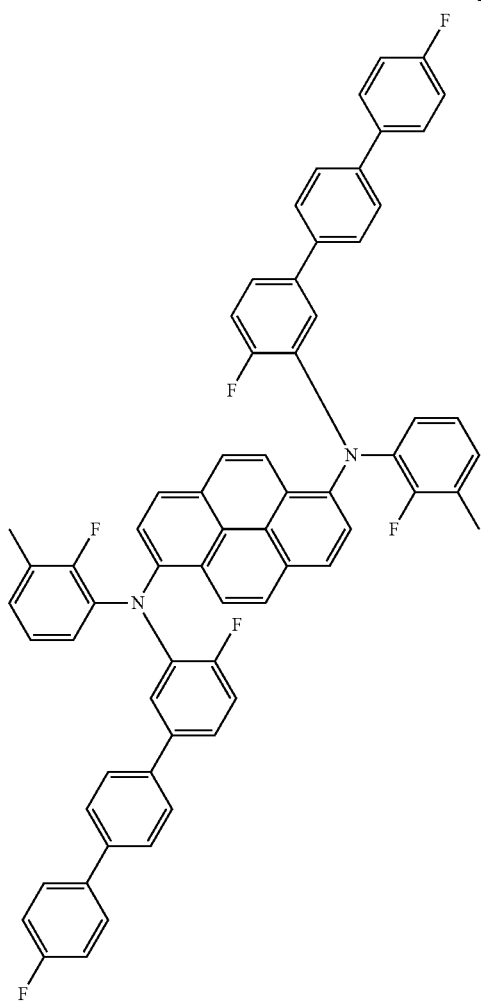

-continued
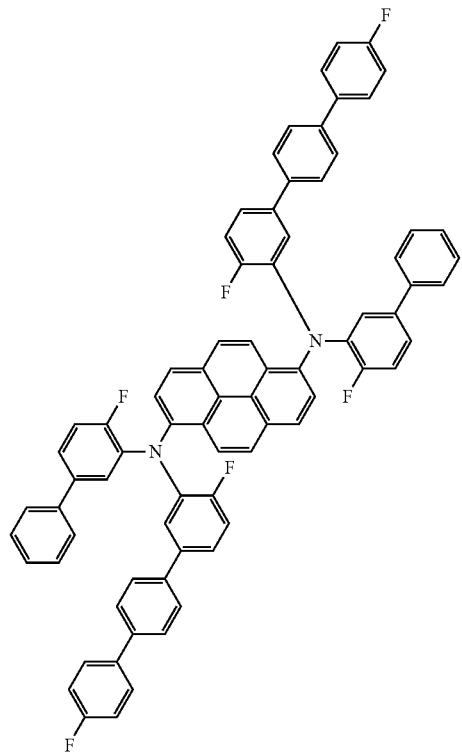
27
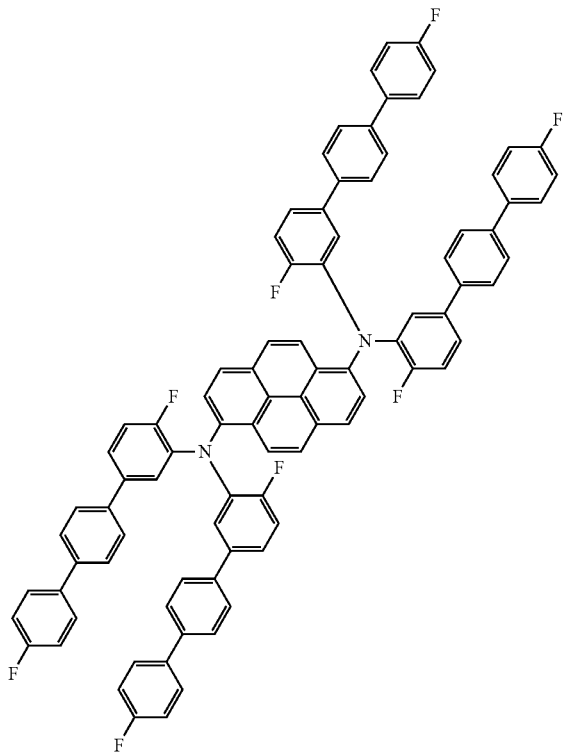
28
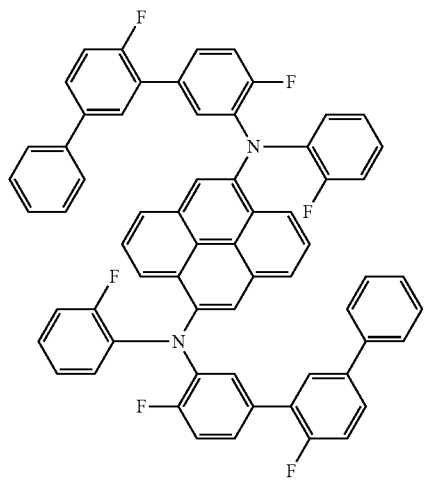
29
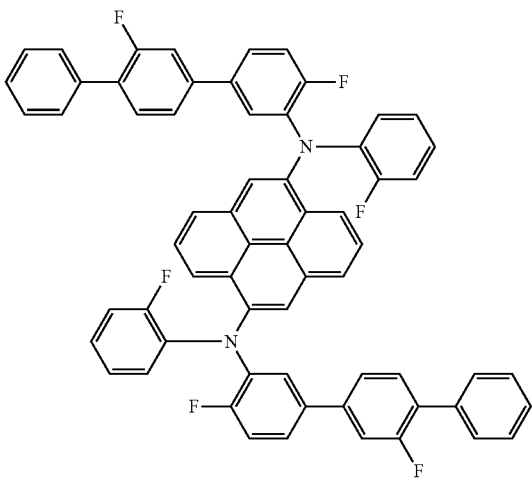
30

31
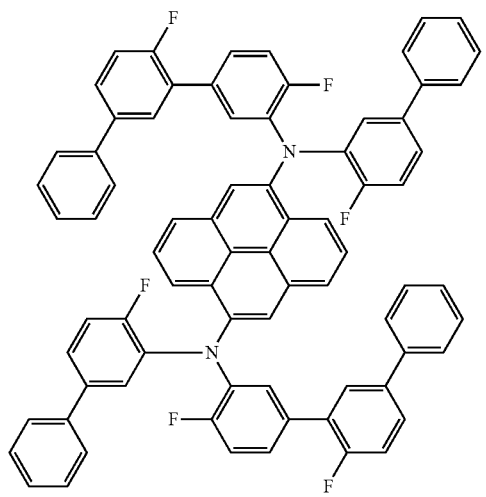
32
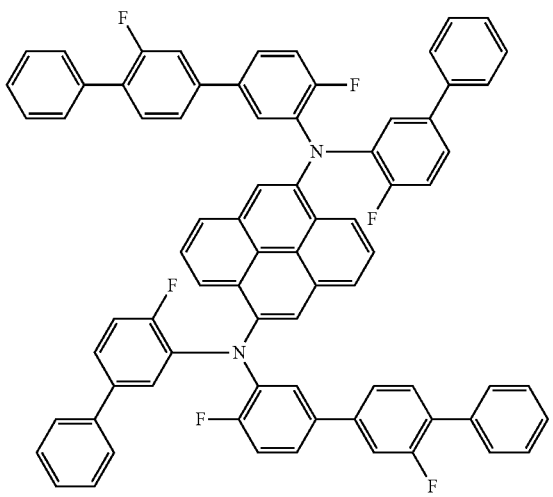
33
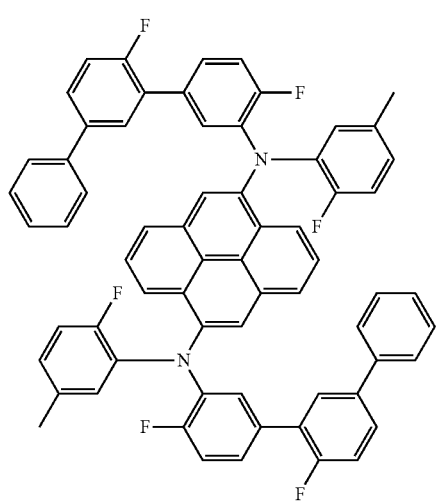
34
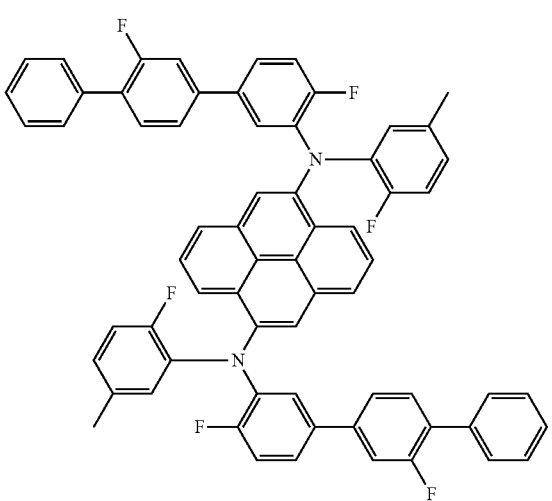
35
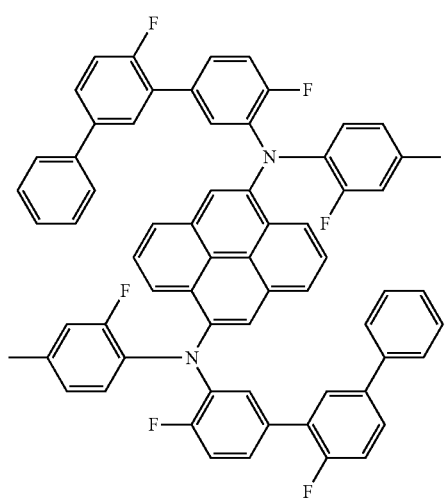
36
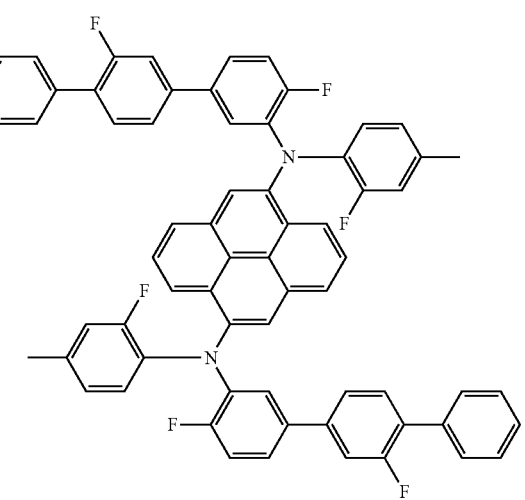

-continued
37
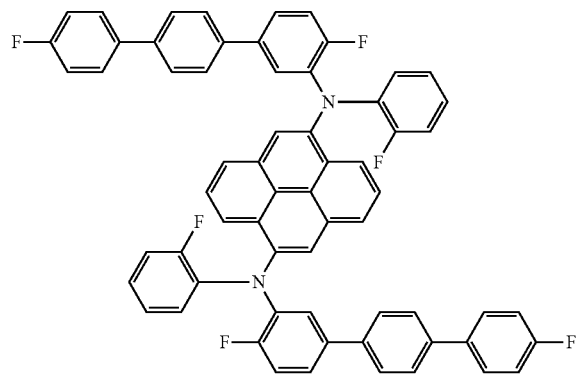
38
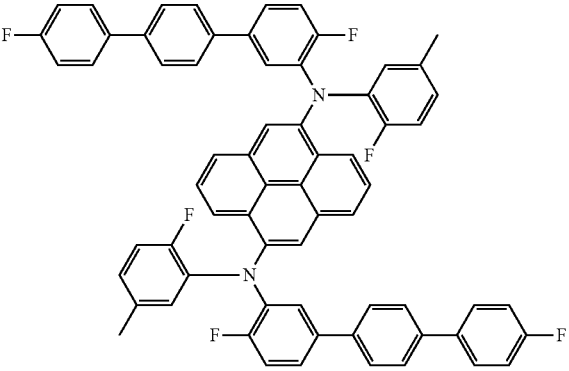
39
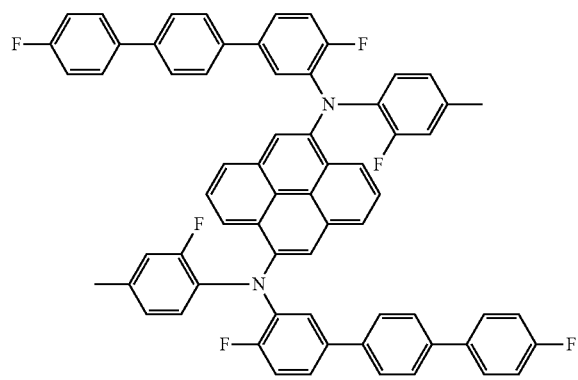
40
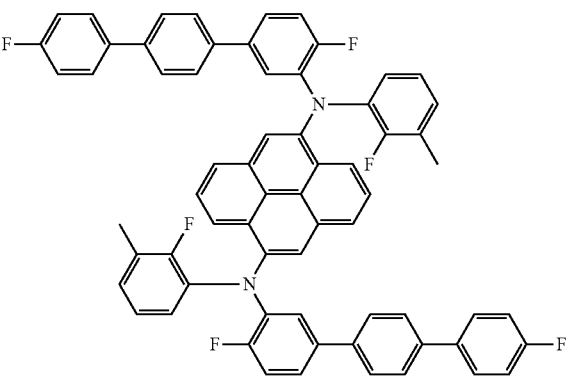
41
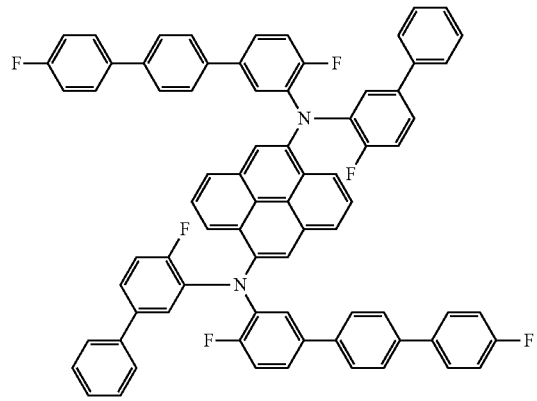
42
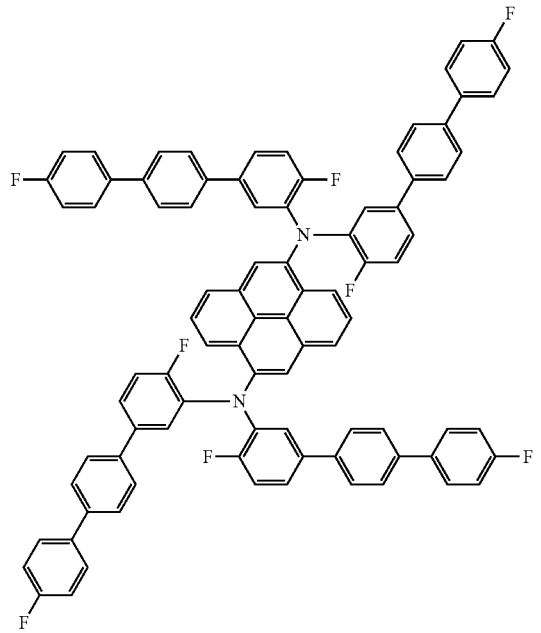

43
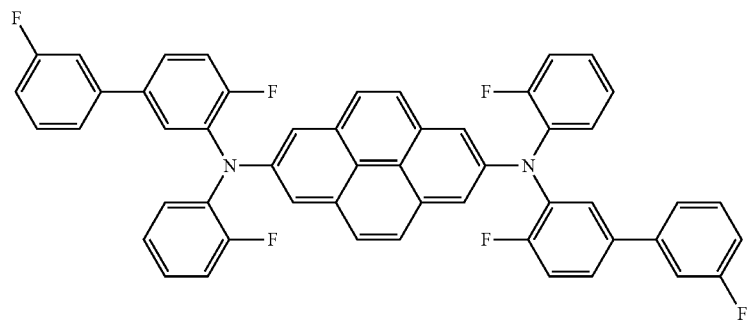
44
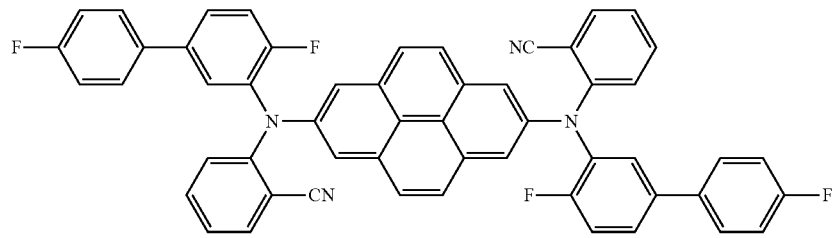
45
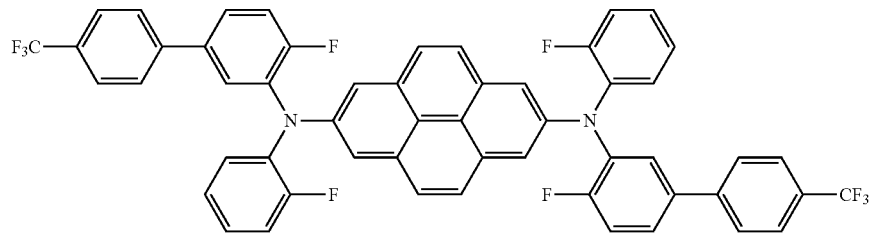
46
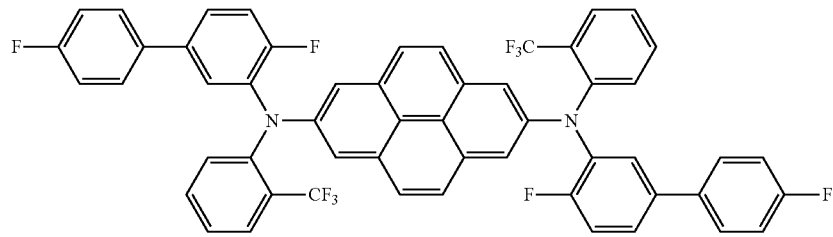
47
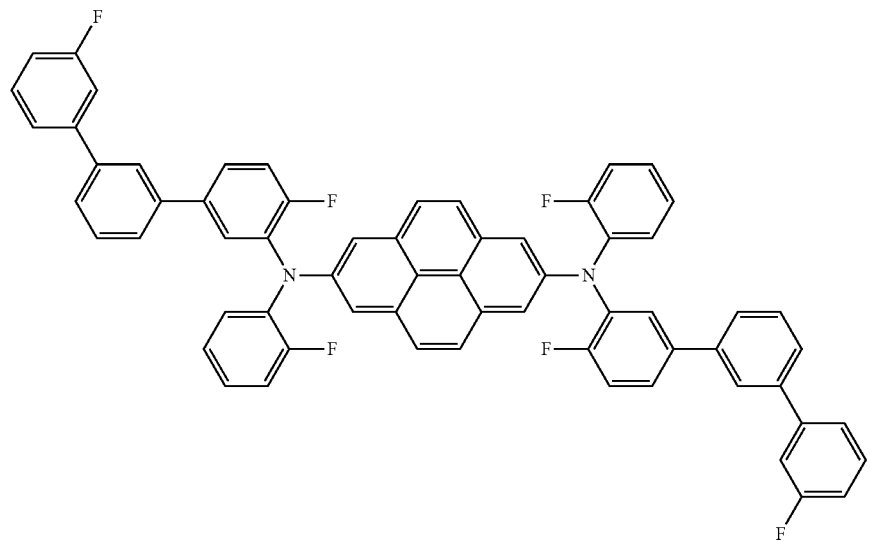

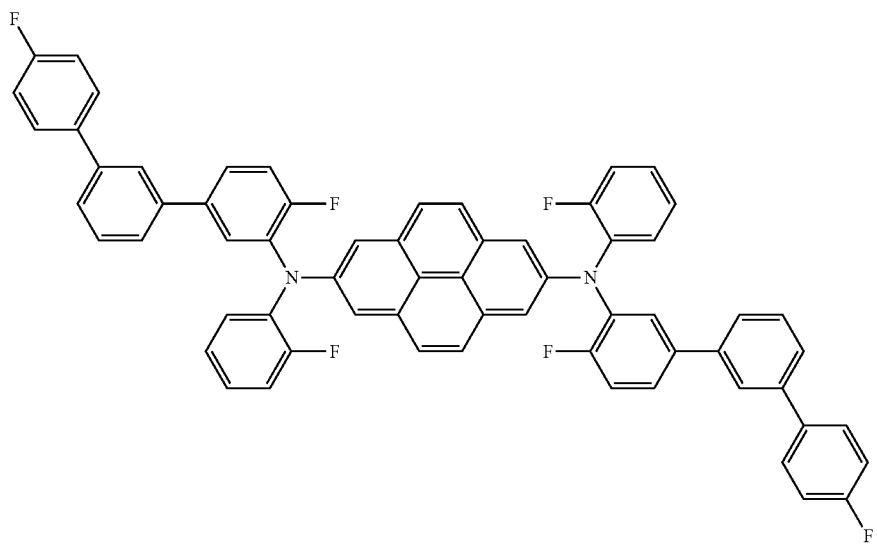

48

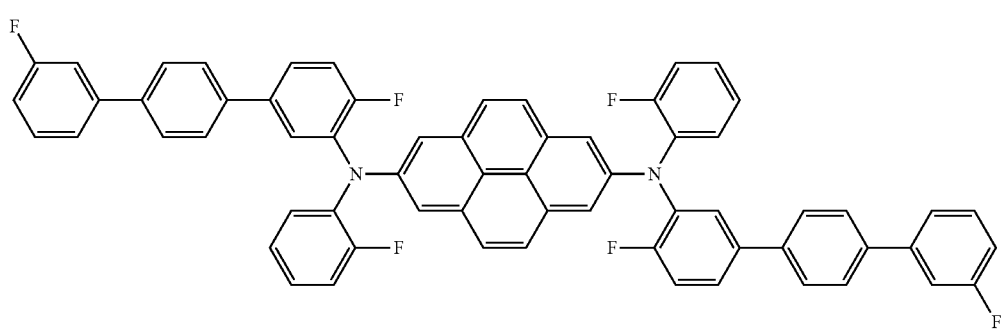

49

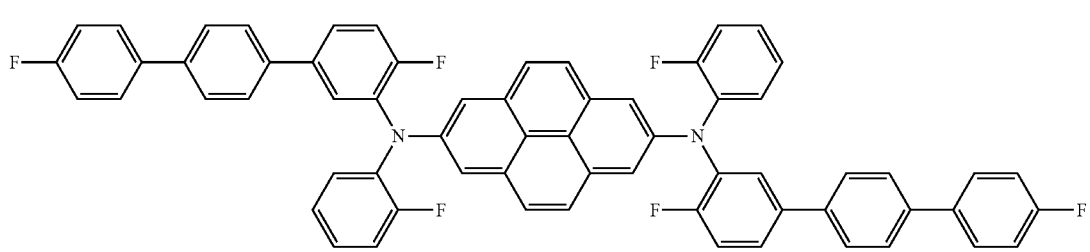

50

In Formula 1, $E_1$ to $E_4$ are each independently an electron withdrawing group such as —F; —CN; or a $C_1$-$C_{60}$ alkyl group substituted with at least one —F, and the pyrene compound represented by Formula 1 above may emit blue light, which has a relatively short wavelength. For example, a maximum peak in the photoluminescence (PL) spectrum of a pyrene-based compound represented by Formula 1 above in a toluene solvent may be 450 nm or less. Thus, the pyrene-based compound represented by Formula 1 above may emit blue light having good color purity. For example, an OLED using the pyrene-based compound may provide blue light having good color purity in which the y-coordinate is 0.1 or less, for example, 0.09 or less, and thus the OLED may emit blue light that is close to the NTSC or sRGB standard.

Also, the moieties A and B (identified in Formula 1' below) of the pyrene-based compound represented by Formula 1 serve to increase electrical stability, and thus the pyrene-based compound may have a long lifetime:

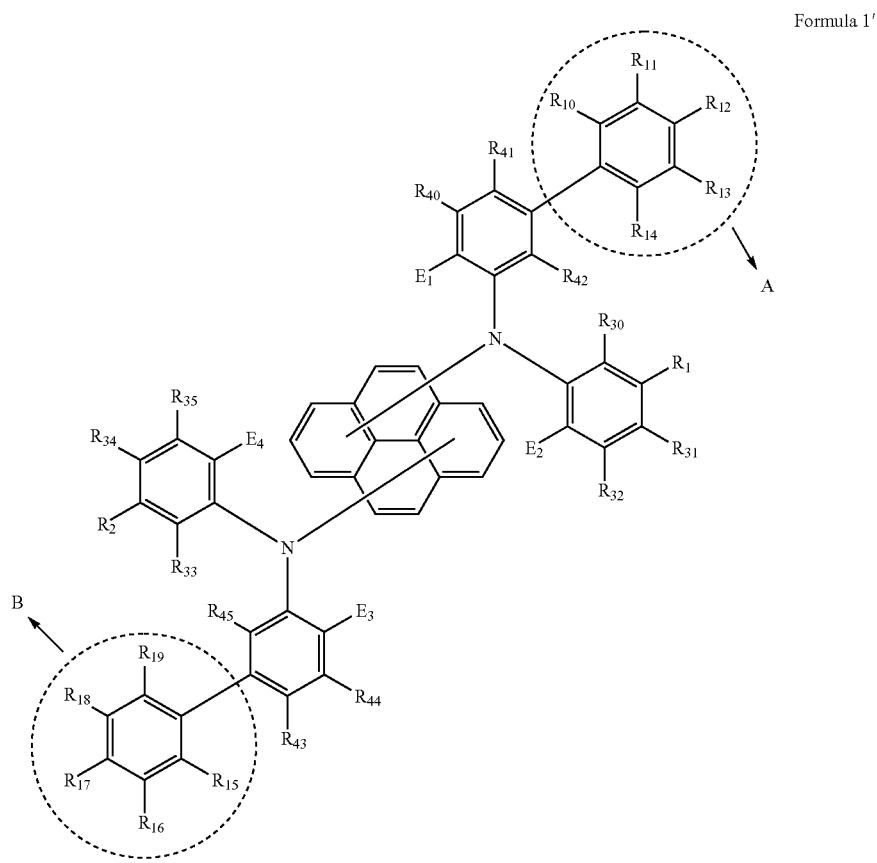

Formula 1'

Therefore, OLEDs using the pyrene-based compound represented by Formula 1 above may provide good electrical characteristics (i.e., low driving voltage, high-current density, long lifetime, etc.) and good color purity.

The pyrene-based compound of Formula 1 above may be synthesized using commonly known organic synthesis methods. A synthesis method of the pyrene-based compound would be easily recognized by one of ordinary skill in the art, especially with reference to the Examples described below.

At least one of pyrene-based compound of Formula 1 above may be used between a pair of electrodes of an OLED. For example, at least one pyrene-based compound of Formula 1 may be used in an emission layer.

Thus, an OLED, according to an embodiment, includes a first electrode, a second electrode opposite the first electrode, and an organic layer between the first electrode and the second electrode, where the organic layer includes at least one pyrene-based compound represented by Formula 1 as described above.

As used herein, the phrase "(an organic layer) includes at least one pyrene-based compound" may be interpreted as "(an organic layer) includes one pyrene-based compound represented by Formula 1 above, or two or more pyrene-based compounds represented by Formula 1 above which are different from each other".

For example, the organic layer may include Compound 1 as the pyrene-based compound. Here, Compound 1 may be present in an emission layer of an OLED. Otherwise, the organic layer may include Compounds 1 and 5 as the pyrene-based compound. Here, Compound 1 and Compound 5 may both be present in the same layer (e.g., Compound 1 and Compound 5 may both be in the emission layer) or may be present in different layers (e.g., Compound 1 may be in the emission layer and Compound 5 may be in the hole transport layer).

The organic layer may include at least one of a hole injection layer (HIL), a hole transport layer (HTL), a functional layer (hereinafter referred to as an "H-functional layer") having hole injection and transport abilities, a buffer layer, an electron blocking layer (EBL), an emission layer (EML), a hole blocking layer (HBL), an electron transport layer (ETL), an electron injection layer (EIL), and a functional layer (hereinafter referred to as an "E-functional layer") having electron transport and injection abilities.

The term "organic layer" used herein refers to a single layer or multiple layers positioned between the first electrode and the second electrode of an OLED.

The organic layer may include an EML and at least one pyrene-based compound represented by Formula 1 may be included in the EML.

The pyrene-based compound included in the EML may serve as a dopant. For example, the pyrene-based compound may serve as a fluorescent dopant. The EML including the pyrene-based compound may emit blue light. Here, the EML may further include a host.

The host may include at least one anthracene-based compound represented by Formulae 400 and 401 below.

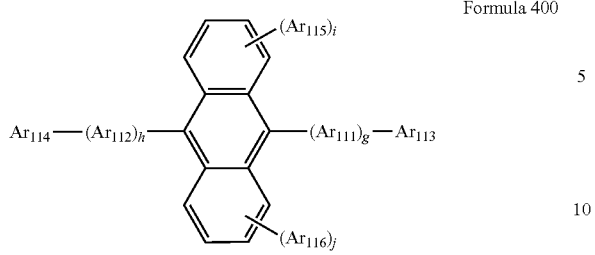

Formula 400

In Formula 400, $Ar_{111}$ and $Ar_{112}$ are each independently a substituted or unsubstituted $C_6$-$C_{60}$ arylene group. $Ar_{113}$ to $Ar_{116}$ are each independently a substituted or unsubstituted $C_1$-$C_{10}$ alkyl group or a substituted or unsubstituted $C_6$-$C_{60}$ aryl group. Also, g, h, i, and j may each independently be an integer of 0 to 4.

For example, in Formula 400, $Ar_{111}$ and $Ar_{112}$ may each independently be one of a phenylene group, a naphthalene group, a phenanthrenylene group, or a pyrenylene group; or a pyrenylene group, a naphthalene group, a phenanthrenylene group, a fluorenyl group, or a pyrenylene group substituted with at least one of a phenyl group, a naphthyl group, or an anthryl group, but are not limited thereto.

In Formula 400, g, h, i, and j may each independently be 0, 1, or 2.

In Formula 400, $Ar_{113}$ to $Ar_{116}$ may each independently be one of a $C_1$-$C_{10}$ alkyl group substituted with at least one of a phenyl group, a naphthyl group, or an anthryl group; a phenyl group; a naphthyl group; an anthryl group; a pyrenyl group; a phenanthrenyl group; a fluorenyl group; a phenyl group, a naphthyl group, an anthryl group, a pyrenyl group, a phenanthrenyl group, or a fluorenyl group substituted with at least one of deuterium, halogen, a hydroxyl group, a cyano group, a nitro group, an amino group, an amidino group, hydrazine, hydrazone, a carboxyl group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a phenyl group, a naphthyl group, an anthryl group, a pyrenyl group, a phenanthrenyl group, or a fluorenyl group; or

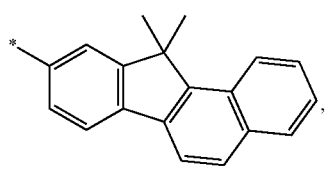 [SMILES: *c1ccc2c(c1)C(C)(C)c1c-2ccc2ccccc12]

but are not limited thereto.

For example, the anthracene-based compound represented by Formula 400 may be one of the compounds below, but is not limited thereto.

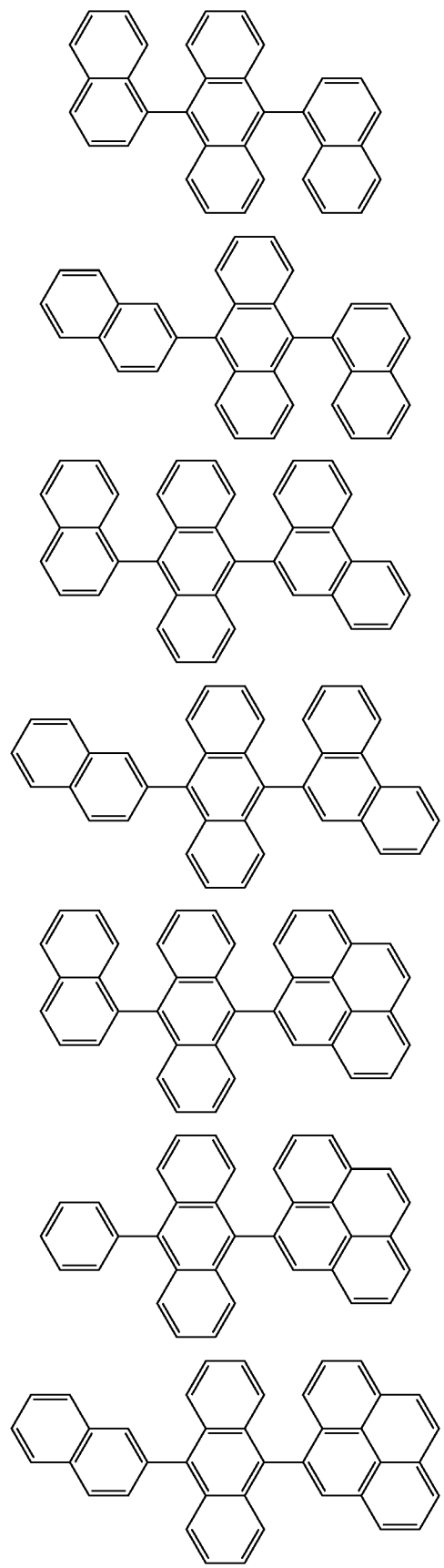

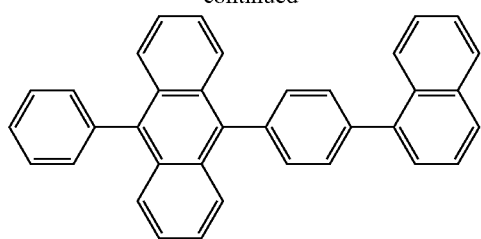
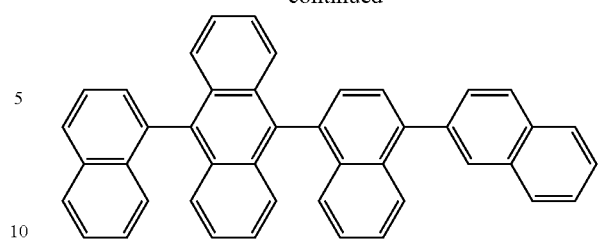
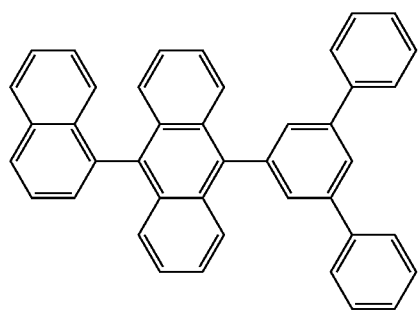
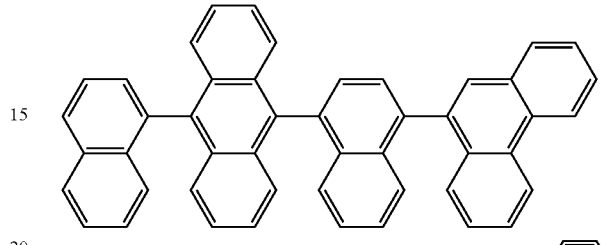
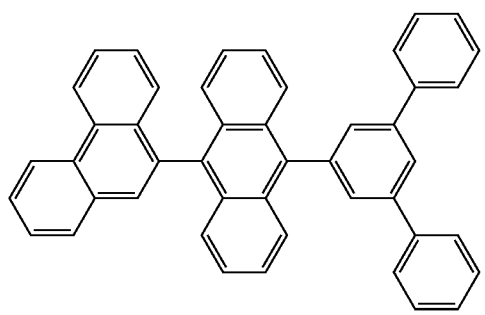
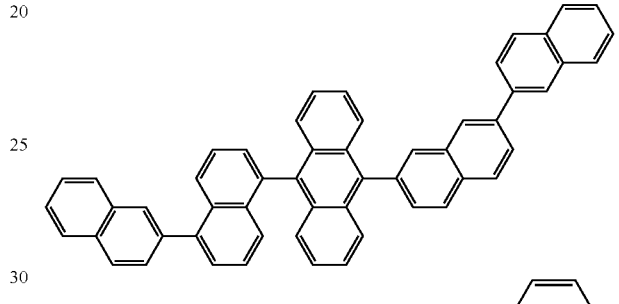
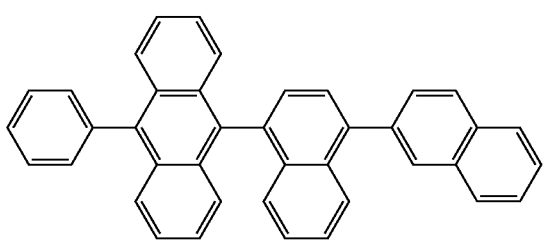
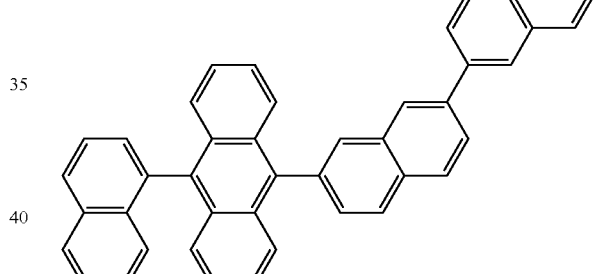
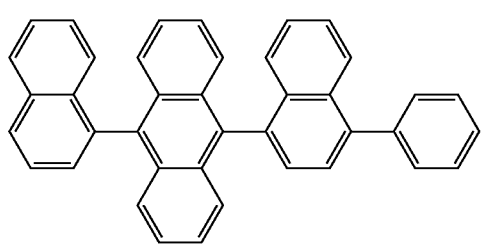
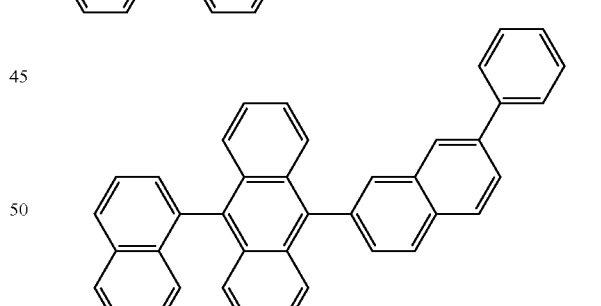
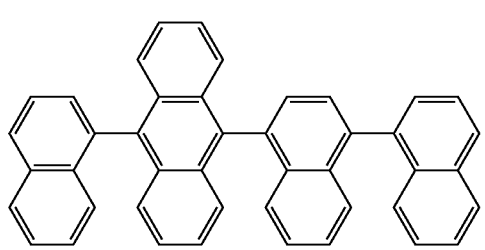
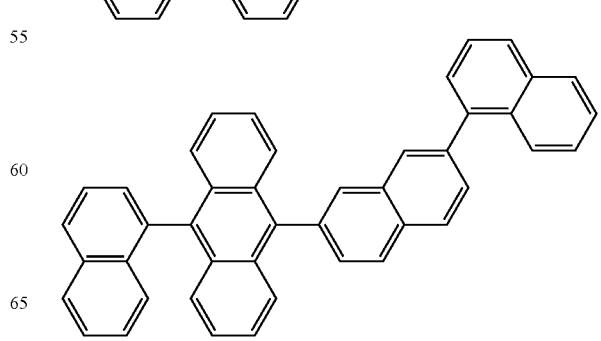

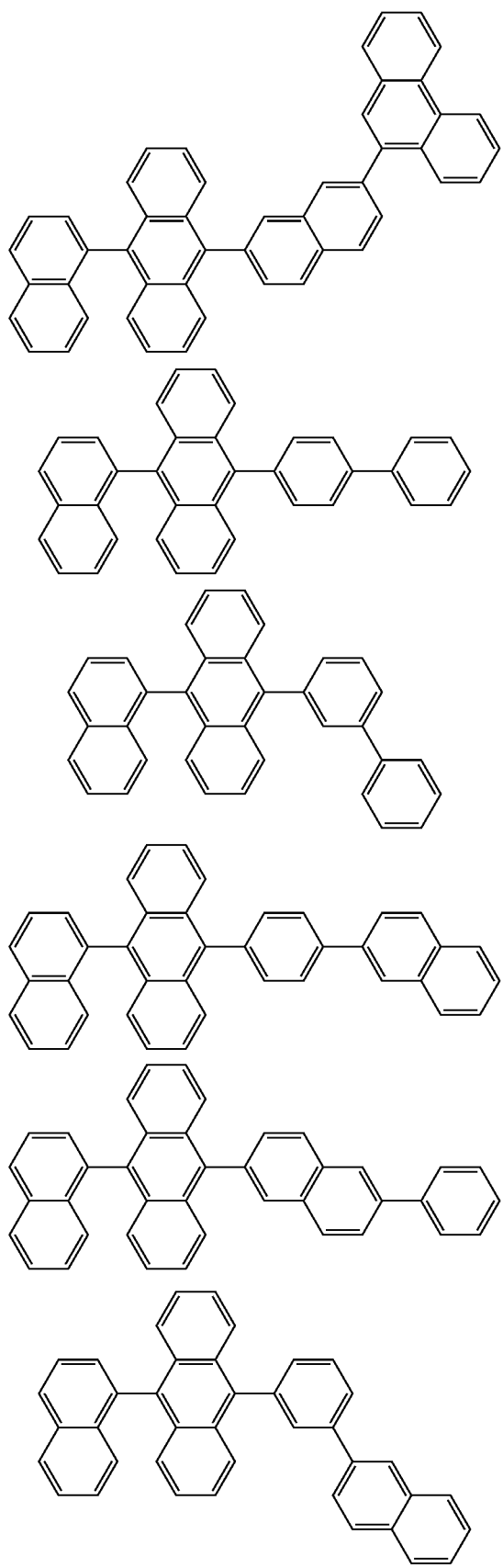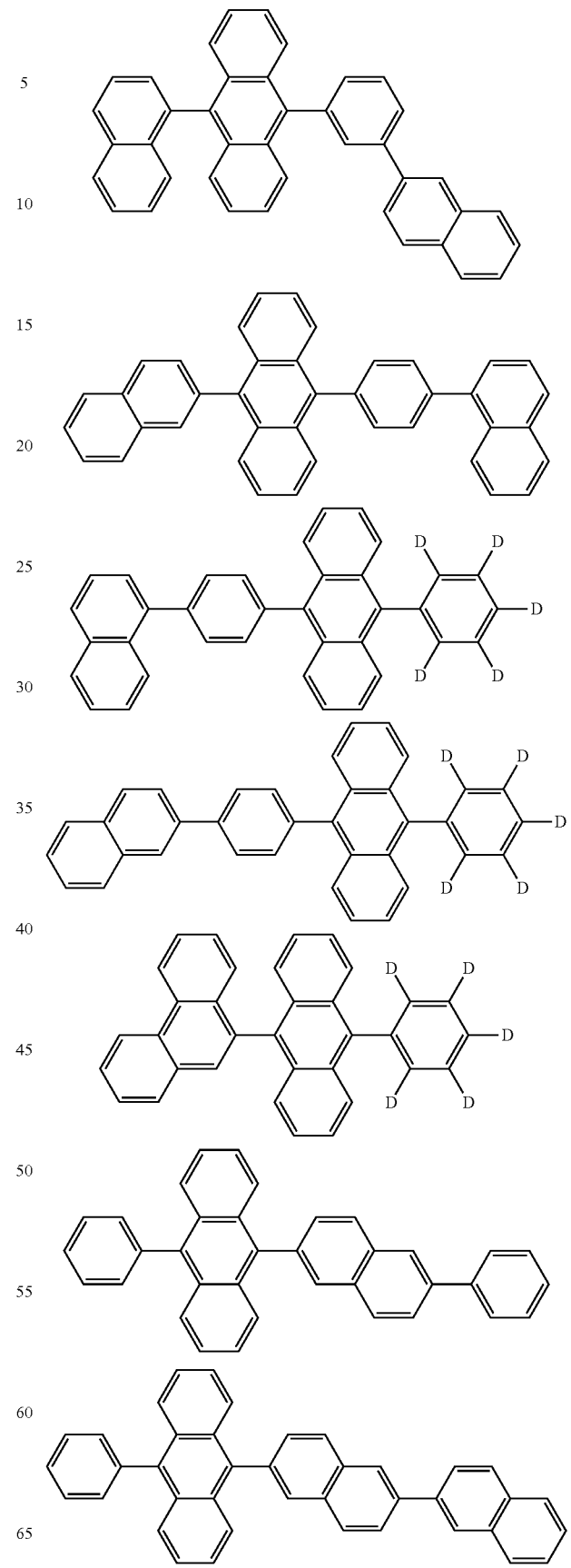

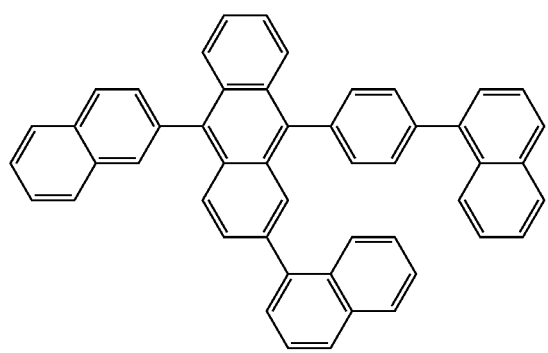
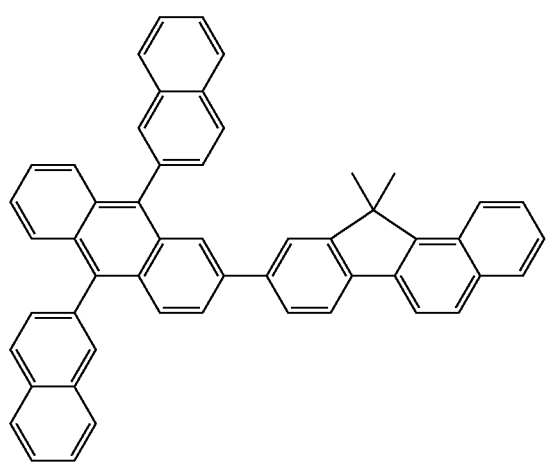
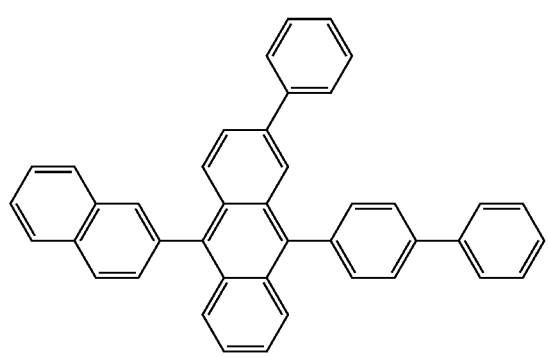
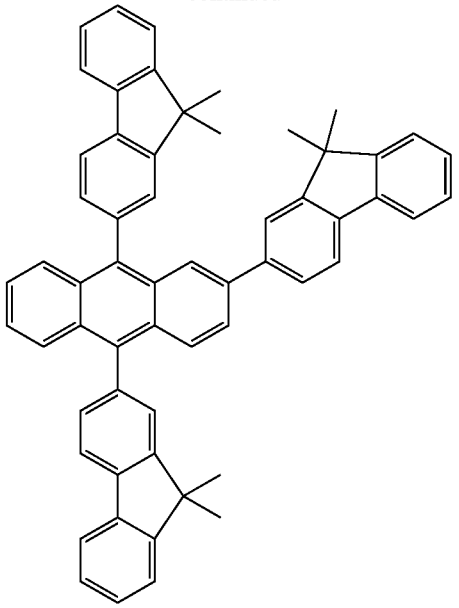
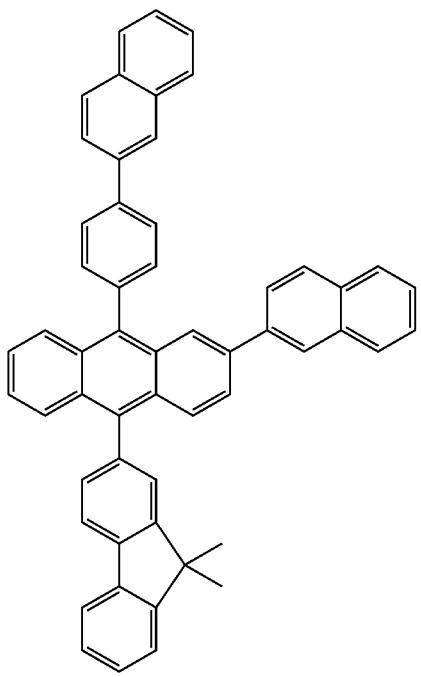
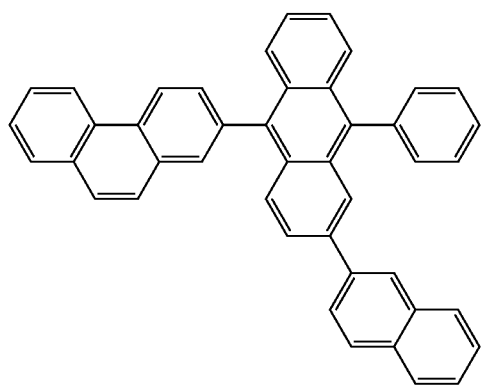

Formula 401

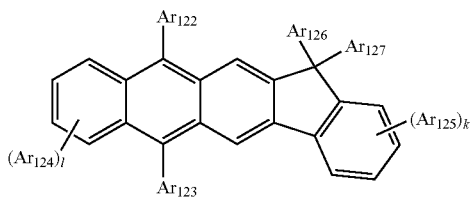

In Formula 401, $Ar_{122}$ to $Ar_{125}$ are the same as $Ar_{113}$ of Formula 400, described above.

In Formula 401, $Ar_{126}$ and $Ar_{127}$ may each independently be a $C_1$-$C_{10}$ alkyl group (e.g., a methyl group, an ethyl group, or a propyl group).

In Formula 401, k and l may each independently be an integer of 0 to 4. For example, each of k and l may be 0, 1, or 2.

For example, the anthracene-based compound represented by Formula 401 may be one of the compounds below, but is not limited thereto.

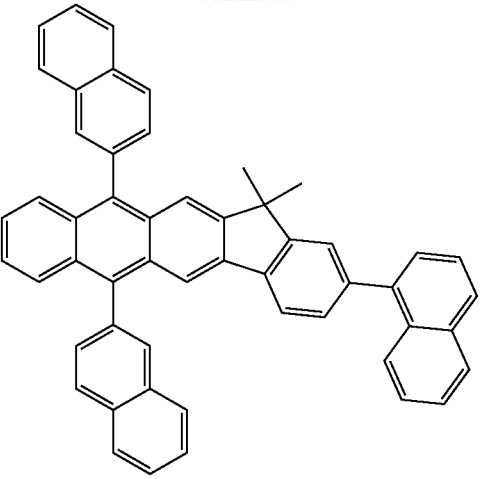

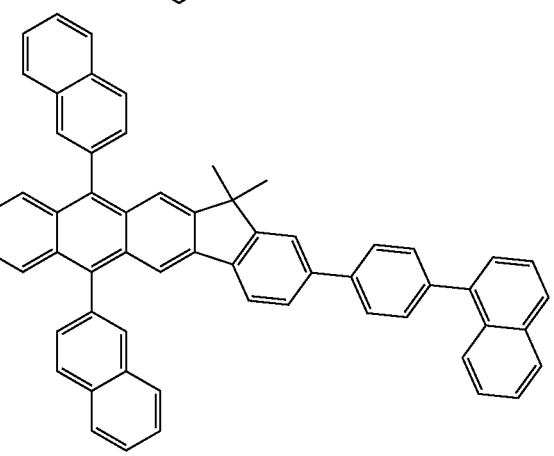

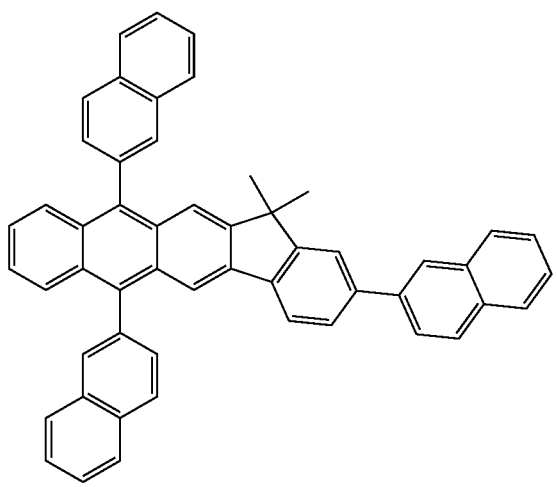

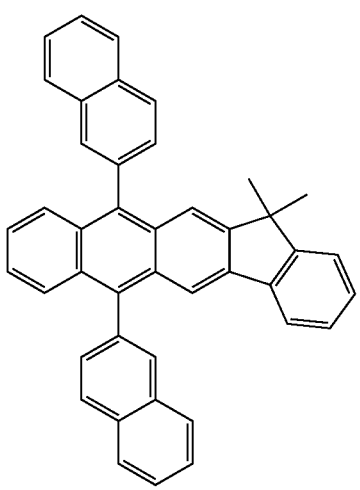

An OLED including the pyrene-based compound represented by Formula I may emit blue light that satisfies the sRGB standard, and the OLED may be used in a large-scale full color display (e.g., an OLED TV, etc.).

FIG. 1 is a schematic cross-sectional view of an OLED 10 according to an embodiment of the present invention. Hereinafter, a structure of the OLED 10 and a method of manufacturing the OLED 10 according to embodiments of the present invention will be described with reference to FIG. 1.

The substrate 11 may be any substrate generally used in OLEDs, and may be, for example, a glass substrate or a transparent plastic substrate having good mechanical strength, thermal stability, transparency, surface smoothness, ease of handling, and waterproofness.

A first electrode 13 may be formed by applying a first electrode material on the substrate 11 by deposition or sputtering. When the first electrode 13 is an anode, the first electrode material may be selected from materials having a high work function so as to facilitate hole injection. The first electrode 13 may be a reflective electrode or a transparent electrode. For example, when the OLED 10 is used in a large-scale display, the first electrode 13 may be a reflective electrode or a transparent electrode. Examples of the first electrode material may include indium-tin oxide (ITO), indium-zinc oxide (IZO), tin oxide ($SnO_2$), and zinc oxide (ZnO). Also, when magnesium (Mg), aluminum (Al), aluminum-lithium (Al—Li), calcium (Ca), magnesium-indium (Mg—In), or magnesium-silver (Mg—Ag) is used as the first electrode material, the first electrode 13 may be formed as a reflective electrode.

The first electrode 13 may have a single layer or two or more layers. For example, the first electrode 13 may have a three-layered structure of ITO/Ag/ITO, but is not limited thereto.

An organic layer 15 is formed on the first electrode 13.

The organic layer 15 may include a HIL, a HTL, a buffer layer, an EML, an ETL, and an EIT.

The HIL may be formed on the first electrode 13 using various methods, such as vacuum deposition, spin coating, casting, or LB deposition.

When the HIL is formed by vacuum deposition, the deposition conditions may vary according to the compound used as the material for forming the HIL, the structure of the desired HIL, and the thermal characteristics. For example, the deposition conditions may include, but are not limited to, a deposition temperature of about 100 to about 500° C., a degree of vacuum of about $10^{-8}$ to about $10^{-3}$ torr, and a deposition speed of about 0.01 to about 100 Å/sec.

When the HIL is formed by spin coating, the coating conditions may vary according to the compound used as the material for forming the HIL, the structure of the desired HIL, and the thermal characteristics. For example, the coating conditions may include, but are not limited to, a coating speed of about 2,000 to about 5,000 rpm and a heat treatment temperature for removing solvent after coating of about 80 to about 200° C.

The material for forming the HIL may be a known hole injection material. Examples of the hole injection material include, but are not limited to, N,N'-diphenyl-N,N'-bis-[4-(phenyl-m-tolyl-amino)-phenyl]-biphenyl-4,4'-diamine (DNTPD), a phthalocyanine compound such as copper phthalocyanine, 4,4',4''-tris (3-methylphenylphenylamino)triphenylamine (m-MTDATA), N,N'-di(1-naphthyl)-N,N'-diphenylbenzidine(NPB), 4,4'4''-tris(N,N-diphenylamino) triphenylamine (TDATA), 4,4', 4''-tris{N,-(2-naphthyl)-N-phenylamino}-triphenylamine (2-TNATA), Polyaniline/Dodecylbenzenesulfonic acid (Pani/DBSA), Poly(3,4-ethylenedioxythiophene)/Poly(4-styrenesulfonate) (PEDOT/PSS), Polyaniline/Camphor sulfonicacid (Pani/CSA), or Polyaniline/Poly(4-styrenesulfonate) (PANI/PSS).

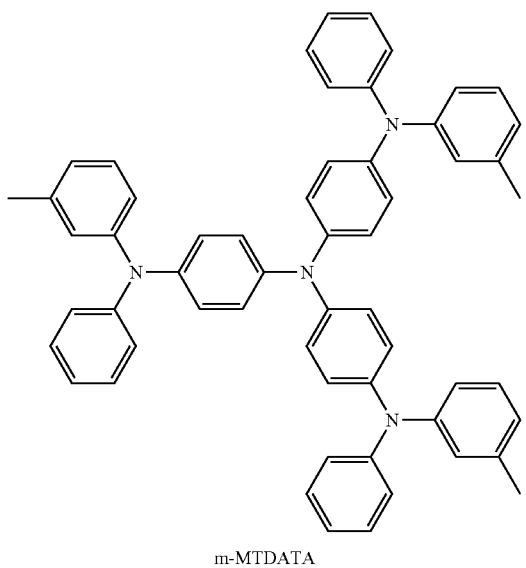

m-MTDATA

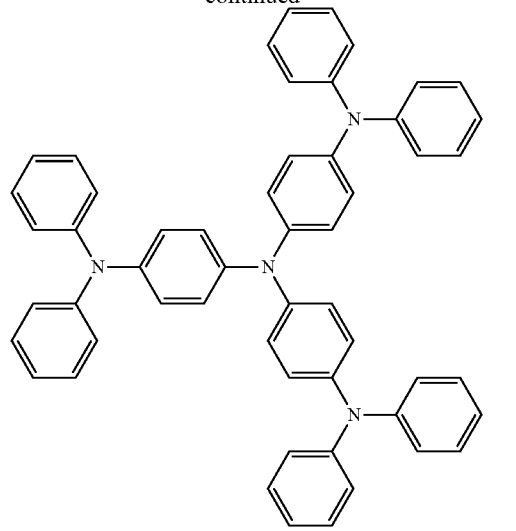

TDATA

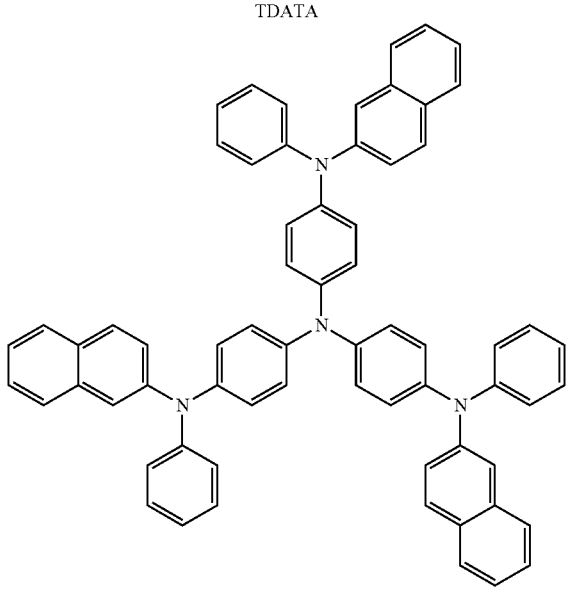

2-TNATA

The thickness of the HIL may be in a range of about 100 Å to about 10,000 Å, for example, in a range of about 100 Å to about 1,000 Å. When the thickness of the HIL is within these ranges, satisfactory hole injection properties may be obtained without a substantial increase in driving voltage.

Next, the HTL may be formed on the HIL using various methods, such as vacuum deposition, spin coating, casting, or LB deposition. When the HTL is formed by vacuum deposition or spin coating, the deposition or coating conditions may vary according to the compound used. However, in general, the conditions may be similar to the conditions described above with respect to formation of the HIL.

A material for forming the HTL may be any known hole transporting material. Examples of the hole transporting material include, but are not limited to, carbazole derivatives such as N-phenylcarbazole, polyvinylcarbazole, or the like, N,N'-bis(3-methylphenyl)-N,N'-diphenyl-[1,1-biphenyl]-4, 4'-diamine (TPD), 4,4',4''-tris(N-carbazolyl)triphenylamine (TCTA), N,N'-Bis(naphthalene-1-yl)-N,N'-bis(phenyl)-2,2'-dimethylbenzidine (a-NPD), or the like.

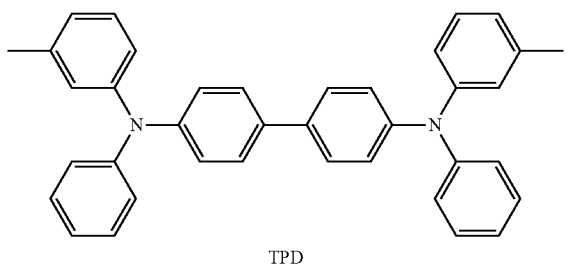

TPD

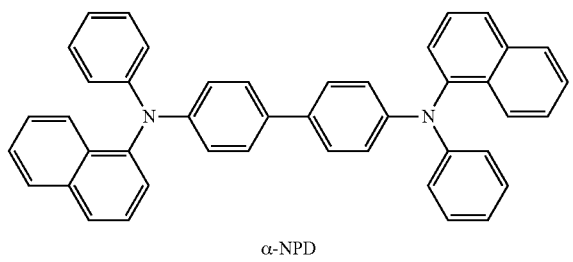

α-NPD

A thickness of the HTL may be in a range of about 50 Å to about 2,000 Å, for example, in a range of about 100 Å to about 1,500 Å. When the thickness of the HTL is within these ranges, satisfactory hole transport properties may be obtained without a substantial increase in driving voltage.

The H-functional layer (which is a functional layer having hole injection and transport abilities) may include one or more of the HIL materials described above and the HTL materials. The thickness of the H functional layer may be in a range of about 50 Å to about 10,000 Å, for example, in a range of about 100 Å to about 1,000 Å. When the thickness of the H-functional layer is within these ranges, satisfactory hole injection and transport properties may be obtained without a substantial increase in driving voltage.

Meanwhile, at least one of the HIL, HTL, and the H-functional layer may further include at least one of the compounds represented by Formulae 300 and 350.

Formula 300

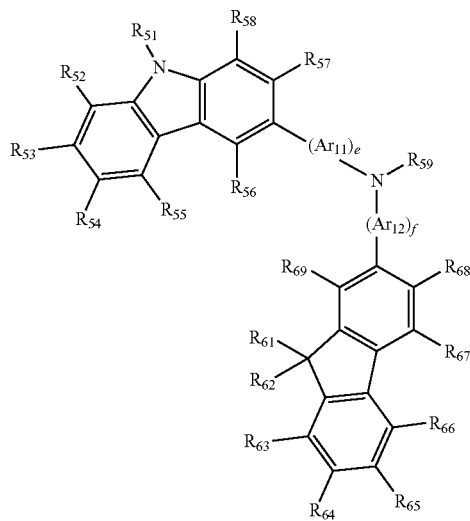

Formula 350

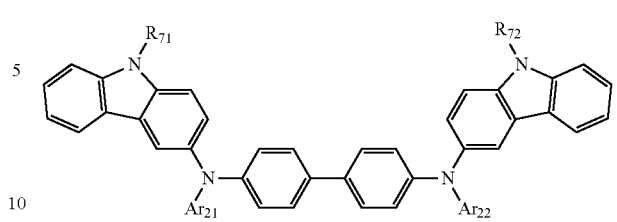

In Formula 300, $Ar_{11}$ and $Ar_{12}$ are each independently a substituted or unsubstituted $C_6$-$C_{60}$ arylene group. When $Ar_{11}$ and $Ar_{12}$ are each independently a substituted $C_6$-$C_{60}$ arylene group, at least one substituent of the substituted $C_6$-$C_{60}$ arylene group may be selected from deuterium; a halogen; a hydroxyl group; a cyano group; a nitro group; an amino group; an amidino group; hydrazine; hydrazone; a carboxyl group or a salt thereof; a sulfonic acid group or a salt thereof; a phosphoric acid group or a salt thereof; a $C_1$-$C_{10}$ alkyl group; a $C_1$-$C_{10}$ alkoxy group; a phenyl group, a naphthyl group, a fluorenyl group, a phenanthrenyl group, an anthryl group, a triphenylenyl group, a pyrenyl group, a chrysenyl group, an imidazolyl group, an imidazolynyl group, an imidazopyridinyl group, an imidazopyrimidinyl group, a pyridinyl group, a pyrizinyl group, a pyrimidinyl group, or an indolyl group; or a phenyl group, a naphthyl group, a fluorenyl group, a phenanthrenyl group, an anthryl group, a triphenylenyl group, a pyrenyl group, a chrysenyl group, an imidazolyl group, an imidazolynyl group, an imidazopyridinyl group, an imidazopyrimidinyl group, a pyridinyl group, a pyrizinyl group, a pyrimidinyl group, or an indolyl group substituted with at least one of deuterium, a halogen, a hydroxyl group, a cyano group, a nitro group, an amino group, an amidino group, hydrazine, hydrazone, a carboxyl group or a salt thereof, a sulfonic acid group or a salt thereof, a phosphoric acid group or a salt thereof, a $C_1$-$C_{10}$ alkyl group, or a $C_1$-$C_{10}$ alkoxy group.

$Ar_{11}$ and $Ar_{12}$ may each independently be a substituted or unsubstituted phenylene group, a substituted or unsubstituted pentalenylene group, a substituted or unsubstituted indenylene group, a substituted or unsubstituted naphthylene group, a substituted or unsubstituted azulenylene group, a substituted or unsubstituted heptalenylene group, a substituted or unsubstituted indacenylene group, a substituted or unsubstituted acenaphthylene group, a substituted or unsubstituted fluorenylene group, a substituted or unsubstituted phenalenylene group, a substituted or unsubstituted phenanthrenylene group, a substituted or unsubstituted anthrylene group, a substituted or unsubstituted fluoranthenylene group, a substituted or unsubstituted triphenylenylene group, a substituted or unsubstituted pyrenylene group, a substituted or unsubstituted chrysenylene group, a substituted or unsubstituted naphthacenylene group, a substituted or unsubstituted pycenylene group, a substituted or unsubstituted perylenylene group, a substituted or unsubstituted pentacenylene group, or a substituted or unsubstituted hexacenylene group.

For example, $Ar_{11}$ and $Ar_{12}$ may each independently be a substituted or unsubstituted phenylene group, a substituted or unsubstituted naphthylene group, a substituted or unsubstituted fluorenylene group, or a substituted or unsubstituted phenanthrenylene group, but are not limited thereto.

In Formula 350 above, $Ar_{21}$ and $Ar_{22}$ may each independently be a substituted or unsubstituted $C_6$-$C_{60}$ aryl group or a substituted or unsubstituted $C_2$-$C_{60}$ heteroaryl group. For example, $Ar_{21}$ and $Ar_{22}$ may each independently be a substituted or unsubstituted phenyl group, a substituted or unsubstituted naphthyl group, a substituted or unsubstituted phenanthrenyl group, a substituted or unsubstituted anthryl group, a substituted or unsubstituted pyrenyl group, a substituted or unsubstituted chrysenyl group, a substituted or unsubstituted fluorenyl group, a substituted or unsubstituted carbazolyl group, a substituted or unsubstituted dibenzofuranyl group, or a substituted or unsubstituted dibenzothiophenyl group. In this case, at least one of the substituents of the substituted phenyl group, the substituted naphthyl group, the substituted phenanthrenyl group, the substituted anthryl group, the substituted pyrenyl group, the substituted chrysenyl group, the substituted fluorenyl group, the substituted carbazolyl group, the substituted dibenzofuranyl group, or the substituted dibenzothiophenyl group may be selected from deuterium; a halogen atom; a hydroxyl group; a cyano group; a nitro group; an amino group; an amidino group; hydrazine; hydrazone; a carboxyl group or a salt thereof; a sulfonic acid group or a salt thereof; a phosphoric acid or a salt thereof; a $C_1$-$C_{10}$ alkyl group; a $C_1$-$C_{10}$ alkoxy group; a phenyl group, a naphthyl group, a fluorenyl group, a phenanthrenyl group, an anthryl group, an triphenylenyl group, a pyrenyl group, a chrysenyl group, an imidazolyl group, an imidazolinyl group, an imidazopyridinyl group, an imidazopyrimidinyl group, a pyridinyl group, a pyrazinyl group, a pyrimidinyl group, or an indolyl group; or a phenyl group, a naphthyl group, a fluorenyl group, a phenanthrenyl group, an anthryl group, an triphenylenyl group, a pyrenyl group, a chrysenyl group, an imidazolyl group, an imidazolinyl group, an imidazopyridinyl group, an imidazopyrimidinyl group, a pyridinyl group, a pyrazinyl group, a pyrimidinyl group, or an indolyl group substituted with at least one of deuterium, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid or a salt thereof, a $C_1$-$C_{10}$ alkyl group, or a $C_1$-$C_{10}$ alkoxy group.

In Formula 300, e and f may each independently be an integer of 0 to 5, for example, 0, 1, or 2. For example, e may be 1 and f may be 0, but the present disclosure is not limited thereto.

In Formula 300, $R_{51}$ to $R_{58}$, $R_{61}$ to $R_{69}$, $R_{71}$, and $R_{72}$ may each independently be one of hydrogen, deuterium, a halogen, a hydroxyl group, a cyano group, a nitro group, an amino group, an amidino group, hydrazine, hydrazone, a carboxyl group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_5$-$C_{60}$ aryl group, a substituted or unsubstituted $C_5$-$C_{60}$ aryloxy group, or a substituted or unsubstituted $C_5$-$C_{60}$ arylthio group. For example, $R_{51}$ to $R_{58}$, $R_{61}$ to $R_{69}$, $R_{71}$, and $R_{72}$ may each independently be hydrogen; deuterium; a halogen; a hydroxyl group; a cyano group; a nitro group; an amino group; an amidino group; hydrazine; hydrazone; a carboxyl group or a salt thereof; a sulfonic acid group or a salt thereof; a phosphoric acid group or a salt thereof; a $C_1$-$C_{10}$ alkyl group (e.g., a methyl group, an ethyl group, a propyl group, a butyl group, a pentyl group, a hexyl group, etc.); a $C_1$-$C_{10}$ alkoxy group (e.g., a methoxy group, an ethoxy group, a propoxy group, a butoxy group, a pentoxy group, etc.); a $C_1$-$C_{10}$ alkyl group or a $C_1$-$C_{10}$ alkoxy group substituted with at least one of deuterium, a halogen, a hydroxyl group, a cyano group, a nitro group, an amino group, an amidino group, hydrazine, hydrazone, a carboxyl group or a salt thereof, a sulfonic acid group or a salt thereof, or a phosphoric acid group or a salt thereof; a phenyl group; a naphthyl group; an anthryl group; a fluorenyl group; a pyrenyl group; a phenyl group, a naphthyl group, an anthryl group, a fluorenyl group, or a pyrenyl group substituted with at least one of deuterium, a halogen, a hydroxyl group, a cyano group, a nitro group, an amino group, an amidino group, hydrazine, hydrazone, a carboxyl group or a salt thereof, a sulfonic acid group or a salt thereof, a phosphoric acid group or a salt thereof, a $C_1$-$C_{10}$ alkyl group, and a $C_1$-$C_{10}$ alkoxy group, but is not limited thereto.

In Formula 300, $R_{59}$ may be one of a phenyl group; a naphthyl group; an anthryl group; a biphenyl group; a pyridyl group; or a phenyl group, a naphthyl group, an anthryl group, a biphenyl group, or a pyridyl group substituted with at least one of deuterium, a halogen, a hydroxyl group, a cyano group, a nitro group, an amino group, an amidino group, hydrazine, hydrazone, a carboxyl group or a salt thereof, a sulfonic acid group or a salt thereof, a phosphoric acid group or a salt thereof, a substituted or unsubstituted $C_1$-$C_{20}$ alkyl group, or a substituted or unsubstituted $C_1$-$C_{20}$ alkoxy group.

According to an embodiment, the compound represented by Formula 300 may be represented by Formula 300A below, but is not limited thereto.

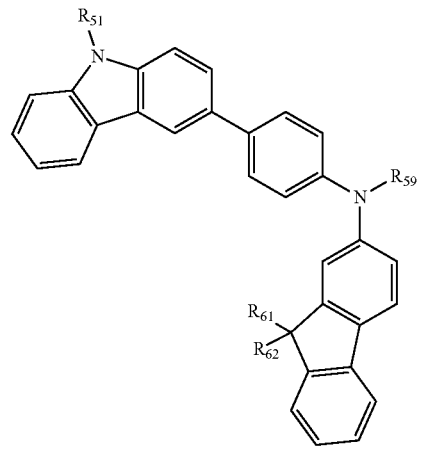

Formula 300A

In Formula 300A, $R_{51}$, $R_{60}$, $R_{61}$ and $R_{59}$ are as described above.

For example, at least one of the HIL, the HTL, or the H-functional layer may include one or more of Compounds 301 to 320 below, but the present disclosure is not limited thereto 301
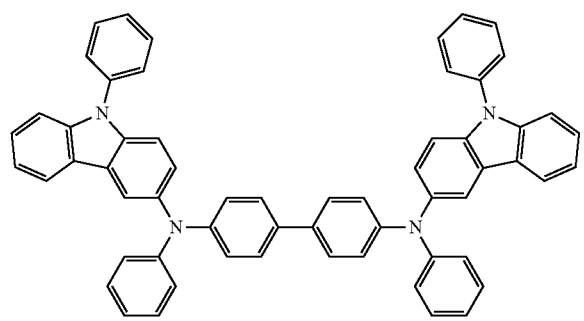
302
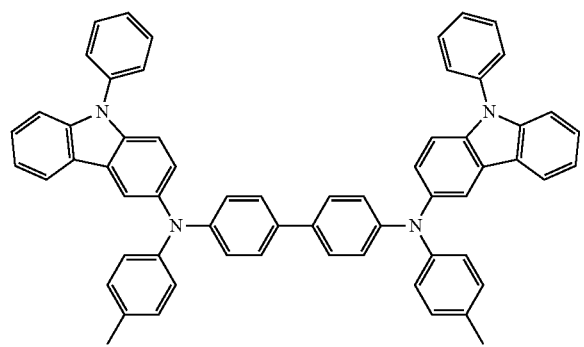
303
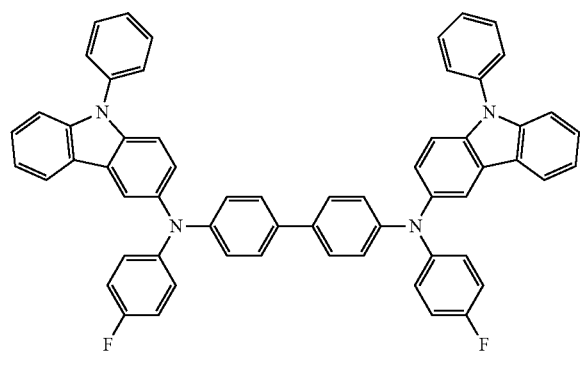
304
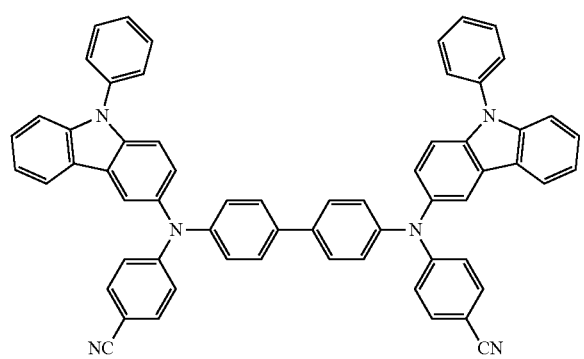
305
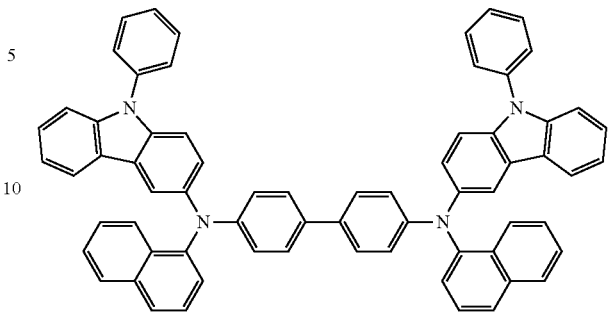
306
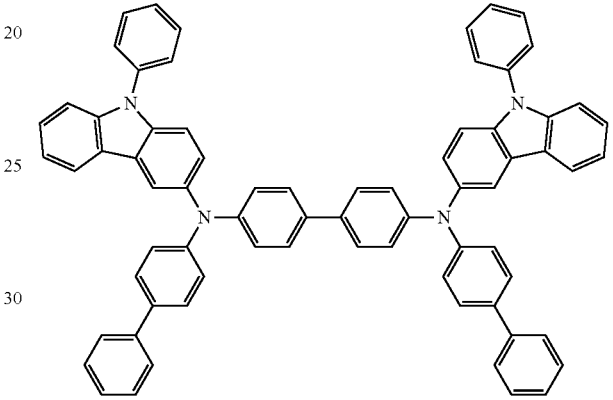
307
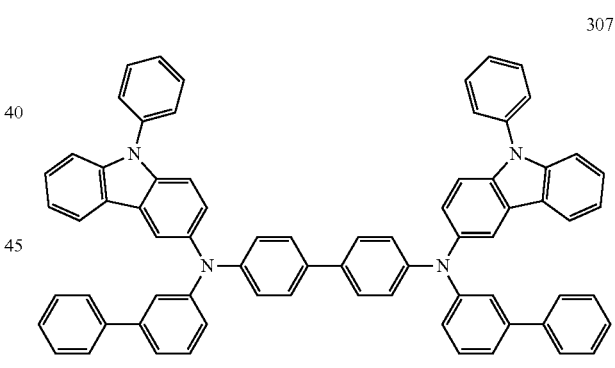
308
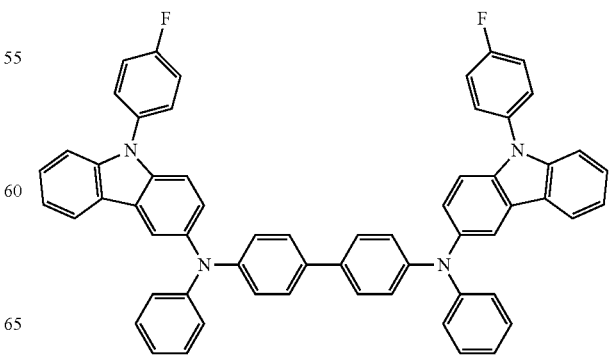

309
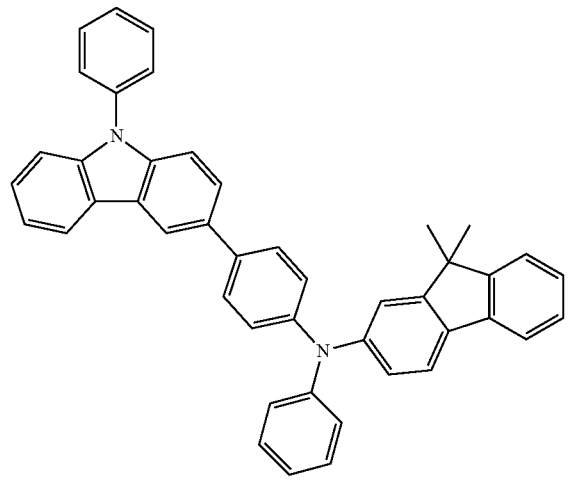
310
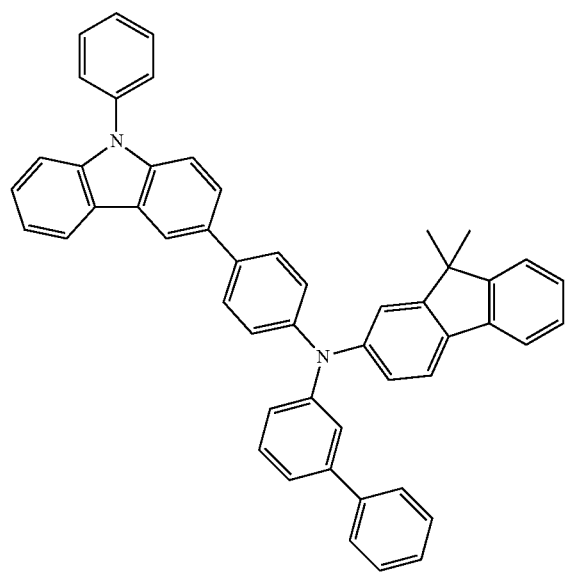
311
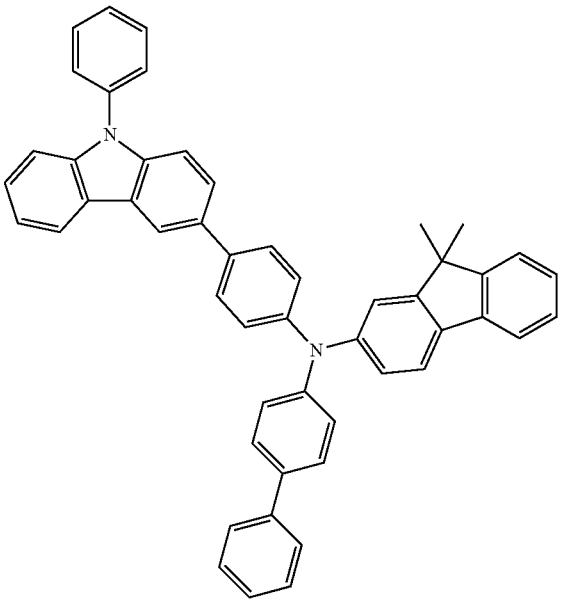
312
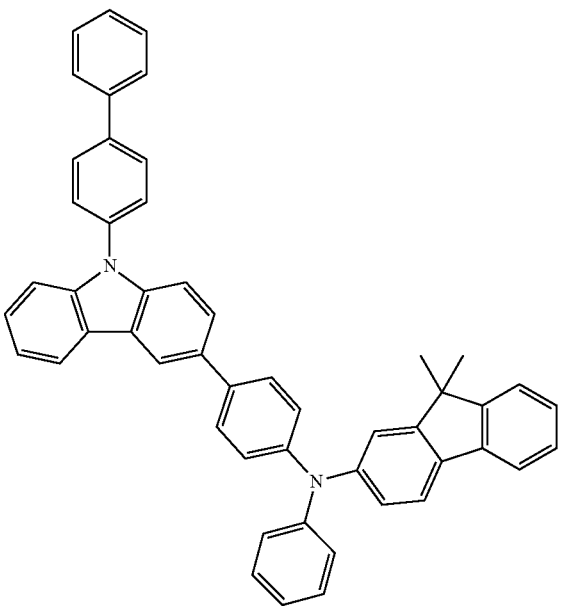

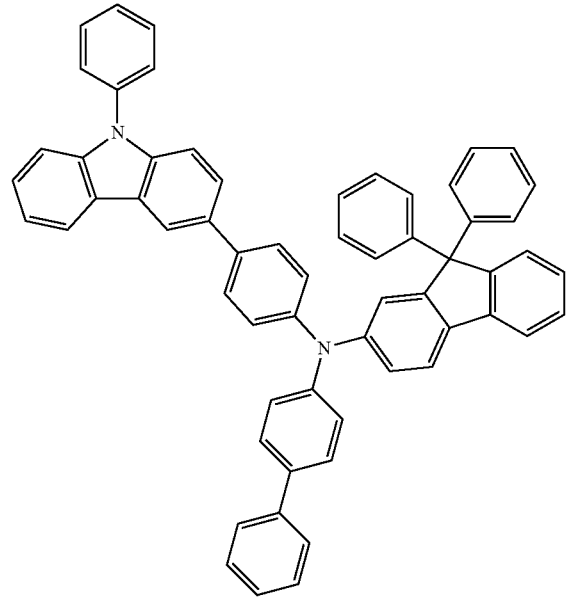
313
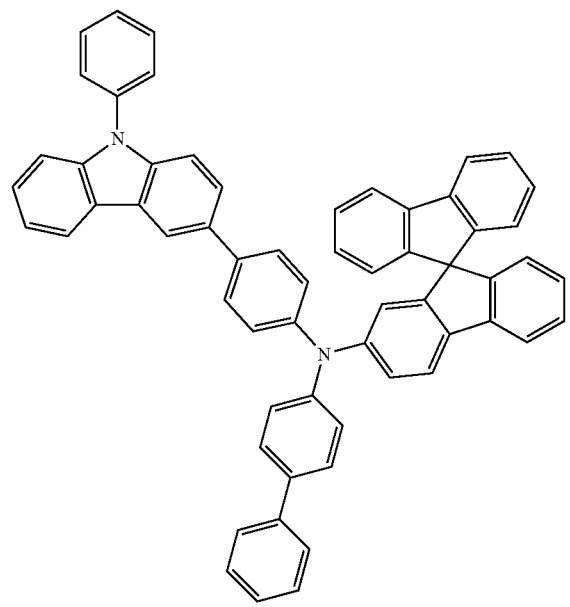
314
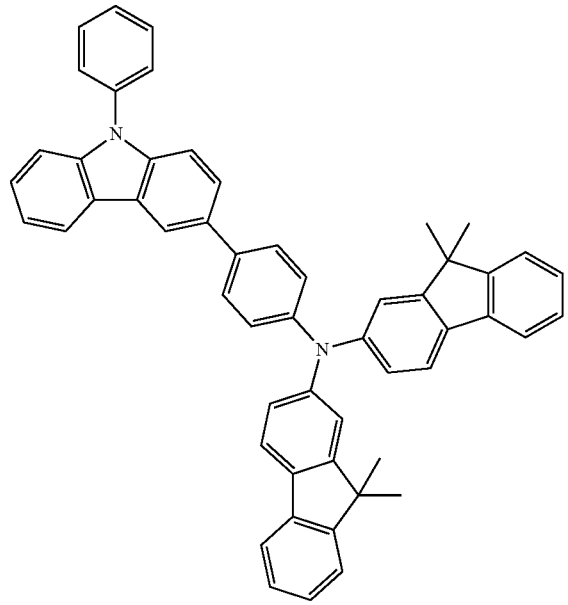
315
316
317

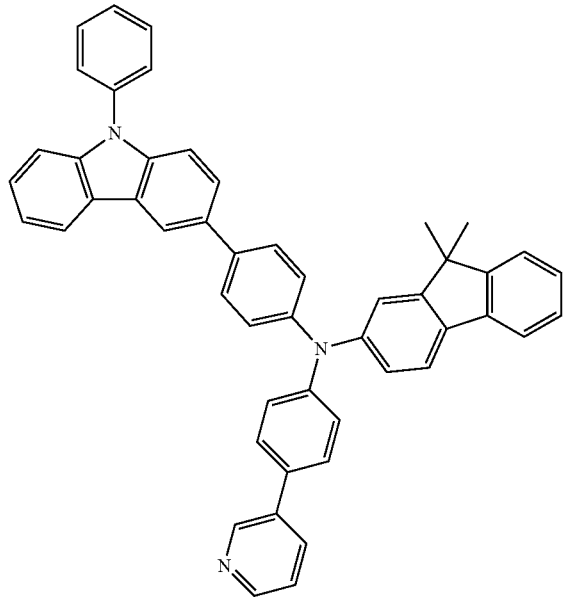

318

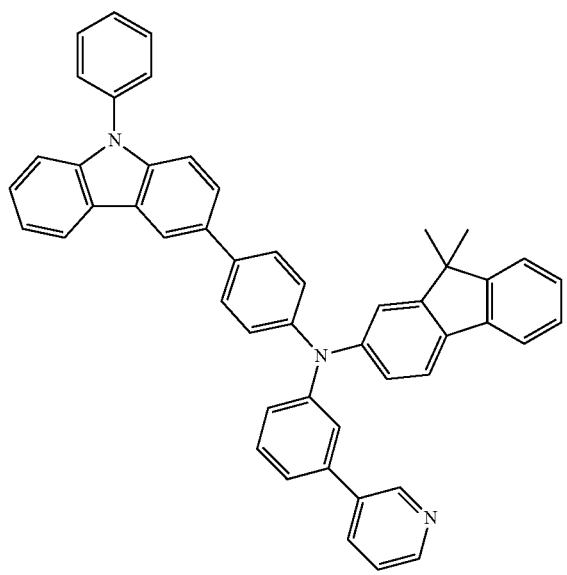

319

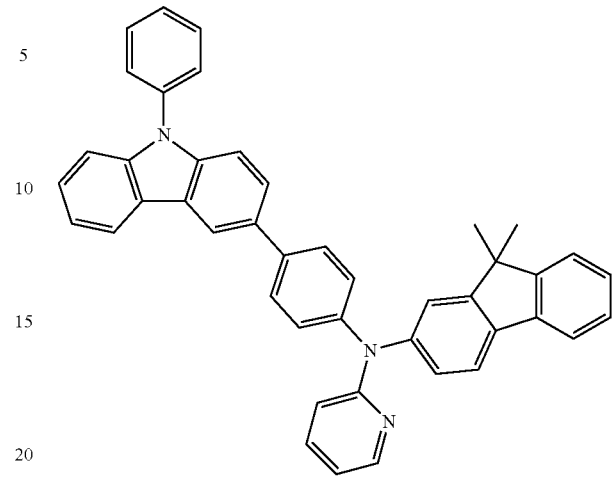

320

At least one of the HIL, the HTL, or the H-functional layer may further include a charge-generating material in order to improve the conductivity of the layer in addition to the hole injection material, the hole transport material, and/or the material having hole injection and hole transport functions.

The charge-generating material may be, for example, a p-dopant. Examples of the p-dopant may include, but are not limited to, quinone derivatives such as tetracyanoquinodimethane (TCNQ), and 2,3,5,6-tetrafluoro-tetracyano-1,4-benzoquinodimethane (F4-TCNQ); metal oxides such as tungsten oxides and molybdenum oxides; and cyano-containing compounds such as Compound 200 below and the like.

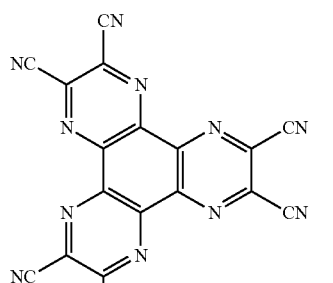

Compound 200

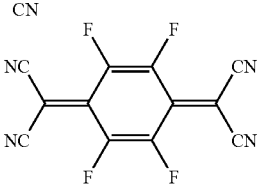

F4-TCNQ

When the HIL, the HTL, or the H-functional layer further includes the charge-generating material, the charge-generating material may be homogeneously or inhomogeneously dispersed in the layer.

A buffer layer may be disposed between at least one of the HIL, the HTL, or the H-functional layer and the EML. The buffer layer may serve to improve efficiency by compensating for the optical resonance distance according to the wavelength of the light emitted from the EML. The buffer layer may include the hole injection material and the hole transport material. Otherwise, the buffer layer may include the same material included in the HIL, the HTL, or the H-functional layer (formed under the buffer layer).

Subsequently, the EML may be formed on the HTL, the H-functional layer, or the buffer layer using various methods such as vacuum deposition, spin coating, casting, or LB deposition. When the EML is formed by vacuum deposition or spin coating, the deposition or coating conditions may vary according to the compound used. However, in general, the conditions may be similar to the conditions described above with respect to formation of the HIL.

The EML may include at least one pyrene-based compound represented by Formula 1.

The pyrene-based compound included in the EML may serve as a dopant (e.g., a blue fluorescent dopant). Here, the EML may further include a host as well as the pyrene-based compound.

Examples of the host may include, but are not limited to, Alq$_3$, 4,4'-N,N'-dicarbazole-biphenyl (CBP), poly(n-vinylcarbazole) (PVK), 9,10-di(naphthalene-2-yl)anthracene (ADN), TCTA, 1,3,5-tris(N-phenylbenzimidazole-2-yl)benzene (TPBI), 3-tert-butyl-9,10-di(naphth-2-yl) anthracene (TBADN), E3, distyrylarylene (DSA), dmCBP (refer to Formula below) and Compounds 501 through 509 below.

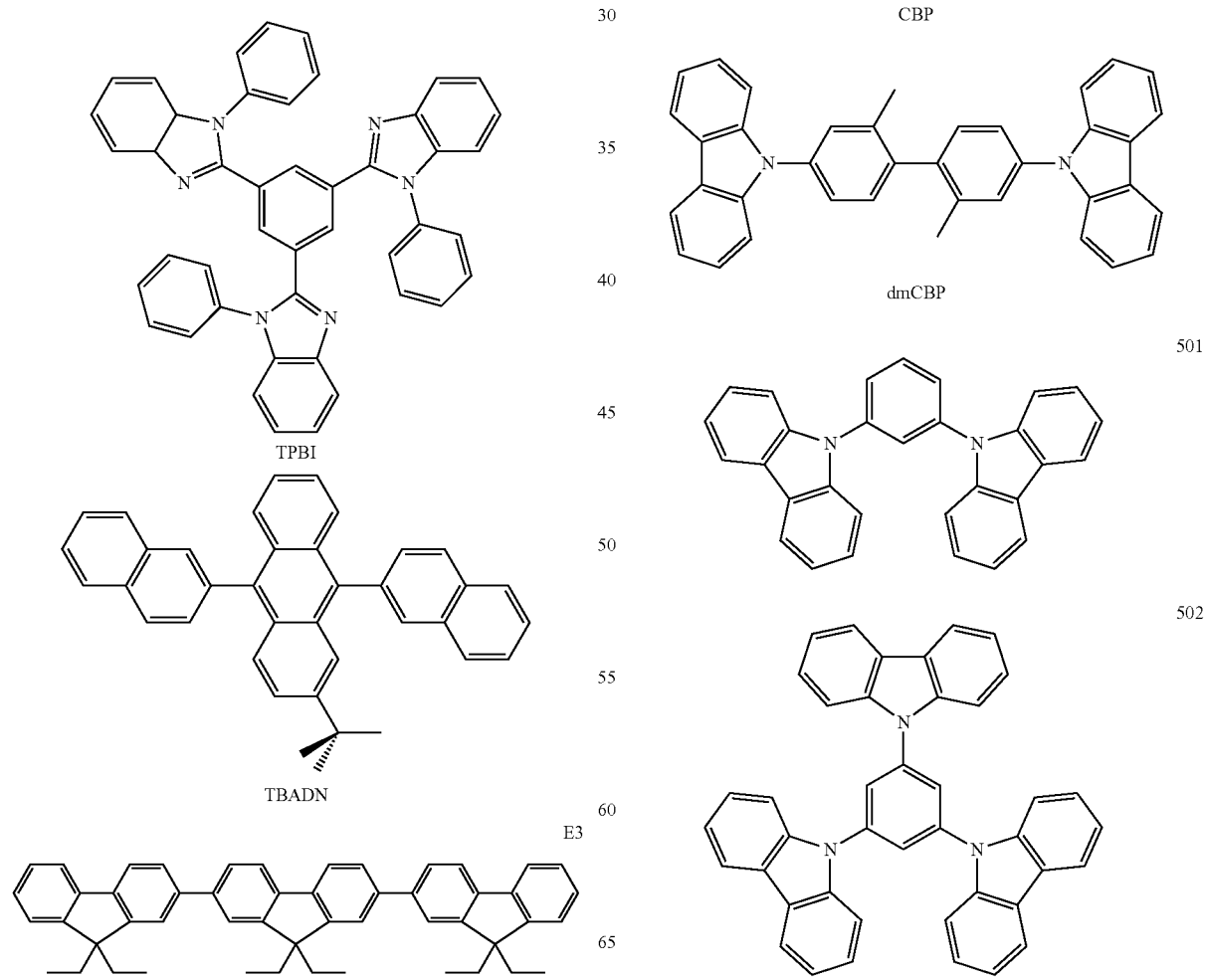

503
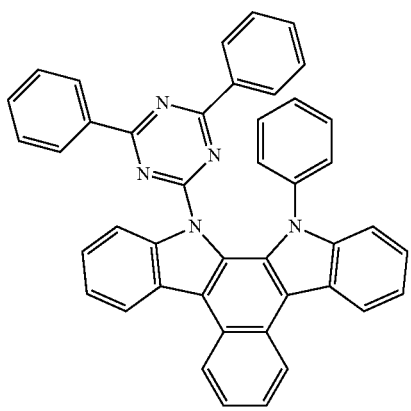
504
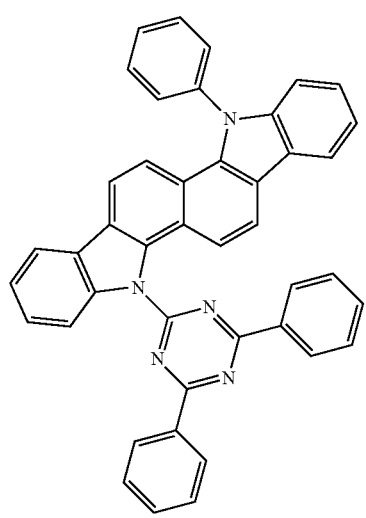
505
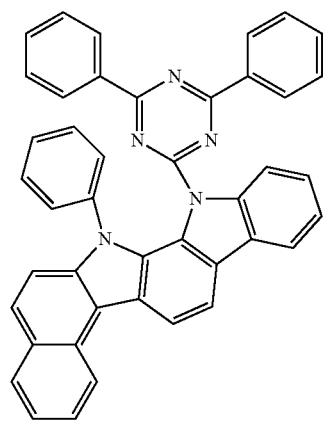
506
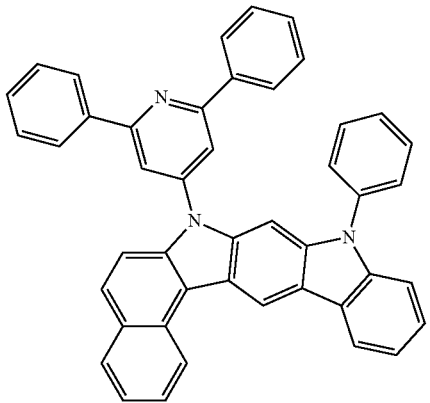
507
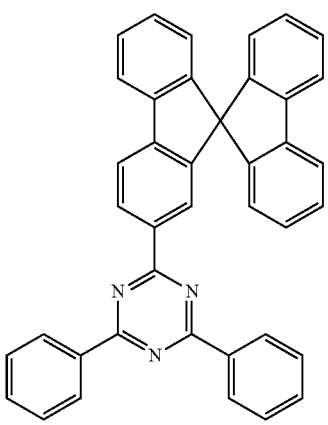
508
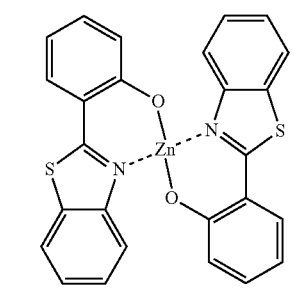
509
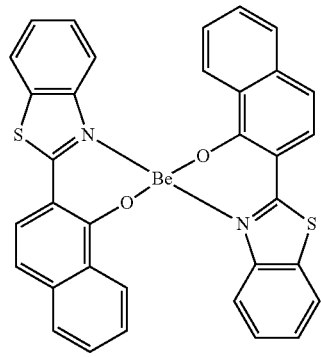

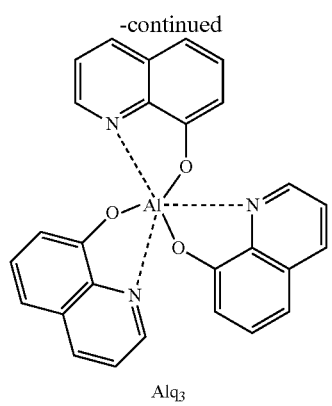

Alq₃

Alternatively, the host may include one or more of the anthracene-based compounds represented by Formulae 400 and 401 described above.

The OLED may include blue subpixels for emitting blue light, green subpixels for emitting green light, and red subpixels for emitting red light. The blue subpixels may include a blue EML for emitting blue light, and the blue EML may include the pyrene-based compound represented by Formula 1 as described above.

Meanwhile, the blue EML may include one or more of the compounds below as a blue dopant, but the present disclosure is not limited thereto.

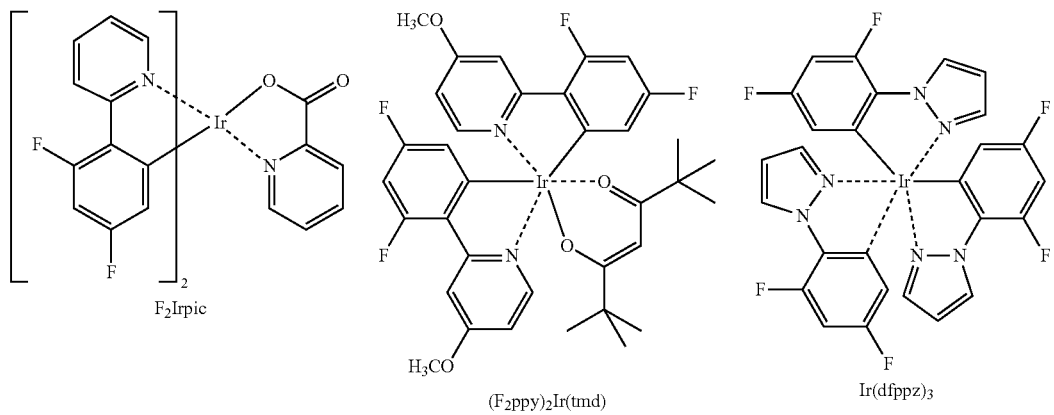

F₂Irpic    (F₂ppy)₂Ir(tmd)    Ir(dfppz)₃

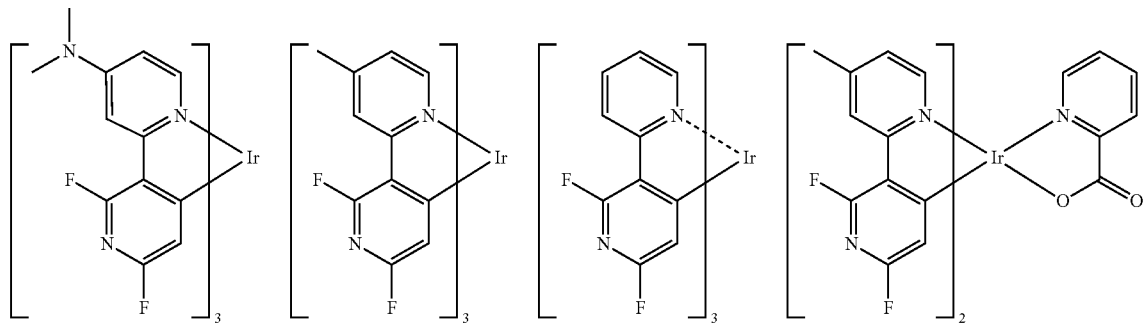

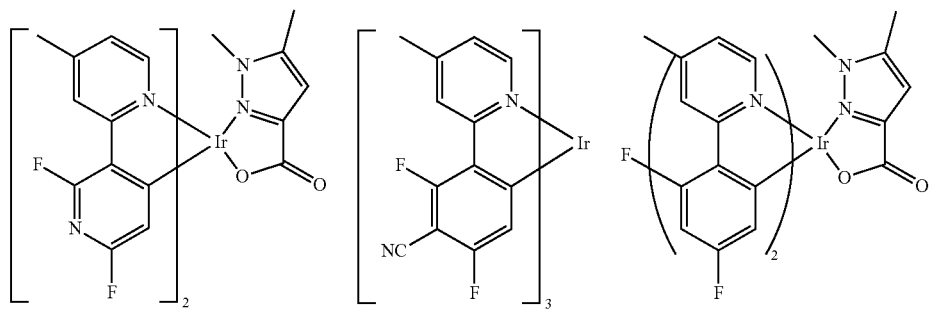

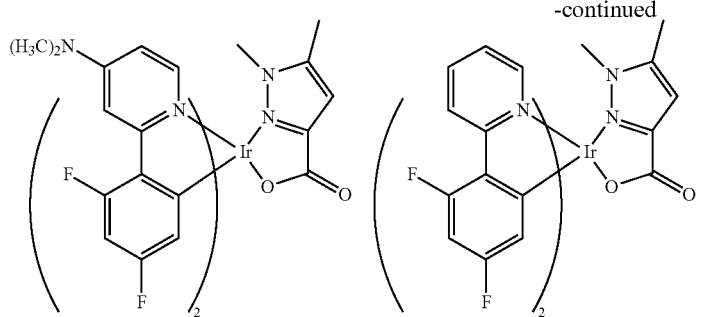
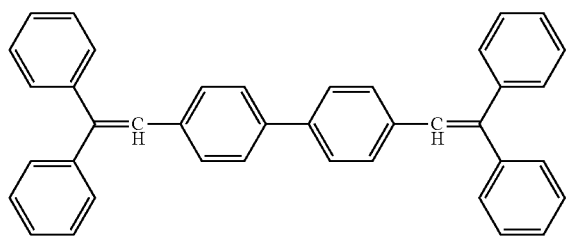
DPVBi
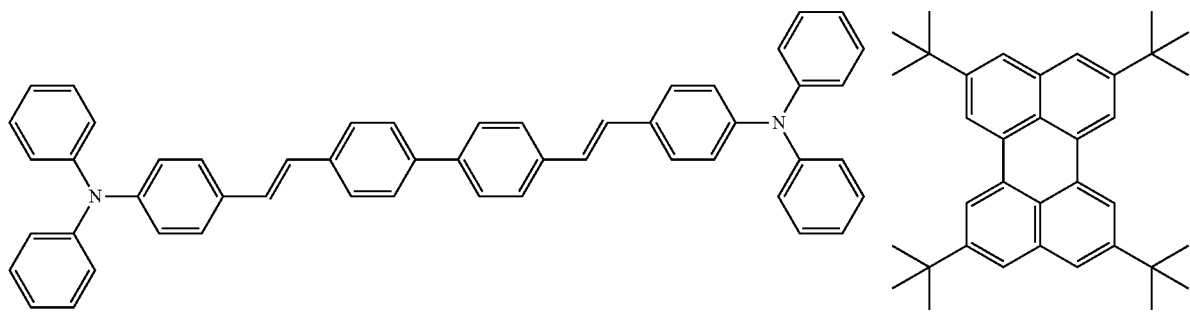
DPAVBi
TBPe
For example, the red EML of the red subpixels may include one or more of the compounds below as a red dopant, but the present disclosure is not limited thereto. Alternatively, the red dopant may include DCM or DCJTB as depicted below.
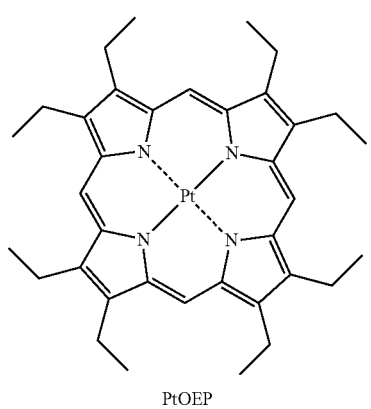
PtOEP
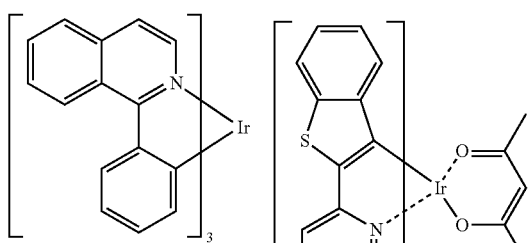
Ir(piq)$_3$
Btp$_2$Ir(acac)
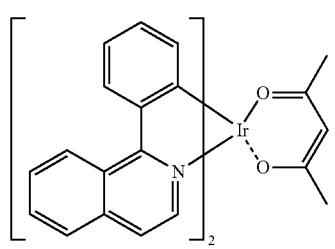

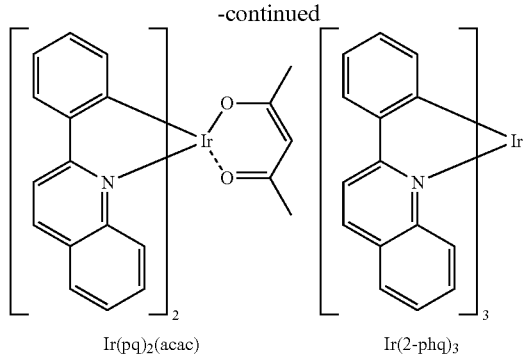
Ir(pq)₂(acac)  Ir(2-phq)₃
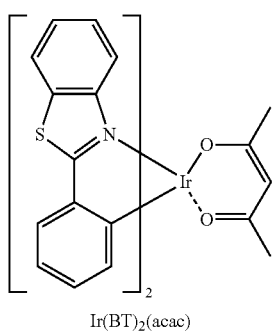
Ir(BT)₂(acac)
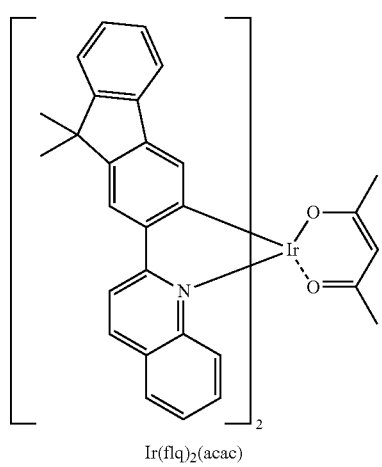
Ir(flq)₂(acac)
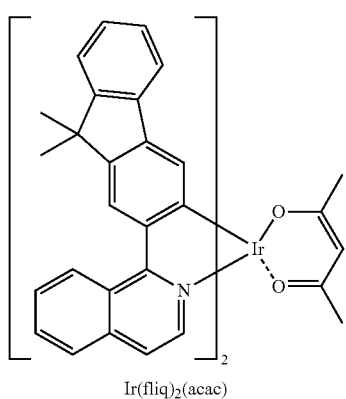
Ir(fliq)₂(acac)
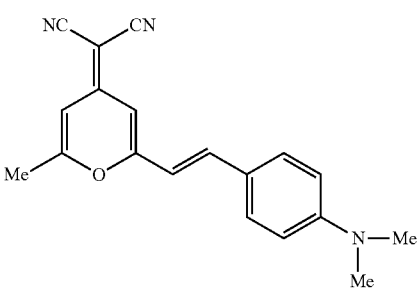
DCM
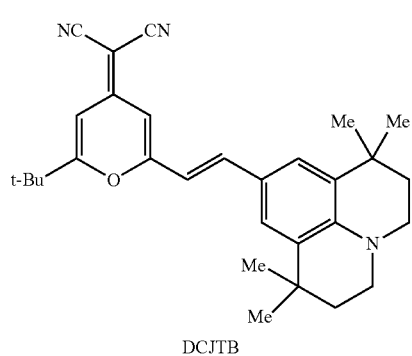
DCJTB
Also, a green EML of the green subpixels may include one or more of the compounds below as a green dopant, but the present disclosure is not limited thereto. Alternatively, the green dopant may include C545T as depicted below.
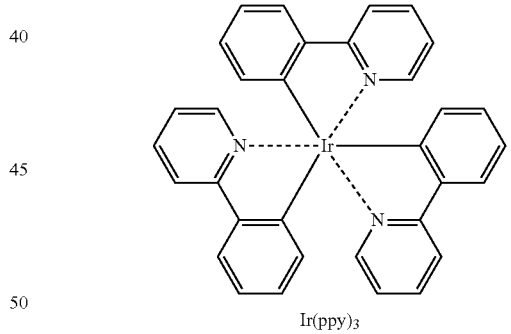
Ir(ppy)₃
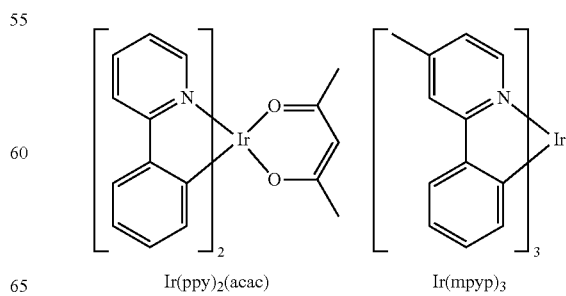
Ir(ppy)₂(acac)  Ir(mpyp)₃

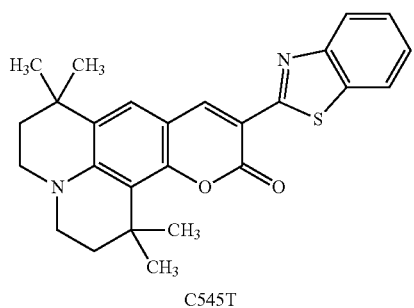
C545T
Meanwhile, additional examples of the dopant included in the EML include, but are not limited to, the Pt-complexes depicted below.
D1
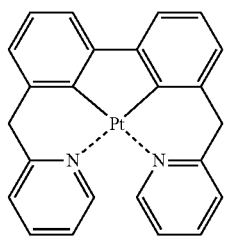
D2
D3
D4
D5
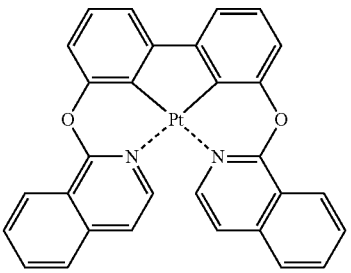
D6
D7
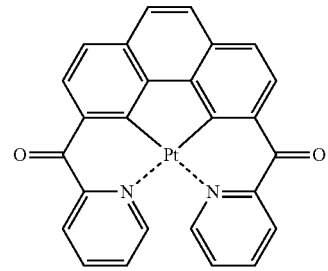
D8
D9
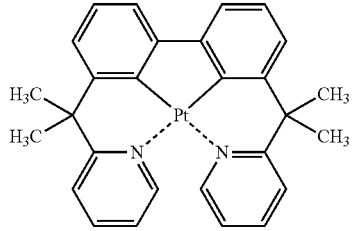
D10
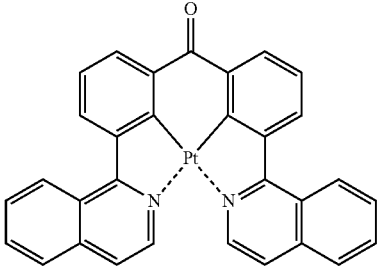

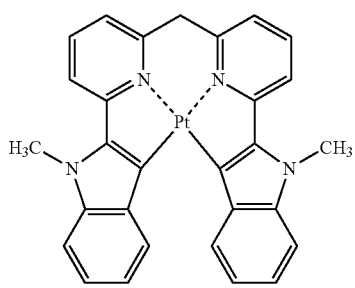
D11
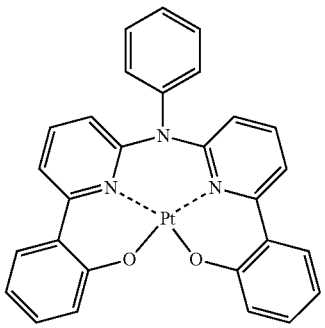
D16
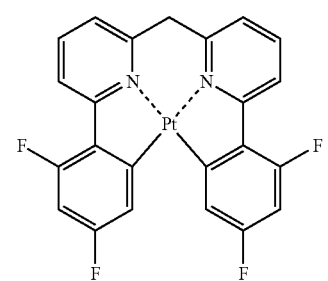
D12
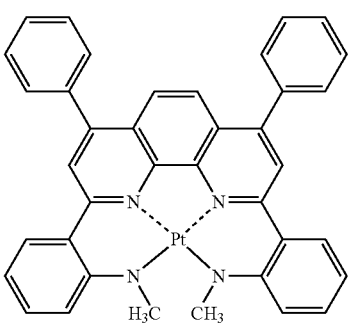
D17
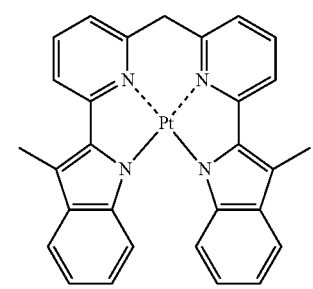
D13
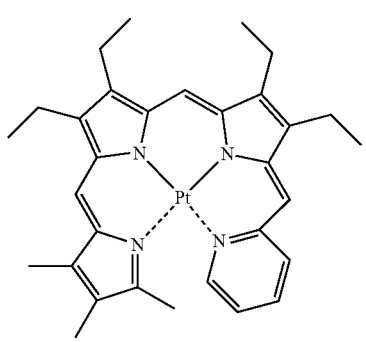
D14
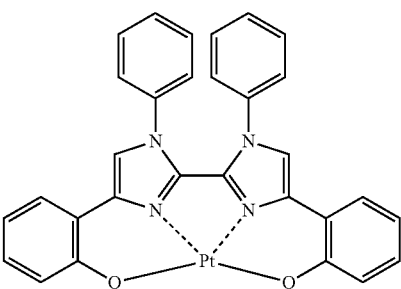
D18
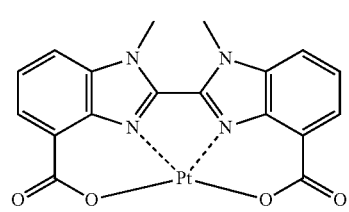
D19
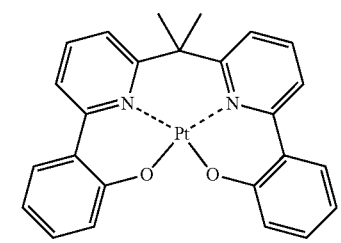
D15
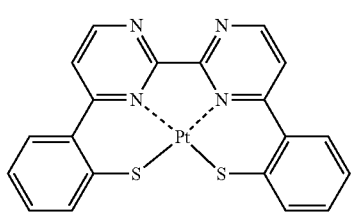
D20

-continued
D21 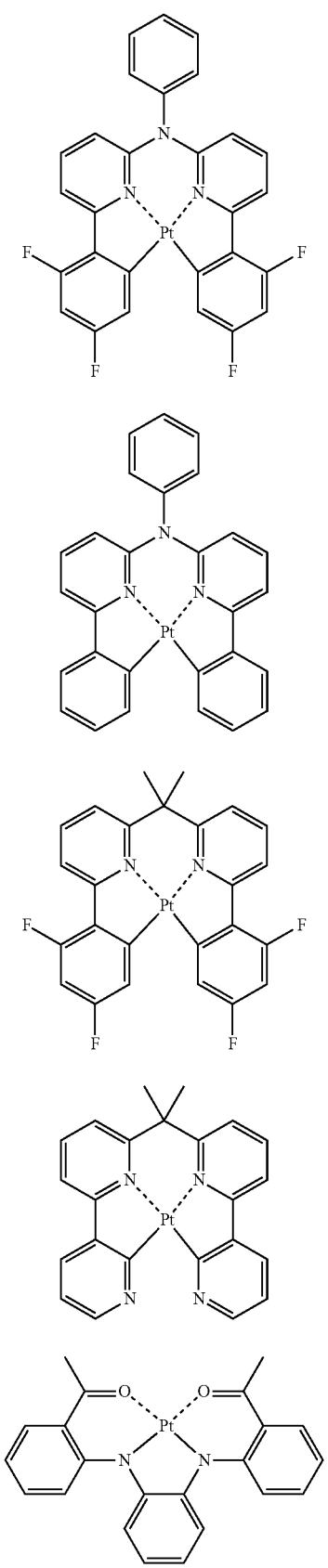
D22
D23
D24
D25
-continued
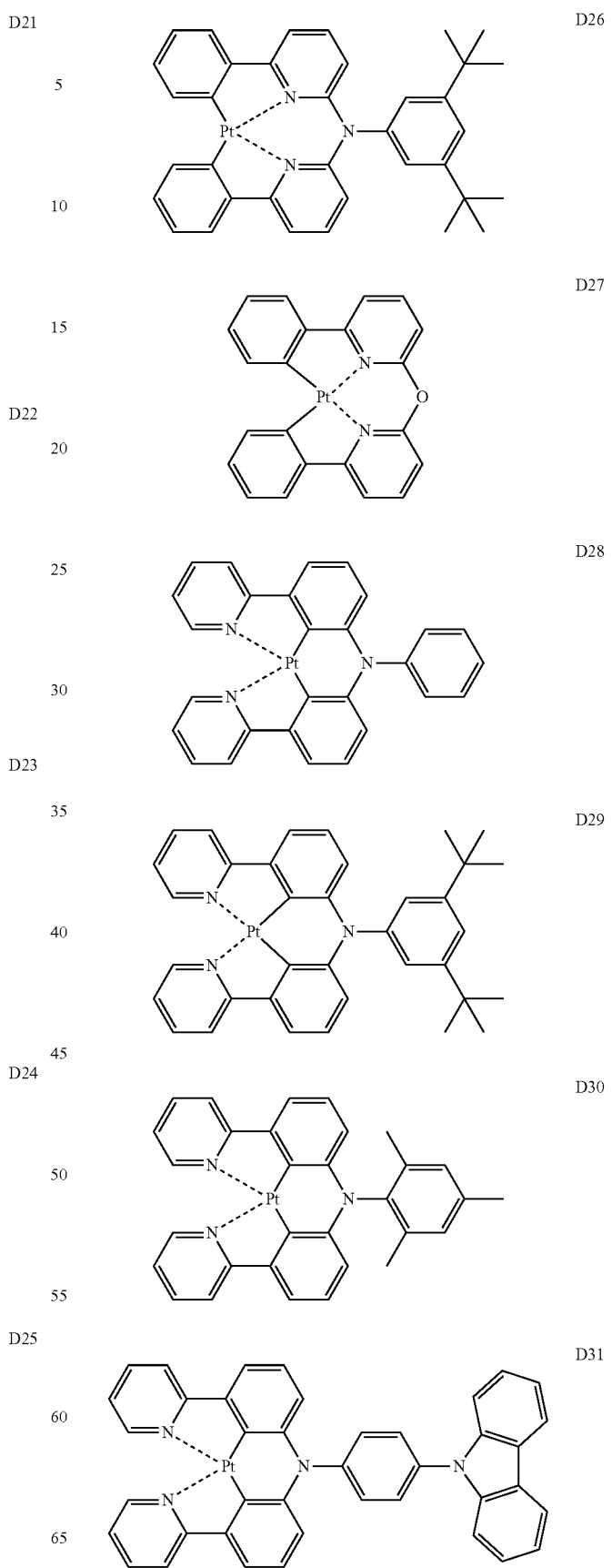
D26
D27
D28
D29
D30
D31

-continued
D32
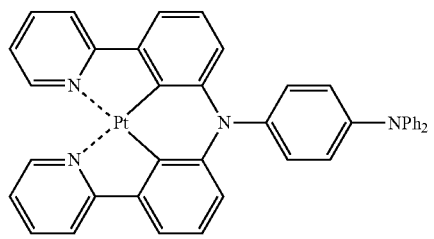
D33
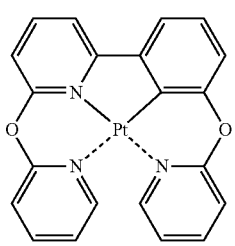
D34
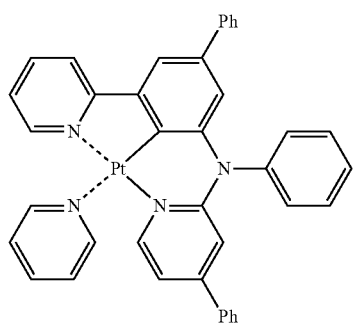
D35
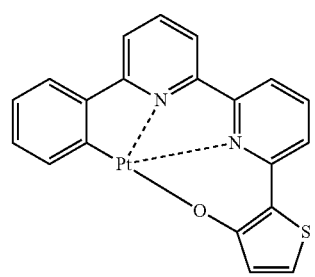
D36
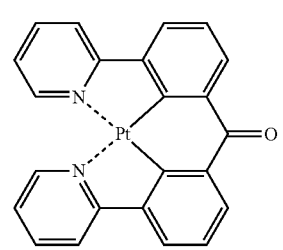
-continued
D37
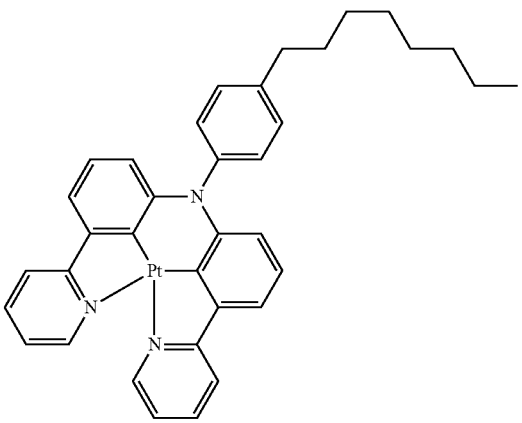
D38
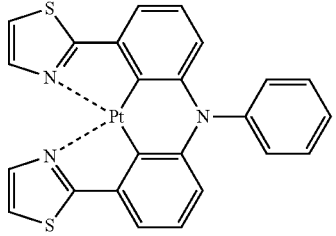
D39
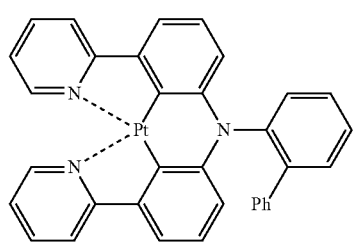
B40
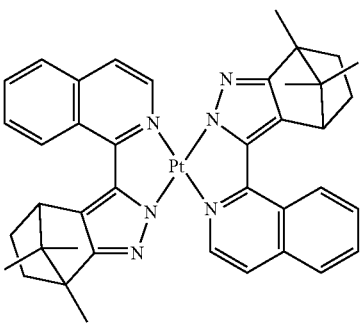
B41
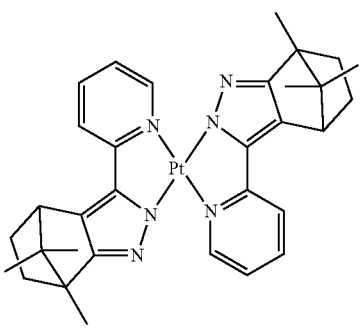

B42 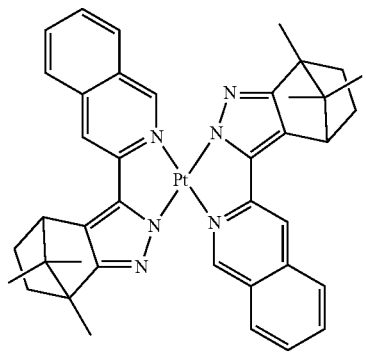
B43 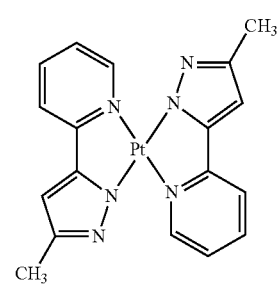
B44 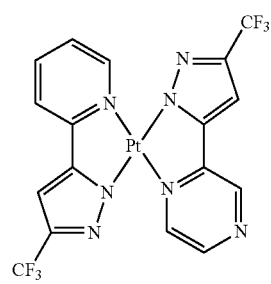
D45 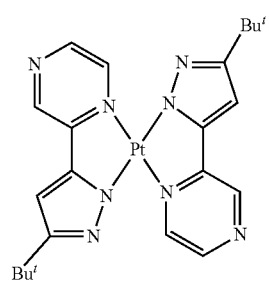
D46 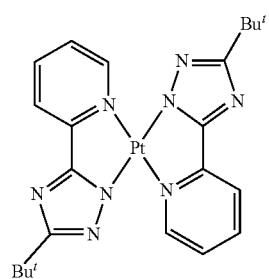
D47 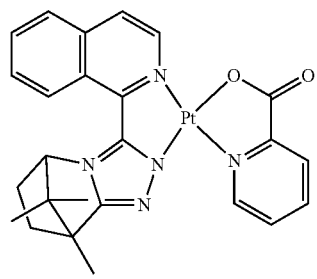
D48 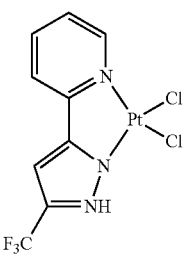
D49 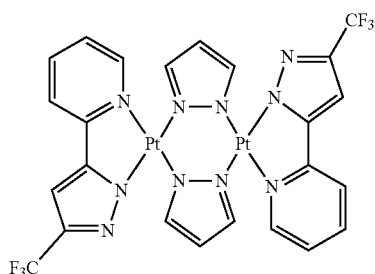
D50 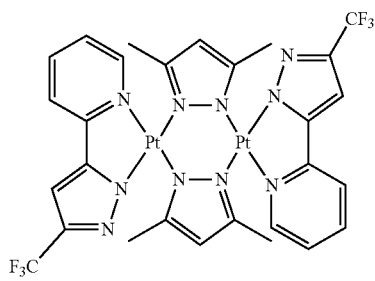
Moreover, additional examples of the dopant included in the EML include, but are not limited to, the Os-complexes depicted below.
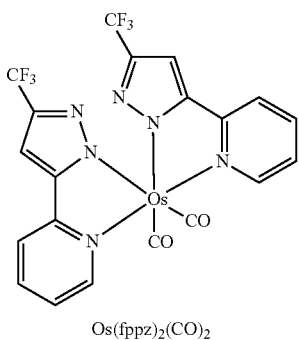
Os(fppz)$_2$(CO)$_2$

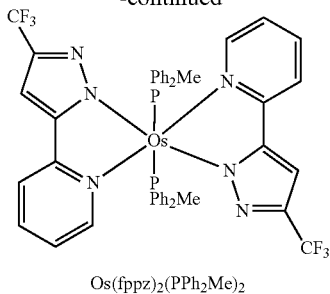

Os(fppz)₂(PPh₂Me)₂

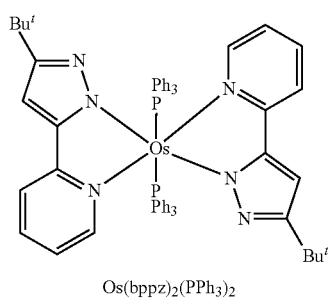

Os(bppz)₂(PPh₃)₂

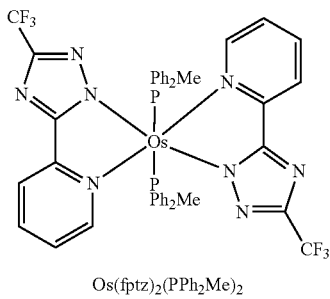

Os(fptz)₂(PPh₂Me)₂

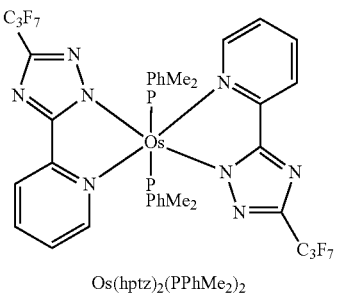

Os(hptz)₂(PPhMe₂)₂

When the EML includes a host and a dopant, the amount of the dopant in the EML may generally be in the range of about 0.01 to about 15 parts by weight based on 100 parts by weight of the host, but the present disclosure is not limited thereto.

The thickness of the EML may be in a range of about 100 Å to about 1,000 Å, for example, in a range of about 100 Å to about 600 Å. When the thickness of the EML is within these ranges, good luminescent properties may be obtained without a substantial increase in driving voltage.

Next, the ETL is formed on the EML using various methods, such as vacuum deposition, spin coating, or casting. When the ETL is formed by vacuum deposition or spin coating, the deposition or coating conditions may vary according to the compound used. However, in general, the conditions may be similar to the conditions described above with respect to formation of the HIL.

Any material for forming the ETL may be used so long as it stably transports electrons injected from the cathode, and the material may be any known electron transporting material. Examples of the electron transporting material may include, but are not limited to, quinoline derivatives such as tris(8-quinolinolate)aluminum (Alq₃), TAZ, Balq, beryllium bis(benzoquinolin-10-olate) (Bebq₂), AND, Compound 201 below, and Compound 202 below.

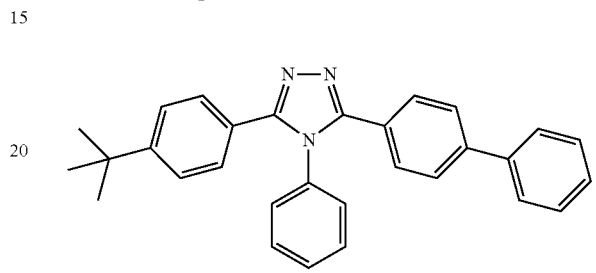

TAZ

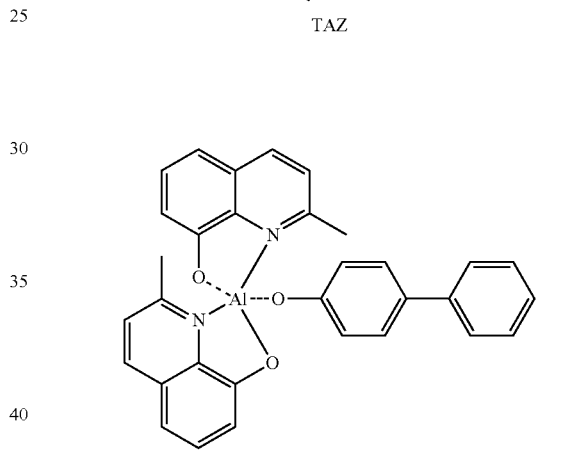

BAlq

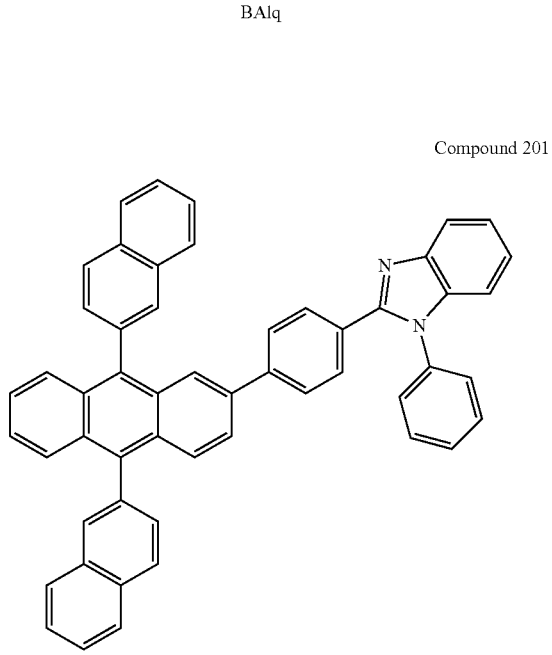

Compound 201

Compound 202

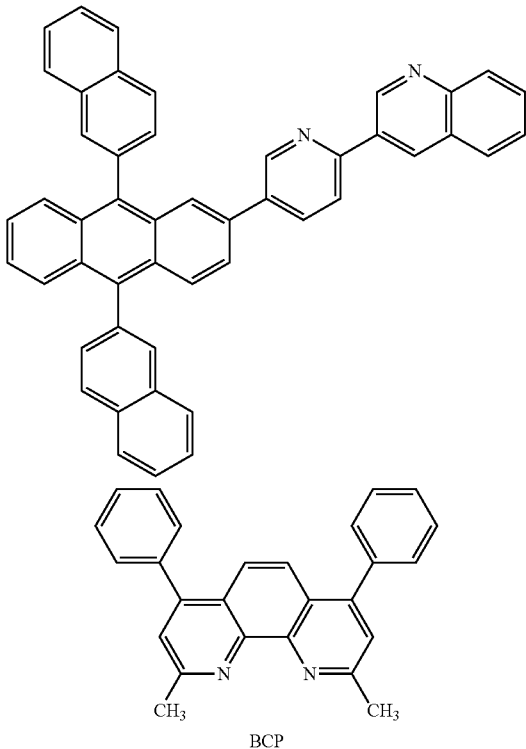

BCP

The thickness of the ETL may be in a range of about 100 Å to about 1,000 Å, for example, in a range of about 150 Å to about 500 Å. When the thickness of the ETL is within this range, satisfactory electron transport properties may be obtained without a substantial increase in driving voltage.

In addition, the ETL may further include a known electron transporting organic compound and a metal-containing material.

The metal-containing material may include a Li-complex. Examples of the Li-complex may include lithium quinolate (Liq) and Compound 203 below:

Compound 203

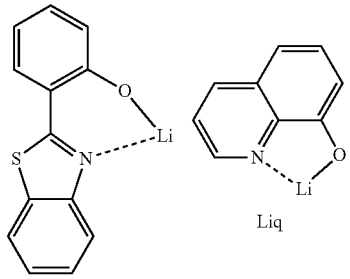

Liq

Also, the EIL, which facilitates electron injection from the cathode, may be deposited on the ETL, and a material for forming the EIL is not particularly limited.

The material for forming the EIL may include any known material for forming an EIL, such as LiF, NaCl, CsF, $Li_2O$, or BaO. The deposition conditions of the EIL may vary according the compound used. However, in general, the conditions may be similar to the conditions described above with respect to formation of the HIL.

The thickness of the EIL may be in a range of about 1 Å to about 100 Å, for example, in a range of about 3 Å to about 90 Å. When the thickness of the EIL is within these ranges, satisfactory electron injection properties may be obtained without a substantial increase in driving voltage.

The second electrode 17 is formed on the organic layer 15. The second electrode 17 may be a cathode, which is an electron injection electrode. Here, the material for forming the second electrode 17 may include a material having a low work function, such as metals, alloys, electric conducting compounds, and mixtures thereof.

In particular, the second electrode 17 may be formed as a thin film of lithium (Li), magnesium (Mg), aluminum (Al), aluminum-lithium (Al—Li), calcium (Ca), magnesium-indium (Mg—In), or magnesium-silver (Mg—Ag), thus being reflective, semitransparent, or transparent. In order to obtain a top-emission type OLED, the second electrode 17 may be formed as a transparent electrode by using ITO or IZO. When the OLED 10 is used in a large-scale full color display, the second electrode (cathode) 17 may be a reflective electrode, but the present disclosure is not limited thereto.

As described above, the OLED 10 is described with reference to FIG. 1, but the present disclosure is not limited thereto.

When a phosphorescent dopant is used to form the EML, a HBL may be formed between the HTL and the EML or the H-functional layer and the EML in order to prevent diffusion of triplet excitons or holes into an ETL. The HBL may be formed using various methods, such as vacuum deposition, spin coating, casting, LB deposition or the like. When the HBL is formed using vacuum deposition or spin coating, the deposition or coating conditions may vary according to the compound used. However, in general, the conditions may be similar to the conditions described above with respect to formation of the HIL.

Any material that is commonly used to form a HBL may be used. Examples of the material for forming the HBL include, but are not limited to, oxadiazole derivatives, triazole derivatives, and phenanthroline derivatives. For example, BCP (depicted below) may be used as the HBL material.

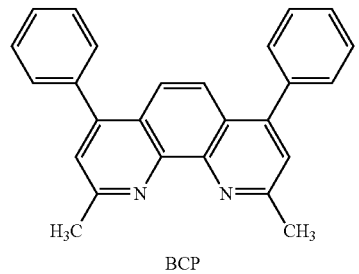

BCP

The thickness of the HBL may be in a range of about 20 Å to about 1,000 Å, for example, about 30 Å to about 300 Å. When the thickness of the HBL is within these ranges, the HBL may have good hole blocking ability without a substantial increase in driving voltage.

The OLED may be used in a full color display apparatus, lamp, or the like. For example, the OLED may be a full color display apparatus.

Thus, according to another embodiment of the present invention, an organic light-emitting apparatus may include a substrate including first subpixels, second subpixels, and third subpixels; a plurality of first electrodes, each separately formed for the first subpixels, the second subpixels, and the third subpixels of the substrate; a second electrode (opposite the first electrode) as a common electrode formed commonly on the first, second, and third subpixels; a first EML between the second electrode and the first electrode of the first subpixels, where the first EML emits light of a first color; a second EML between the second electrode and the first electrode of the second subpixels, where the second EML emits light of a second color; and a third EML between the second electrode and the first electrode of the third subpixels, where the third EML emits light of a third color. The first EML includes at least one pyrene-based compound represented by Formula I. Here, the first electrodes may be transparent electrodes or semitransparent electrodes, and the second electrode may be a reflective electrode. Alternatively, the first electrodes may be reflective electrodes, and the second electrode may be a transparent electrode or a semitransparent electrode.

In the organic light-emitting apparatus, the light resulting from the mixture of the light of the first color, the light of the second color and the light of the third color may be white light. Thus, the organic light-emitting apparatus may be a full color display apparatus. The light of the first color may be blue light. Also, the light of the second color may be green light, and the light of the third color may be red light.

The first EML of the organic light-emitting apparatus includes the pyrene-based compound represented by Formula 1 above, and thus may emit light of the first color (blue light) having good color purity (e.g., a y-coordinate of 0.1 or less) that is close to the NTSC or sRGB standards. Therefore, the organic light-emitting apparatus may be used in a high-quality large-scale TV.

The organic light-emitting apparatus may be a bottom-emission type organic light-emitting apparatus, in which the first electrodes may be transparent electrodes or semitransparent electrodes, and the second electrode may be a reflective electrode.

Alternatively, the organic light-emitting apparatus may be a top-emission type organic light-emitting apparatus, in which the first electrodes may be reflective electrodes, and the second electrode may be a transparent electrode or a semitransparent electrode.

Since the organic light-emitting apparatus may emit blue light having good color purity (e.g., a y-coordinate of 0.1 or less) that is close to the sRGB standard by using the pyrene-based compound represented by Formula 1 above, a complex resonant structure or the like for supplementing the color purity of the blue light may not be necessary, thus reducing manufacturing cost and the like.

The full color display may be used in a TV, a personal computer monitor, a mobile device, a MP3 player, a car navigator, or the like.

As used herein, examples of an unsubstituted $C_1$-$C_{60}$ alkyl group (or a $C_1$-$C_{60}$ alkyl group) may be linear or branched $C_1$-$C_{60}$ alkyl groups such as a methyl group, an ethyl group, a propyl group, an isobutyl group, a sec-butyl group, a pentyl group, an iso-amyl group, or a hexyl group. A substituted $C_1$-$C_{60}$ alkyl group may be the unsubstituted $C_1$-$C_{60}$ alkyl group in which at least one of the hydrogen atoms is substituted with deuterium, —F; —Cl; —Br; —CN; a hydroxyl group; —NO$_2$; an amino group; an amidino group; hydrazine; hydrazone; a carboxyl group or a salt thereof; a sulfonic acid group or a salt thereof; a phosphoric acid or a salt thereof; a tri($C_6$-$C_{60}$ aryl)silyl group; a $C_1$-$C_{60}$ alkyl group, a $C_1$-$C_{60}$ alkoxy group, a $C_2$-$C_{60}$ alkenyl group, or a $C_2$-$C_{60}$ alkynyl group; a $C_1$-$C_{60}$ alkyl group, a $C_1$-$C_{60}$ alkoxy group, a $C_2$-$C_{60}$ alkenyl group, or a $C_2$-$C_{60}$ alkynyl group substituted with at least one of deuterium, —F, —Cl, —Br, —CN, a hydroxyl group, —NO$_2$, an amino group, an amidino group, hydrazine, hydrazone, a carboxyl group or a salt thereof, a sulfonic acid group or a salt thereof, or a phosphoric acid group or a salt thereof; a $C_3$-$C_{60}$ cycloalkyl group, a $C_3$-$C_{60}$ cycloalkenyl group, a $C_6$-$C_{60}$ aryl group, a $C_2$-$C_{60}$ heteroaryl group, a $C_6$-$C_{60}$ aralkyl group, a $C_6$-$C_{60}$ aryloxy group, or a $C_6$-$C_{60}$ arylthio group; or a $C_3$-$C_{60}$ cycloalkyl group, a $C_3$-$C_{60}$ cycloalkenyl group, a $C_6$-$C_{60}$ aryl group, a $C_2$-$C_{60}$ heteroaryl group, a $C_6$-$C_{60}$ aralkyl group, a $C_6$-$C_{60}$ aryloxy group, or a $C_6$-$C_{60}$ arylthio group substituted with at least one of deuterium, —F, —Cl, —Br, —I, —CN, a hydroxyl group, —NO$_2$, an amino group, an amidino group, hydrazine, hydrazone, a carboxyl group or a salt thereof, a sulfonic acid group or a salt thereof, a phosphoric acid group or a salt thereof, a $C_1$-$C_{60}$ alkyl group, a $C_1$-$C_{60}$ alkyl group substituted with at least one —F, $C_1$-$C_{60}$ alkoxy group, a $C_2$-$C_{60}$ alkenyl group, a $C_2$-$C_{60}$ alkynyl group, a $C_6$-$C_{60}$ aryl group, or a $C_2$-$C_{60}$ heteroaryl group.

As used herein, the unsubstituted $C_1$-$C_{60}$ alkoxy group (or $C_1$-$C_{60}$ alkoxy group) has the formula —OA in which A is an unsubstituted $C_1$-$C_{60}$ alkyl group as described above. Examples of the alkoxy group include methoxy, ethoxy, isopropyloxy, and the like. One or more hydrogen atoms of the unsubstituted $C_1$-$C_{60}$ alkoxy group may be substituted with the substituents described above with reference to the $C_1$-$C_{60}$ alkyl group.

As used herein, the unsubstituted $C_2$-$C_{60}$ alkenyl group is understood to contain one or more carbon-carbon double bonds in the center or at a terminal end of an unsubstituted $C_2$-$C_{60}$ alkyl group. Examples of the unsubstituted $C_2$-$C_{60}$ alkenyl group include ethenyl, propenyl, butenyl, and the like. One or more hydrogen atoms of the unsubstituted $C_2$-$C_{60}$ alkenyl group may be substituted with the substituents described above with reference to the $C_1$-$C_{60}$ alkyl group.

As used herein, the unsubstituted $C_2$-$C_{60}$ alkynyl group is understood to contain one or more carbon-carbon triple bonds in the center or at a terminal end of an unsubstituted $C_2$-$C_{60}$ alkyl group defined above. Examples of the unsubstituted $C_2$-$C_{60}$ alkynyl group include ethynyl, propynyl, and the like. One or more hydrogen atoms of the unsubstituted $C_2$-$C_{60}$ alkynyl group may be substituted with the substituents described above with reference to the $C_1$-$C_{60}$ alkyl group.

As used herein, the unsubstituted $C_3$-$C_{60}$ cycloalkyl group is understood as a monovalent cyclic-type saturated hydrocarbon group having 3 to 60 carbon atoms. Examples of the cycloalkyl group include a cyclopropyl, a cyclobutyl, a cylcopentyl, a cyclohexyl, a cyclooctyl, or the like. One or more hydrogen atoms of the cycloalkyl group may be substituted with the substituents described above with reference to the $C_1$-$C_{60}$ alkyl group.

As used herein, the unsubstituted $C_3$-$C_{60}$ cycloalkenyl group is understood to contain one or more carbon-carbon double bonds and a non-aromatic ring-type unsaturated hydrocarbon group. Examples of the cycloalkenyl group include a cyclopropenyl, a cyclobutenyl, a cylcopentenyl, a cyclohexenyl, a cycloheptenyl, a 1,3-cyclohexadienyl group, a 1,4-cyclohexadienyl group, a 2,4-cycloheptadienyl group, a 1,5-cyclooctadineyl group, or the like. One or more hydrogen atoms of the cycloalkenyl group may be substituted with the substituents described above with reference to the $C_1$-$C_{60}$ alkyl group.

As used herein, the unsubstituted $C_6$-$C_{60}$ aryl group may indicate a monovalent group having an aromatic carbocyclic system that has 6 to 60 carbon atoms and one or more aromatic rings. The unsubstituted $C_6$-$C_{60}$ arylene group may indicate a divalent group having an aromatic carbocyclic system that has 6 to 60 carbon atoms and one or more aromatic rings. If each of the unsubstituted $C_5$-$C_{60}$ aryl group and the unsubstituted $C_5$-$C_{60}$ arylene group includes two or more rings, the rings may be fused with each other. One or more hydrogen atoms of each of the unsubstituted $C_5$-$C_{60}$ aryl group and the unsubstituted $C_5$-$C_{60}$ arylene group may be substituted with the substituents described above with reference to the $C_1$-$C_{60}$ alkyl group.

Examples of the substituted or unsubstituted $C_6$-$C_{60}$ aryl group include a phenyl group, a $C_1$-$C_{10}$ alkylphenyl group (e.g., an ethylphenyl group), a $C_1$-$C_{10}$ alkylbiphenyl group (e.g., an ethylbiphenyl group), a halophenyl group (e.g., o-, m-, or p-fluorophenyl group, dichlorophenyl group), a dicyanophenyl group, a trifluoromethoxyphenyl group, o-, m-, or p-tolyl group, o-, m-, or p-cumenyl, a mesityl group, a phenoxyphenyl group, a (α,α-dimethylbenzene)phenyl group, a (N,N'-dimethyl)aminophenyl group, a (N,N'-diphenyl)aminophenyl group, a pentalenyl group, an indenyl group, a naphthyl group, a halonaphthyl group (e.g., a fluoronaphthyl group), a $C_1$-$C_{10}$ alkylnaphthyl group (e.g., a methylnaphthyl group), a $C_1$-$C_{10}$ alkoxynaphthyl group (e.g., a methoxynaphthyl group), a anthracenyl group, an azulenyl group, a heptalenyl group, an acenaphthylenyl group, a phenalenyl group, a fluorenyl group, an anthraquinolyl group, a methylanthryl group, a phenanthryl group, a triphenylenyl group, a pyrenyl group, a chrysenyl group, an ethyl-chrysenyl group, a picenyl group, a perylenyl group, a chloroperylenyl group, a pentaphenyl group, a pentacenyl group, a tetraphenylenyl group, a hexaphenyl group, a hexacenyl group, a rubicenyl group, a coronenyl group, a trinaphthylenyl group, a heptaphenyl group, a heptacenyl group, a pyranthrenyl group, or an ovalenyl group. Examples of the substituted $C_6$-$C_{60}$ aryl group may be easily understood with reference to the examples of the unsubstituted $C_6$-$C_{60}$ aryl group described above, and the substituents of the substituted $C_1$-$C_{60}$ alkyl group. Examples of the substituted or unsubstituted $C_6$-$C_{60}$ arylene group may be easily understood with reference to the substituted or unsubstituted $C_6$-$C_{60}$ aryl group described above.

As used herein, the unsubstituted $C_2$-$C_{60}$ heteroaryl group indicates a monovalent group having at least one aromatic ring system including carbon atoms and one or more hetero atoms selected from N, O, P, and S as the ring-forming atoms. The unsubstituted $C_2$-$C_{60}$ heteroarylene group indicates a divalent group having at least one aromatic ring system including carbon atoms and one or more hetero atoms selected from N, O, P, and S. In this regard, if the $C_2$-$C_{60}$ heteroaryl group or the $C_2$-$C_{60}$ heteroarylene group have two or more aromatic rings, the rings may be fused with each other. One or more hydrogen atoms of each of the unsubstituted $C_2$-$C_{60}$ heteroaryl group and the unsubstituted $C_2$-$C_{60}$ heteroarylene group may be substituted with the substituents described above with reference to the $C_1$-$C_{60}$ alkyl group.

Examples of the unsubstituted $C_2$-$C_{60}$ heteroaryl group include a pyrazolyl group, an imidazolyl group, an oxazolyl group, a thiazolyl group, a triazolyl group, a tetrazolyl group, an oxadiazolyl group, a pyridinyl group, a pyridazinyl group, a pyrimidinyl group, a triazinyl group, a carbazolyl group, an indolyl group, a quinolinyl group, an isoquinolinyl group, a benzoimidazolyl group, an imidazopyridinyl group, or an imidazopyrimidinyl group. Examples of the unsubstituted $C_2$-$C_{60}$ heteroarylene group may be easily understood with reference to the examples of the unsubstituted $C_2$-$C_{60}$ heteroarylene group.

The substituted or unsubstituted $C_6$-$C_{60}$ aryloxy group has the formula —$OA_2$ where $A_2$ is a substituted or unsubstituted $C_6$-$C_{60}$ aryl group as described above. The substituted or unsubstituted $C_6$-$C_{60}$ arylthio group has the formula —$SA_3$ where $A_3$ is a substituted or unsubstituted $C_6$-$C_{60}$ aryl group as described above.

Hereinafter, an OLED according to an embodiment of the present invention will be described with reference to the following examples. However, these examples are presented for illustrative purposes only and do not limit the scope of the invention.

EXAMPLES

Synthesis Example 1

Synthesis of Compound 1

Synthesis of Intermediate A-1

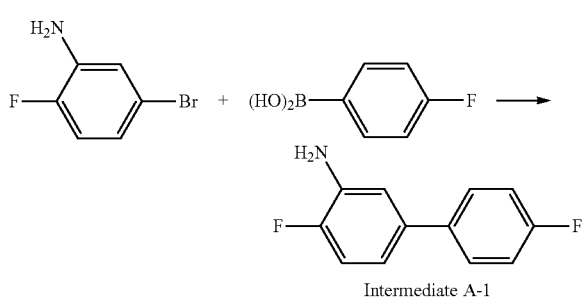

Intermediate A-1

5.7 g (30 mmol) of 5-bromo-2-fluoroaniline, 4.2 g (30 mmol) of (4-fluorophenyl)boronic acid, 520 mg (0.45 mmol) of tetrakistriphenylphosphinopalladium (Pd(PPh$_3$)$_4$), and 63 ml (126 mmol) of a 2M K$_2$CO$_3$ aqueous solution were dissolved in 200 ml of toluene and mixed. The mixture was refluxed for 24 hours. After the reaction was completed, the solvent was removed by evaporation, 500 ml of ethylacetate and 500 ml of water were added to wash the resultant, and an organic layer was collected and dried using magnesium sulfate anhydride. Then, the resultant was purified by silica gel chromatography, and 4.0 g of Intermediate A-1 was obtained (65% yield).

Synthesis of Intermediate A

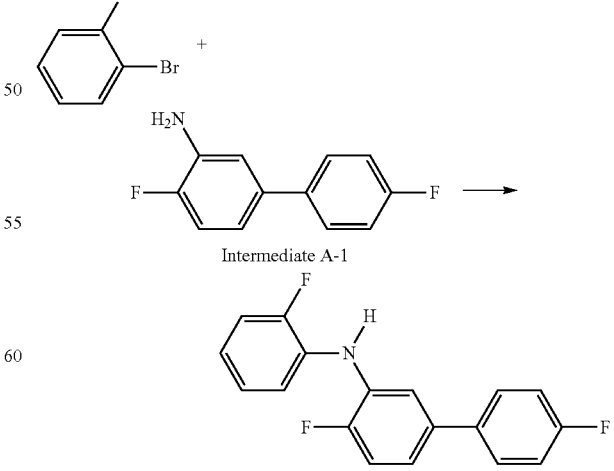

Intermediate A

In a nitrogen atmosphere, 1.3 g (7.2 mmol) of 1-bromo-2-fluorobenzene, 1.5 g (7.2 mmol) of Intermediate A-1, 80 mg (0.36 mmol) of palladium acetate (Pd(OAc)$_2$), 216 mg (1.08 mmol) of tri-tert-butyl phosphine (P(t-Bu)$_3$), and 2.0 g (22 mmol) of sodium t-butoxide were added to 200 ml of toluene and refluxed for 12 hours. After the reaction was completed, the solvent was removed by evaporation, 1,000 ml of methylene chloride and 1,000 ml of water were added to wash the resultant, and an organic layer was collected and dried using magnesium sulfate anhydride. Then, the resultant was purified by recrystallization and silica gel chromatography, and 0.7 g of Intermediate A was obtained (32% yield).

Synthesis of Intermediate B-1

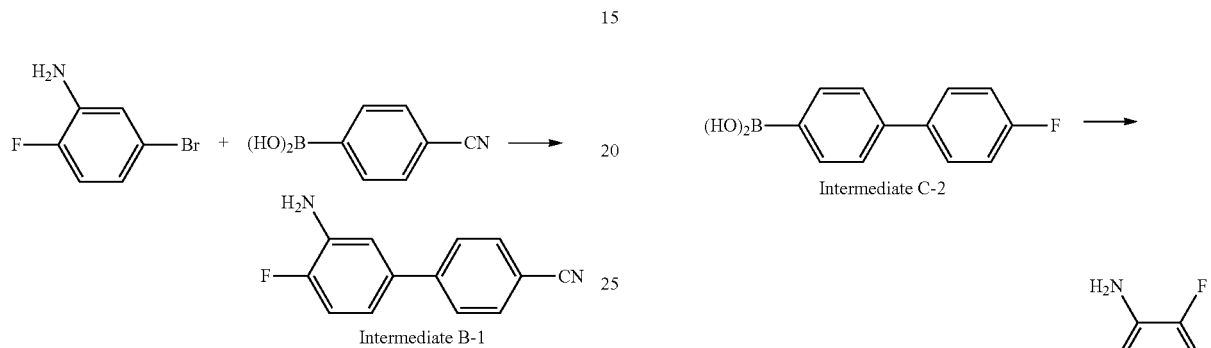

Intermediate B-1 was obtained as in the Synthesis of Intermediate A-1, except that (4-cyanophenyl)boronic acid was used instead of (4-fluorophenyl)boronic acid.

Synthesis of Intermediate B

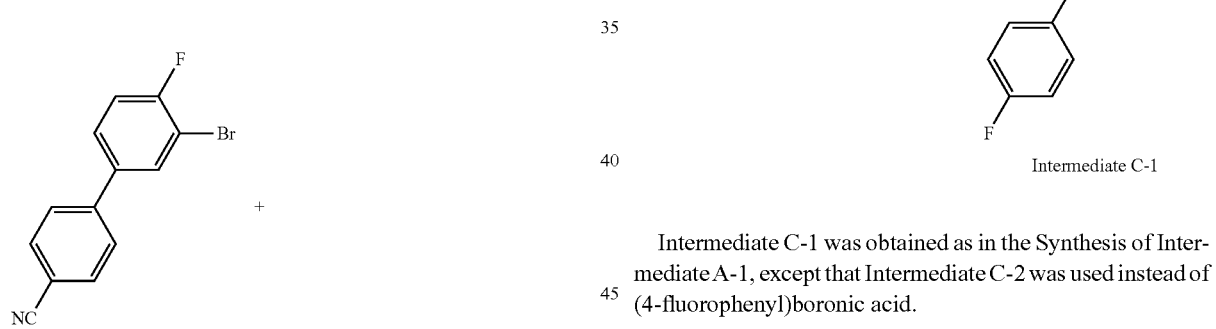

Intermediate B was obtained as in the Synthesis of Intermediate A, except that Intermediate B-2 was used instead of 1-bromo-2-fluorobenzene, and Intermediate B-1 was used instead of Intermediate A-1.

Synthesis of Intermediate C-1

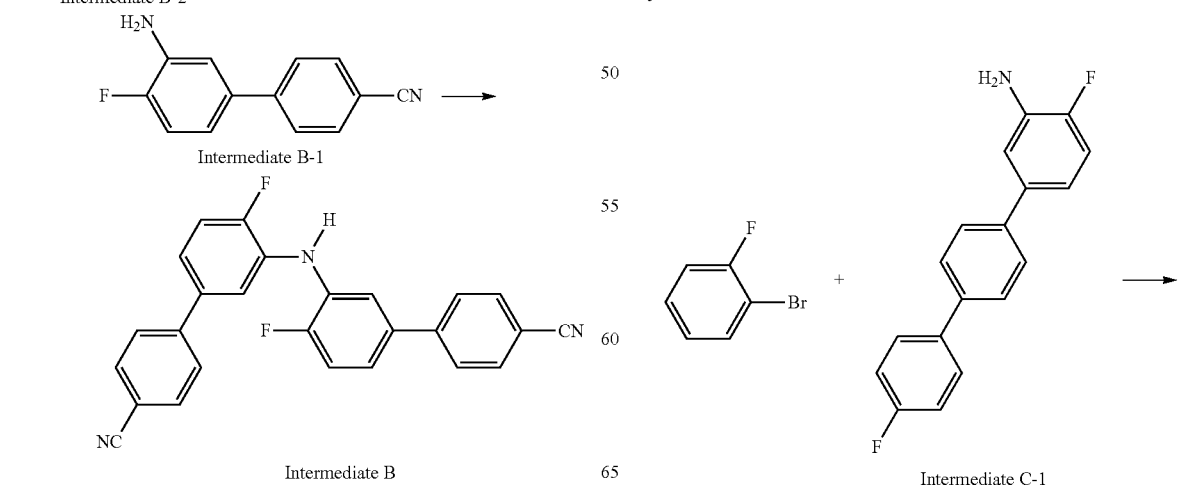

Intermediate C-1 was obtained as in the Synthesis of Intermediate A-1, except that Intermediate C-2 was used instead of (4-fluorophenyl)boronic acid.

Synthesis of Intermediate C

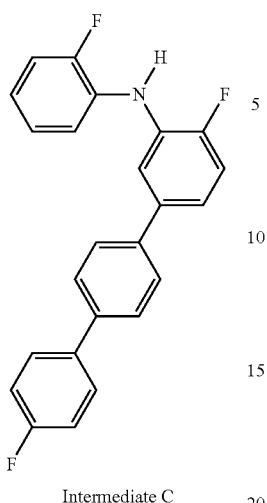

Intermediate C

Intermediate C was obtained as in the Synthesis of Intermediate A, except that Intermediate C-1 was used instead of Intermediate A-1.

Synthesis of Intermediate D-1

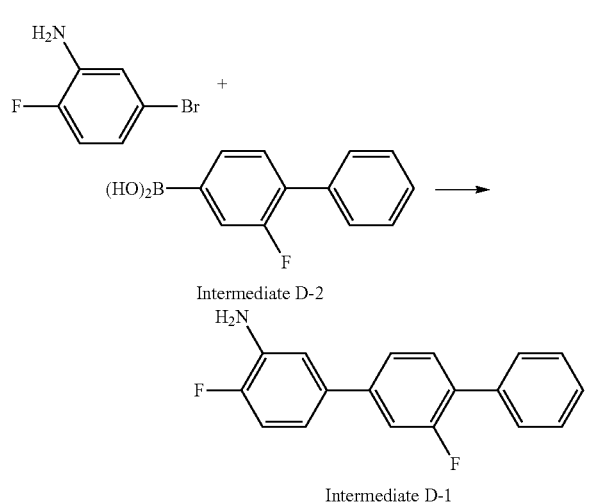

Intermediate D-1

Intermediate D-1 was obtained as in the Synthesis of Intermediate A-1, except that Intermediate D-2 was used instead of (4-fluorophenyl)boronic acid.

Synthesis of Intermediate D

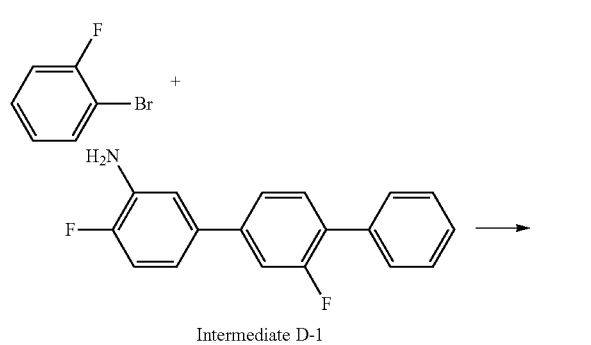

Intermediate D-1

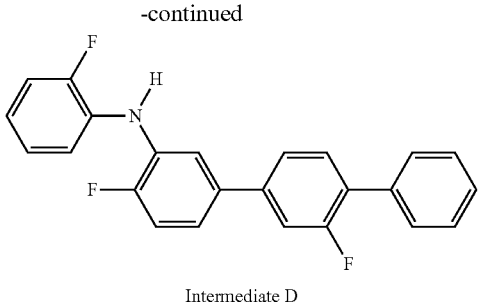

Intermediate D

Intermediate D was obtained as in the Synthesis of Intermediate A, except that Intermediate D-1 was used instead of Intermediate A-1.

Synthesis of Intermediate E-1

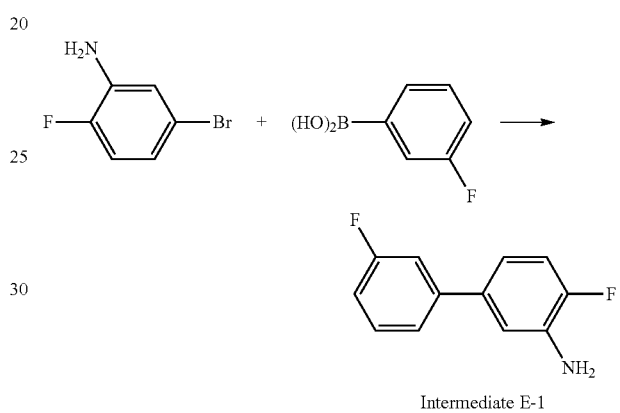

Intermediate E-1

Intermediate E-1 was obtained as in the Synthesis of Intermediate A-1, except that (3-fluorophenyl)boronic acid was used instead of (4-fluorophenyl)boronic acid.

Synthesis of Intermediate E

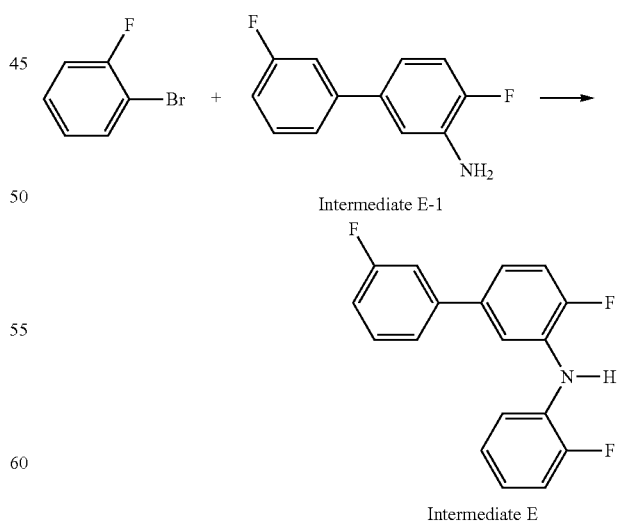

Intermediate E

Intermediate E was obtained as in Synthesis of Intermediate A, except that Intermediate E-1 was used instead of Intermediate A-1.

Synthesis of Compound 1

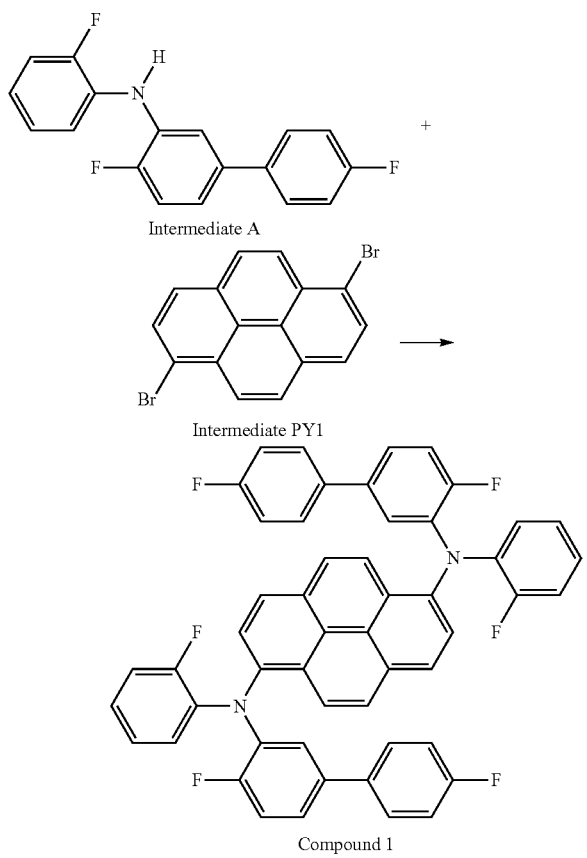

Compound 1

In a nitrogen atmosphere, 2.2 g (7.2 mmol) of Intermediate A, 1.3 g (3.6 mmol) of Intermediate PY1, 40 mg (0.18 mmol) of Pd(OAc)$_2$, 108 mg (0.54 mmol) of P(t-Bu)$_3$, and 1.0 g (10.9 mmol) of sodium t-butoxide were added to 100 ml of toluene and refluxed for 12 hours. After the reaction was completed, the solvent was removed by evaporation, 1,000 ml of methylene chloride and 1,000 ml of water were added to wash the resultant, and an organic layer was collected and dried using magnesium sulfate anhydride. Then, the resultant was purified by recrystallization and silica gel chromatography, and 1.2 g of Compound 1 was obtained (41% yield).

H-NMR (CDCl$_3$, 300 MHz, ppm): 7.7-7.3 (m, 14H), 7.1-6.9 (m, 8H), 6.8-6.6 (m, 8H).

MS (MALDI-TOF) m/z: 796 [M]+.

Synthesis of Compound 5

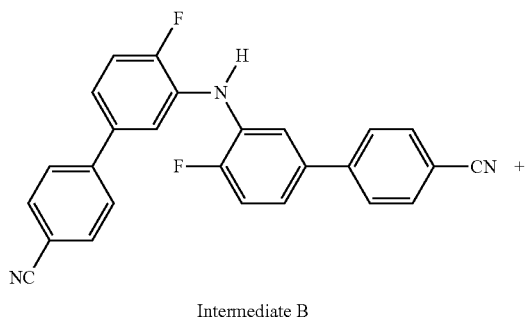

Intermediate B

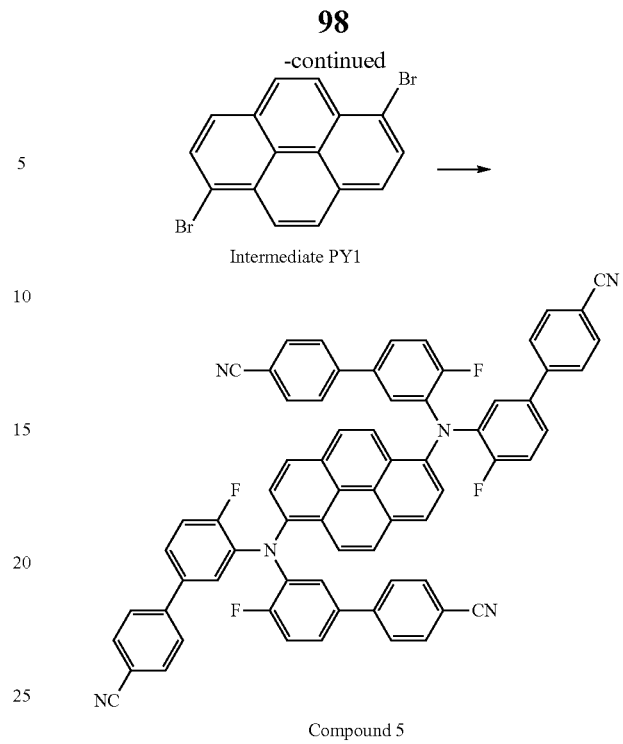

Compound 5

In a nitrogen atmosphere, 2.9 g (7.2 mmol) of Intermediate B, 1.3 g (3.6 mmol) of Intermediate PY1, 40 mg (0.18 mmol) of Pd(OAc)$_2$, 108 mg (0.54 mmol) of P(t-Bu)$_3$, and 1.0 g (10.9 mmol) of sodium t-butoxide were added to 100 ml of toluene and refluxed for 12 hours. After the reaction was completed, the solvent was removed by evaporation, 1,000 ml of methylene chloride and 1,000 ml of water were added to wash the resultant, and an organic layer was collected and dried using magnesium sulfate anhydride. Then, the resultant was purified by recrystallization and silica gel chromatography, and 1.4 g of Compound 5 was obtained (39% yield).

H-NMR (CDCl$_3$, 300 MHz, ppm): 7.8-7.4 (m, 22H), 7.1-7.0 (m, 8H), 6.8-6.6 (m, 8H).

MS (MALDI-TOF) m/z: 1012 [M]+.

Synthesis of Compound 9

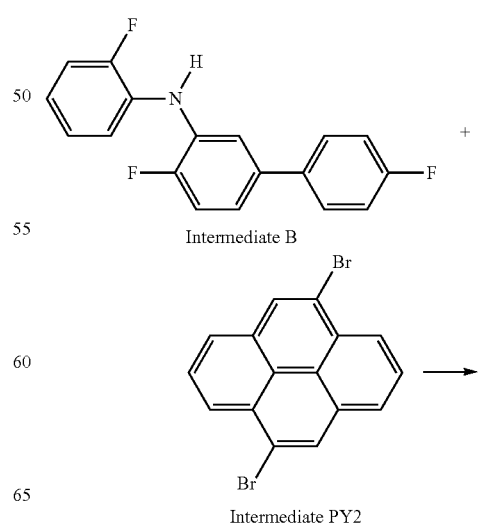

Intermediate PY2

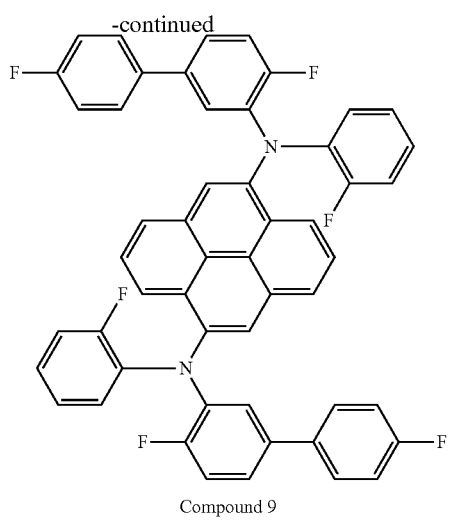

Compound 9

In a nitrogen atmosphere, 5.8 g (14.4 mmol) of Intermediate B, 2.6 g (7.2 mmol) of Intermediate PY2, 80 mg (0.36 mmol) of Pd(OAc)$_2$, 216 mg (1.08 mmol) of P(t-Bu)$_3$, and 2.0 g (21.8 mmol) of sodium t-butoxide were added to 200 ml of toluene and refluxed for 12 hours. After the reaction was completed, the solvent was removed by evaporation, 1,500 ml of methylene chloride and 1,500 ml of water were added to wash the resultant, and an organic layer was collected and dried using magnesium sulfate anhydride. Then, the resultant was purified by recrystallization and silica gel chromatography, and 3 g of Compound 9 was obtained (51% yield).

H-NMR (CDCl$_3$, 300 MHz, ppm): 8.0-7.3 (m, 10H), 7.1-6.9 (m, 10H), 6.8-6.6 (m, 10H).

MS (MALDI-TOF) m/z: 796 [M]+.

Synthesis of Compound 23

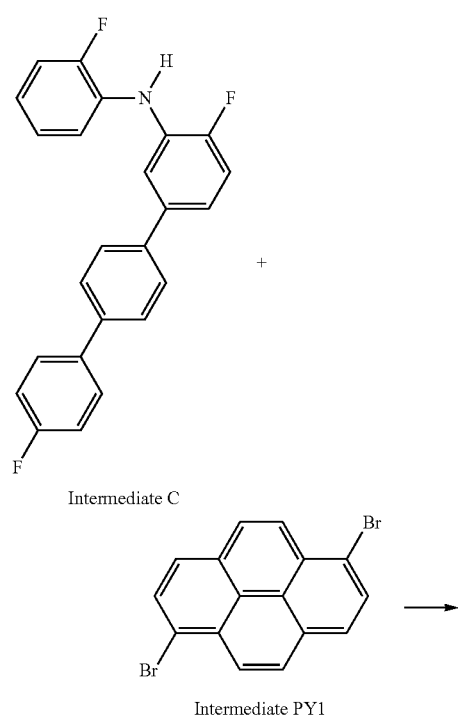

Intermediate C

Intermediate PY1

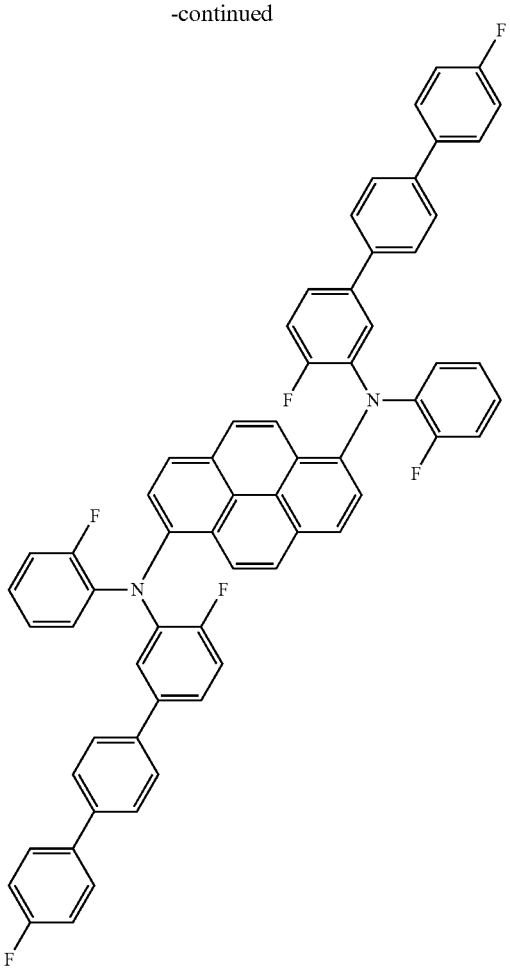

Compound 23

In a nitrogen atmosphere, 2.7 g (7.2 mmol) of Intermediate C, 1.3 g (3.6 mmol) of Intermediate PY1, 40 mg (0.18 mmol) of Pd(OAc)$_2$, 108 mg (0.54 mmol) of P(t-Bu)$_3$, and 1.0 g (10.9 mmol) of sodium t-butoxide were added to 100 ml of toluene and refluxed for 12 hours. After the reaction was completed, the solvent was removed by evaporation, 1,000 ml of methylene chloride and 1,000 ml of water were added to wash the resultant, and an organic layer was collected and dried using magnesium sulfate anhydride. Then, the resultant was purified by recrystallization and silica gel chromatography, and 1.5 g of Compound 23 was obtained (44% yield).

H-NMR (CDCl$_3$, 300 MHz, ppm): 7.8-7.6 (m, 6H), 7.4-7.3 (m, 16H), 7.1-6.9 (m, 10H), 6.8-6.6 (m, 6H).

MS (MALDI-TOF) m/z: 948 [M]+.

Synthesis of Compound 30

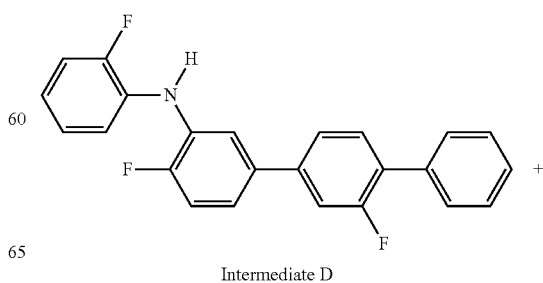

Intermediate D

-continued

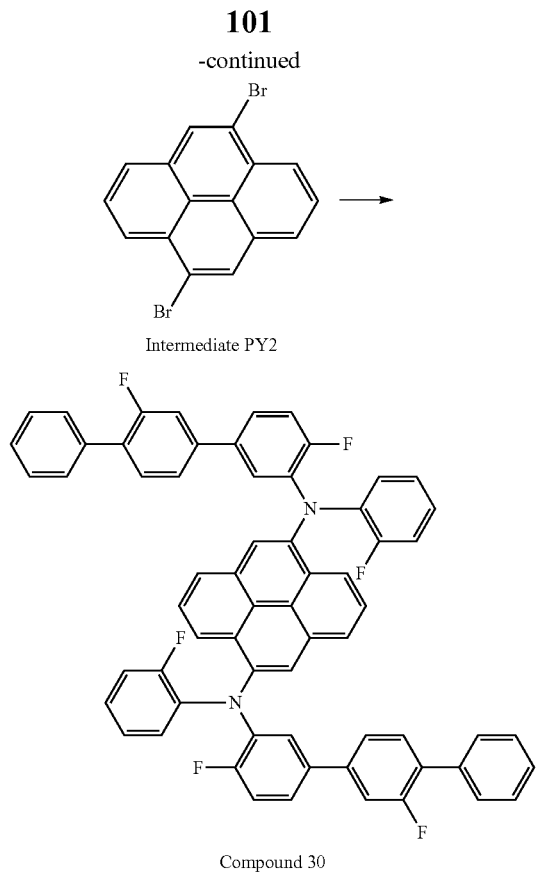

Intermediate PY2

Compound 30

In a nitrogen atmosphere, 2.7 g (7.2 mmol) of Intermediate D, 1.3 g (3.6 mmol) of Intermediate PY2, 40 mg (0A8 mmol) of Pd(OAc)$_2$, 108 mg (0.54 mmol) of P(t-Bu)$_3$, and 1.0 g (10.9 mmol) of sodium t-butoxide were added to 100 ml of toluene and refluxed for 12 hours. After the reaction was completed, the solvent was removed by evaporation, 1,000 ml of methylene chloride and 1,000 ml of water were added to wash the resultant, and an organic layer was collected and dried using magnesium sulfate anhydride. Then, the resultant was purified by recrystallization and silica gel chromatography, and 1.0 g of Compound 30 was obtained (28% yield).

H-NMR (CDCl$_3$, 300 MHz, ppm): 8.0-7.8 (m, 8H), 7.5-7.3 (m, 14H), 7.1-6.9 (m, 10H), 6.8-6.6 (m, 6H).

MS (MALDI-TOF) m/z: 948 [M]+.

Synthesis of Compound 43

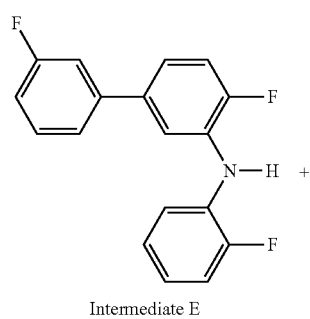

Intermediate E

-continued

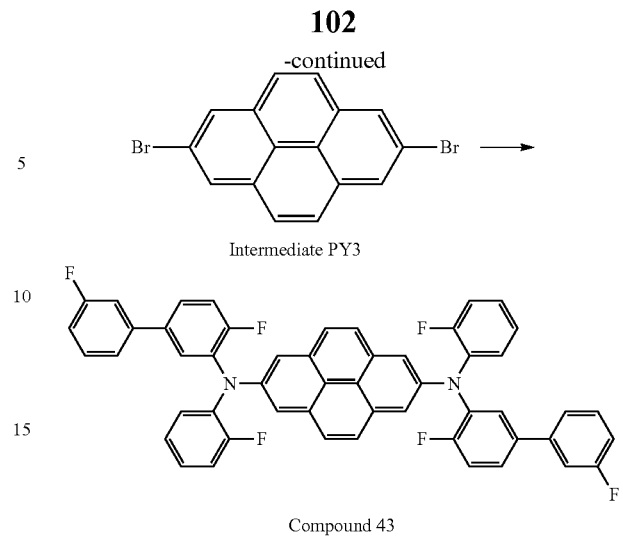

Compound 43

In a nitrogen atmosphere, 5.8 g (14.4 mmol) of Intermediate E, 2.6 g (7.2 mmol) of Intermediate PY3, 80 mg (0.36 mmol) of Pd(OAc)$_2$, 216 mg (1.08 mmol) of P(t-Bu)$_3$, and 2.0 g (21.8 mmol) of sodium t-butoxide were added to 200 ml of toluene and refluxed for 12 hours. After the reaction was completed, the solvent was removed by evaporation, 1,500 ml of methylene chloride and 1,500 ml of water were added to wash the resultant, and an organic layer was collected and dried using magnesium sulfate anhydride. Then, the resultant was purified by recrystallization and silica gel chromatography, and 2.5 g of Compound 43 was obtained (43% yield).

H-NMR (CDCl$_3$, 300 MHz, ppm): 8.0-7.3 (m, 8H), 7.1-6.9 (m, 16H), 6.8-6.6 (m, 6H).

MS (MALDI-TOF) m/z: 996 [M]+.

Example 1

A 15 Ω/cm$^2$ (1200 Å) Corning ITO glass substrate was cut into a size of 50 mm×50 mm×0.5 mm, washed with ultrasonic waves in isopropyl alcohol and pure water for 15 minutes each, and then cleaned with UV and ozone for 30 minutes. Then, the glass substrate was placed in a vacuum-deposition device.

As an anode, m-MTDATA was deposited on the ITO glass substrate at a rate of 1 Å/sec to form a HIL with a thickness of 600 Å, and then a-NPD was deposited on the HIL at a rate of 1 Å/sec to form a HTL with a thickness of 300 Å.

Next, Compound 1 (a dopant) and 9,10-di(naphthalene-2-yl)anthracene (AND, a host) were codeposited on the HTL at rates of 0.05 Å/sec and 1 Å/sec, respectively, to form an EML with a thickness of 200 Å.

Then, Alq3 was deposited on the EML to form an ETL with a thickness of 300 Å, LiF was deposited on the ETL to form an EIL with a thickness of 10 Å, and Al was deposited on the EIL to form a cathode with a thickness of 2,000 Å, thereby completing the manufacture of an OLED.

Example 2

An OLED was manufactured as in Example 1, except that Compound 5 was used as the dopant instead of Compound 1 during formation of the EML.

Example 3

An OLED was manufactured as in Example 1, except that Compound 9 was used as the dopant instead of Compound 1 during formation of the EML.

Example 4

An OLED was manufactured as in Example 1, except that Compound 23 was used as the dopant instead of Compound 1 during formation of the EML.

Example 5

An OLED was manufactured as in Example 1, except that Compound 30 was used as the dopant instead of Compound 1 during formation of the EML.

Example 6

An OLED was manufactured as in Example 1, except that Compound 43 was used as the dopant instead of Compound 1 during formation of the EML.

Comparative Example 1

An OLED was manufactured as in Example 1, except that Compound A was used as the dopant instead of Compound 1 during formation of the EML.

Compound A

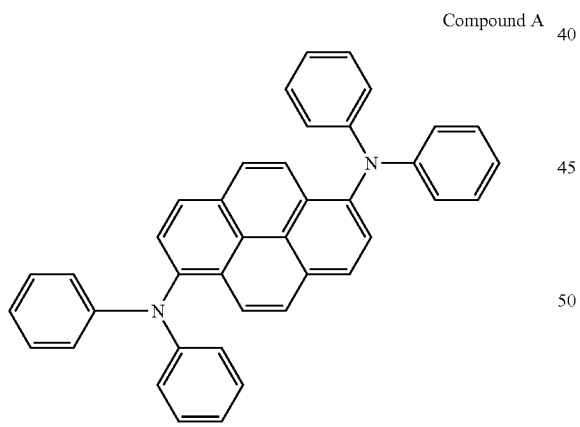

Comparative Example 2

An OLED was manufactured as in Example 1, except that Compound B was used as the dopant instead of Compound 1 during formation of the EML.

Compound B

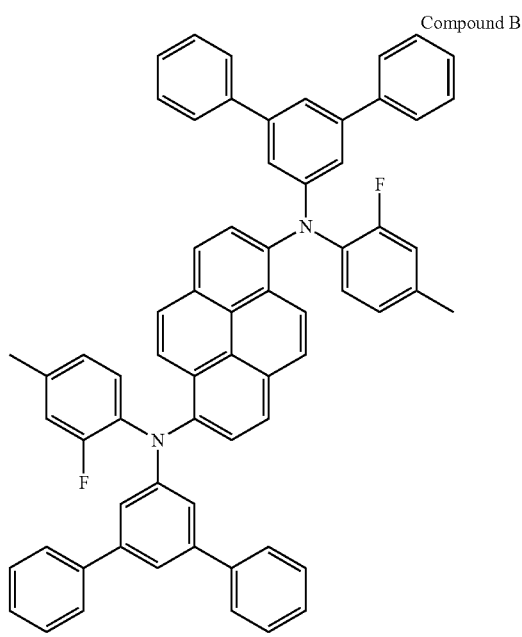 [SMILES: Cc1ccc(N(c2cc(-c3ccccc3)cc(-c3ccccc3)c2)c2ccc3ccc4c(N(c5cc(-c6ccccc6)cc(-c6ccccc6)c5)c5ccc(C)cc5F)ccc5ccc2c3c54)c(F)c1]

Comparative Example 3

An OLED was manufactured as in Example 1, except that Compound C was used as the dopant instead of Compound 1 during formation of the EML.

Compound C

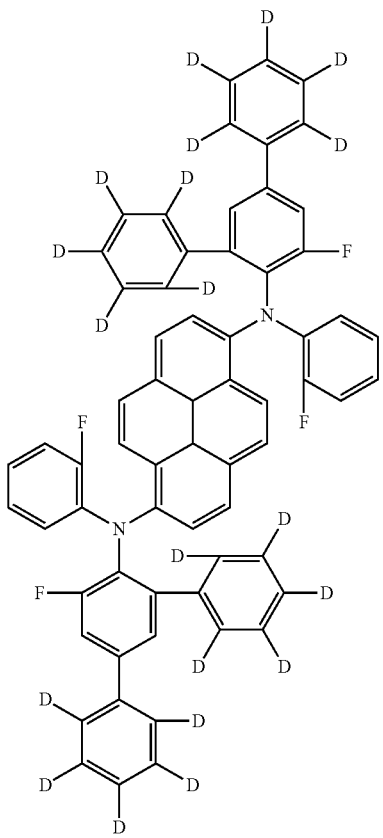

Comparative Example 4

An OLED was manufactured as in Example 1, except that Compound D was used as the dopant instead of Compound 1 during formation of the EML.

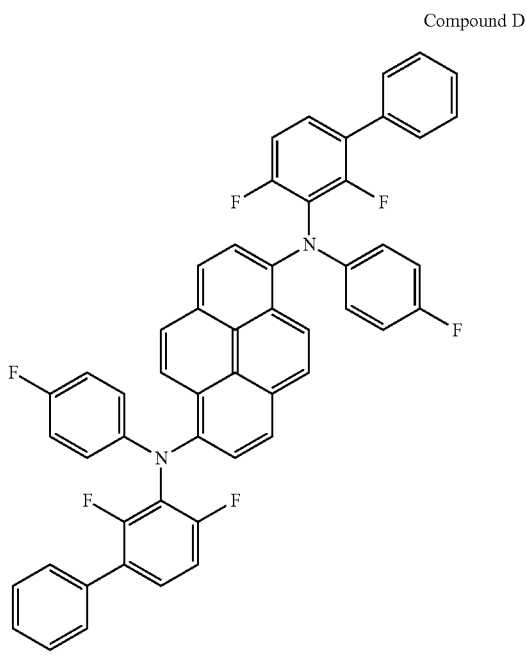 [SMILES: Fc1ccc(N(c2c(F)ccc(-c3ccccc3)c2F)c2ccc3ccc4c(N(c5ccc(F)cc5)c5c(F)ccc(-c6ccccc6)c5F)ccc5ccc2c3c54)cc1]

Compound D

Evaluation Example 1

Driving voltages, current densities, luminance, and color coordinates of the OLEDs manufactured according to Examples 1 through 6 and Comparative Examples 1 through 4 were measured using a PR650 Spectroscan Source Measurement Unit (manufactured by PhotoResearch). The results are shown in Table 1 below. IS90 lifespan indicates the time measured for luminance to be reduced to 90% compared to the initial luminance.

TABLE 1

| | EML host | EML dopant | Luminance (cd/m$^2$) | Current density (cd/A) | Driving voltage (V) | IS90 lifespan (hr) (@700nit) | Color coordinate (CIE) |
|---|---|---|---|---|---|---|---|
| Ex. 1 | ADN | Comp. 1 | 700 | 13 | 4.2 | 140 | (0.14, 0.088) |
| Ex. 2 | ADN | Comp. 5 | 700 | 11 | 4.1 | 149 | (0.14, 0.082) |
| Ex. 3 | ADN | Comp. 9 | 700 | 12 | 4.2 | 145 | (0.14, 0.085) |
| Ex. 4 | ADN | Comp. 23 | 700 | 11 | 4.2 | 133 | (0.14, 0.085) |
| Ex. 5 | ADN | Comp. 30 | 700 | 13 | 4.1 | 110 | (0.14, 0.085) |
| Ex. 6 | ADN | Comp. 43 | 700 | 14 | 4.2 | 124 | (0.14, 0.089) |
| Comp. Ex. 1 | ADN | Comp. A | 700 | 16 | 4.6 | 61 | (0.16, 0.20) |
| Comp. Ex. 2 | ADN | Comp. B | 700 | 15 | 4.6 | 67 | (0.14, 0.13) |
| Comp. Ex. 3 | ADN | Comp. C | 700 | 16 | 4.5 | 55 | (0.14, 0.14) |
| Comp. Ex. 4 | ADN | Comp. D | 700 | 15 | 4.6 | 40 | (0.14, 0.12) |

From the results shown in Table 1, it may be confirmed that the OLEDs of Examples 1 through 6 have good driving voltage, current density, and color purity characteristics, as compared to the OLEDs of Comparative Examples 1 through 4.

As described above, an OLED including a pyrene-based compound, and an organic light-emitting apparatus may have low driving voltage, high current density, and good color purity.

While certain embodiments of the present invention have been illustrated and described, it will be understood by those of ordinary skill in the art that various changes and modifications can be made to the described embodiments without departing from the spirit and scope of the present invention as defined by the following claims.

What is claimed is:

1. A pyrene-based compound represented by Formula 1:

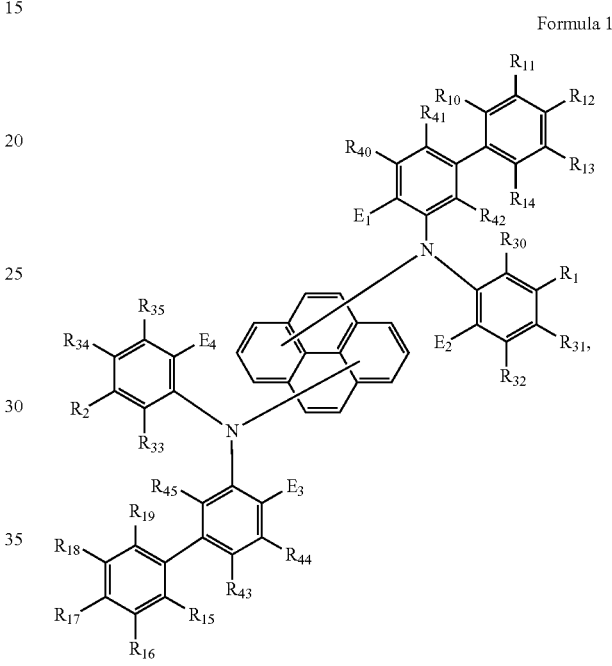

Formula 1 wherein in Formula 1,
each of $E_1$ to $E_4$ is independently —F; —CN; or a $C_1$-$C_{60}$ alkyl group substituted with at least one —F;
each of $R_1$, $R_2$, $R_{10}$ to $R_{19}$, $R_{30}$ to $R_{35}$, and $R_{40}$ to $R_{45}$ is independently one of hydrogen; deuterium; —F; —Cl; —Br; —I; —CN; a hydroxyl group; a nitro group; an amino group; an amidino group; hydrazine; hydrazone;

a carboxyl group or a salt thereof; a sulfonic acid group or a salt thereof; a phosphoric acid group or a salt thereof; a $C_1$-$C_{60}$ alkyl group, a $C_1$-$C_{60}$ alkoxy group, a $C_2$-$C_{60}$ alkenyl group, a $C_2$-$C_{60}$ alkynyl group; a $C_1$-$C_{60}$ alkyl group, a $C_1$-$C_{60}$ alkoxy group, a $C_2$-$C_{60}$ alkenyl group, or a $C_2$-$C_{60}$ alkynyl group substituted with at least one of deuterium, —F, —Cl, —Br, —I, —CN, a hydroxyl group, a nitro group, an amino group, an amidino group, hydrazine, hydrazone, a carboxyl group or a salt thereof, a sulfonic acid group or a salt thereof, or a phosphoric acid group or a salt thereof; a $C_3$-$C_{60}$ cycloalkyl group, a $C_3$-$C_{60}$ cycloalkenyl group, a $C_6$-$C_{60}$ aryl group, a $C_2$-$C_{60}$ heteroaryl group, a $C_6$-$C_{60}$ aralkyl group, a $C_6$-$C_{60}$ aryloxy group, or a $C_6$-$C_{60}$ arylthio group; $C_3$-$C_{60}$ cycloalkyl group, $C_3$-$C_{60}$ cycloalkenyl group, $C_6$-$C_{60}$ aryl group, $C_2$-$C_{60}$ heteroaryl group, $C_6$-$C_{60}$ aralkyl group, $C_6$-$C_{60}$ aryloxy group, or a $C_6$-$C_{60}$ arylthio group substituted with at least one of deuterium, —F, —Cl, —Br, —I, —CN, a hydroxyl group, a nitro group, an amino group, an amidino group, hydrazine, hydrazone, a carboxyl group or a salt thereof, a sulfonic acid group or a salt thereof, a phosphoric acid group or a salt thereof, a $C_1$-$C_{60}$ alkyl group, a $C_1$-$C_{60}$ alkyl group substituted with at least one —F, a $C_1$-$C_{60}$ alkoxy group, a $C_2$-$C_{60}$ alkenyl group, a $C_2$-$C_{60}$ alkynyl group, a $C_6$-$C_{60}$ aryl group, a $C_6$-$C_{60}$ aryl group substituted with at least one —F, or a $C_2$-$C_{60}$ heteroaryl group; —N($Q_1$)($Q_2$); or —Si($Q_3$)($Q_4$)($Q_5$) where each of $Q_1$ to $Q_5$ is independently one of a $C_1$-$C_{60}$ alkyl group, a $C_1$-$C_{60}$ alkoxy group, a $C_2$-$C_{60}$ alkenyl group, a $C_2$-$C_{60}$ alkynyl group, a $C_3$-$C_{60}$ cycloalkyl group, a $C_3$-$C_{60}$ cycloalkenyl group, a $C_6$-$C_{60}$ aryl group, a $C_2$-$C_{60}$ heteroaryl group, a $C_6$-$C_{60}$ aralkyl group, a $C_6$-$C_{60}$ aryloxy group, or a $C_6$-$C_{60}$ arylthio group; and wherein at least one of $R_1$, $R_{10}$ to $R_{14}$ and $R_{30}$ to $R_{32}$, and at least one of $R_2$, $R_{15}$ to $R_{19}$ and $R_{33}$ to $R_{35}$ are independently selected from the group consisting of —F; —CN; a $C_1$-$C_{60}$ alkyl group substituted with at least one —F; and a $C_6$-$C_{60}$ aryl group substituted with at least one of —F, —CN, and a $C_1$-$C_{60}$ alkyl group substituted with at least one —F.

2. The pyrene-based compound of claim 1, wherein $E_1$ to $E_4$ are all —F.

3. The pyrene-based compound of claim 1, wherein at least one of $R_{10}$ to $R_{14}$ and at least one of $R_{15}$ to $R_{19}$ are independently selected from the group consisting of —F; —CN; a $C_1$-$C_{20}$ alkyl group substituted with at least one —F; and a $C_6$-$C_{20}$ aryl group substituted with at least one of —F, —CN, and a $C_1$-$C_{20}$ alkyl group substituted with at least one —F.

4. The pyrene-based compound of claim 1, wherein at least one of $R_{10}$ to $R_{14}$ and at least one of $R_{15}$ to $R_{19}$ are independently selected from the group consisting of —F; —CN; a $C_1$-$C_{10}$ alkyl group substituted with at least one —F; and a phenyl group, a naphthyl group, and an anthryl group substituted with at least one of —F, —CN, and a $C_1$-$C_{10}$ alkyl group substituted with at least one —F.

5. The pyrene-based compound of claim 1, wherein each of $E_1$ to $E_4$ is independently —F; —CN; or a $C_1$-$C_{10}$ alkyl group substituted with at least one —F; and each of $R_1$, $R_2$, $R_{10}$ to $R_{19}$, $R_{30}$ to $R_{35}$, and $R_{40}$ to $R_{45}$ is independently one of hydrogen; deuterium; —F; —Cl; —Br; —I; —CN; a hydroxyl group; a nitro group; an amino group; an amidino group; hydrazine; hydrazone; a carboxyl group or a salt thereof; a sulfonic acid group or a salt thereof; a phosphoric acid group or a salt thereof; a $C_1$-$C_{10}$ alkyl group and a $C_1$-$C_{10}$ alkoxy group; a $C_1$-$C_{10}$ alkyl group or a $C_1$-$C_{10}$ alkoxy group substituted with at least one of deuterium, —F, —Cl, —Br, —I, —CN, a hydroxyl group, a nitro group, an amino group, an amidino group, hydrazine, hydrazone, a carboxyl group or a salt thereof, a sulfonic acid group or a salt thereof, or a phosphoric acid group or a salt thereof; a phenyl group, a naphthyl group, an anthryl group, a fluorenyl group, a dibenzofuranyl group, or a dibenzothiophenyl group; or a phenyl group, a naphthyl group, an anthryl group, a fluorenyl group, a dibenzofuranyl group, or a dibenzothiophenyl group substituted with at least one of deuterium, —F, —Cl, —Br, —I, —CN, a hydroxyl group, a nitro group, an amino group, an amidino group, hydrazine, hydrazone, a carboxyl group or a salt thereof, a sulfonic acid group or a salt thereof, a phosphoric acid group or a salt thereof, a $C_1$-$C_{10}$ alkyl group, a $C_1$-$C_{10}$ alkyl group substituted with at least one —F, a $C_1$-$C_{10}$ alkoxy group, or a phenyl group substituted with at least one —F, wherein at least one of $R_1$, $R_{10}$ to $R_{14}$, and $R_{30}$ to $R_{32}$ and at least one of $R_2$, $R_{15}$ to $R_{19}$, and $R_{33}$ to $R_{35}$ are independently selected from the group consisting of —F; —CN; a $C_1$-$C_{10}$ alkyl group substituted with at least one —F; and a phenyl group, a naphthyl group, and an anthryl group that are substituted with at least one of —F, —CN, and a $C_1$-$C_{10}$ alkyl group substituted with at least one —F.

6. The pyrene-based compound of claim 1, wherein each of $R_1$ and $R_2$ is independently one of a phenyl group, a naphthyl group or an anthryl group; or a phenyl group, a naphthyl group or an anthryl group substituted with at least one of —F, —CN, or a $C_1$-$C_{10}$ alkyl group substituted with at least one —F, or a phenyl group substituted with at least one —F.

7. The pyrene-based compound of claim 1, wherein in Formula 1,

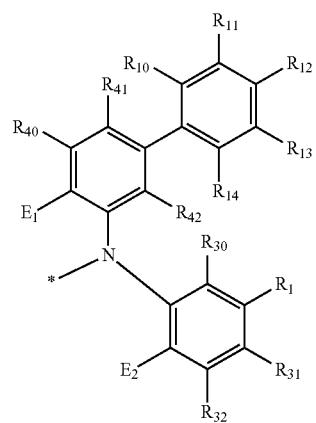

is a first diarylamino group, and

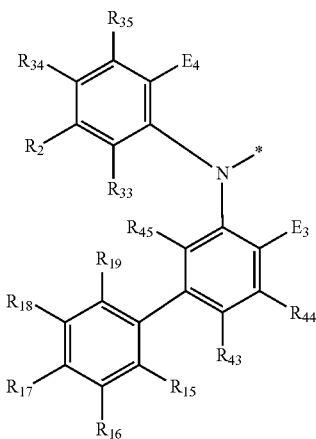

is a second diarylamino group, and the first and second diarylamino groups are identical to each other.

8. The pyrene-based compound of claim 1, wherein in Formula 1,

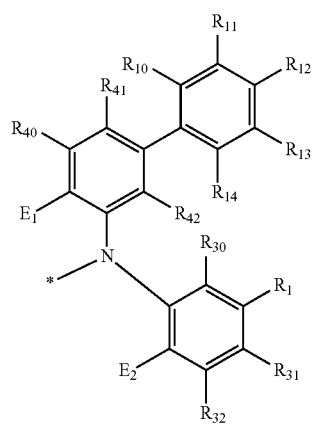

is a first diarylamino group, and

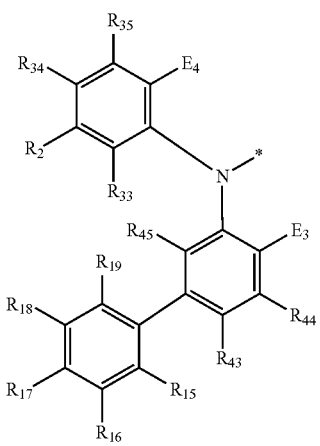

is a second diarylamino group, and the first and second diarylamino groups are different from each other.

9. The pyrene-based compound of claim 1, wherein the pyrene-based compound is represented by any one of Formulae 1A, 1B, or 1C:

Formula 1A

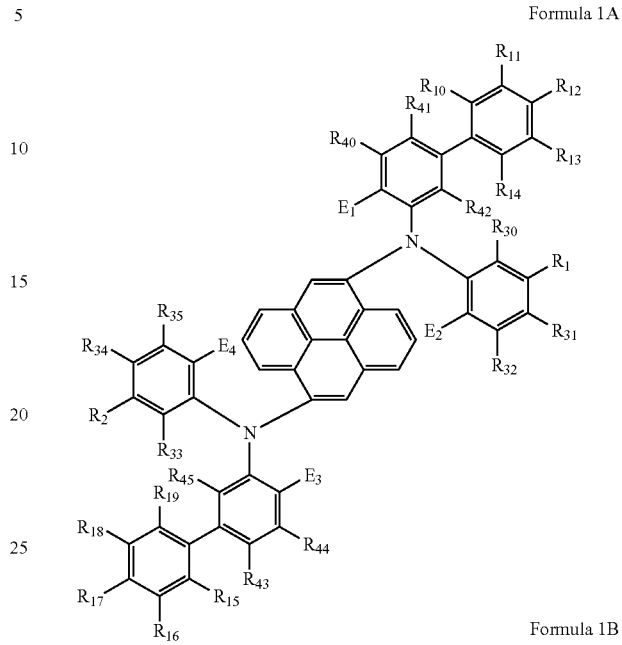

Formula 1B

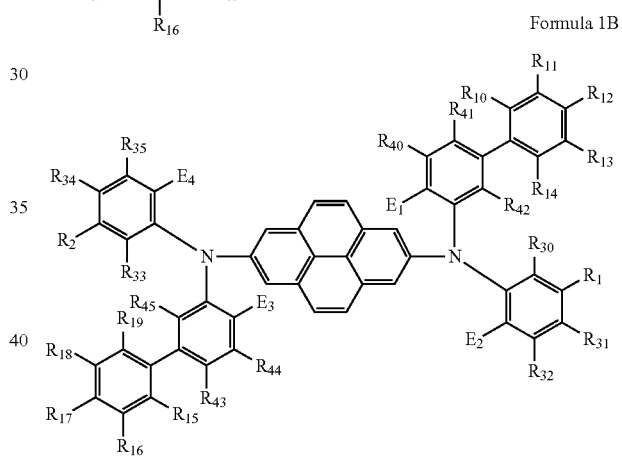

Formula 1C

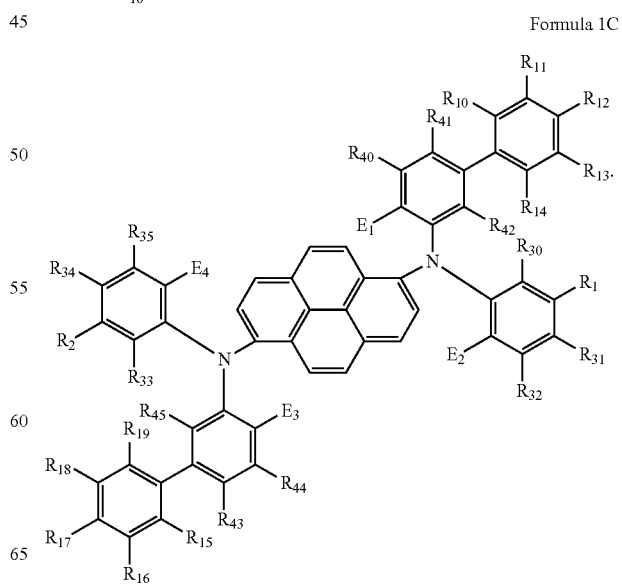

10. The pyrene-based compound of claim 1, wherein the pyrene-based compound is represented by Formula 1-(1) or 1-(2) below:

Formula 1-(1)

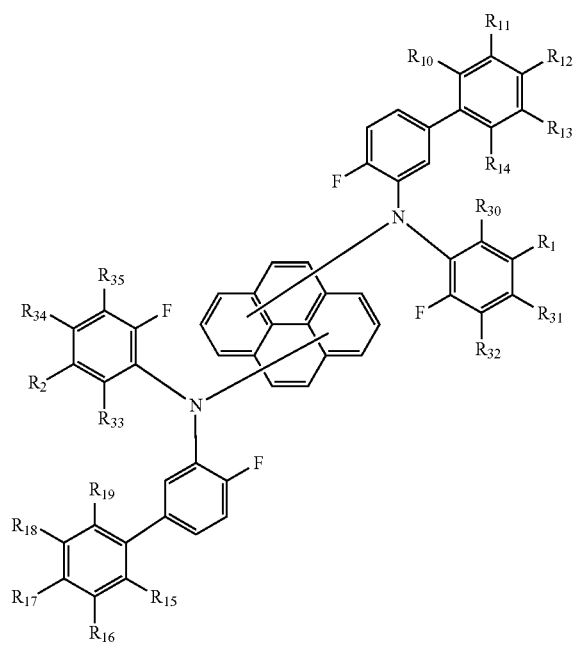

<Formula 1-(2)>

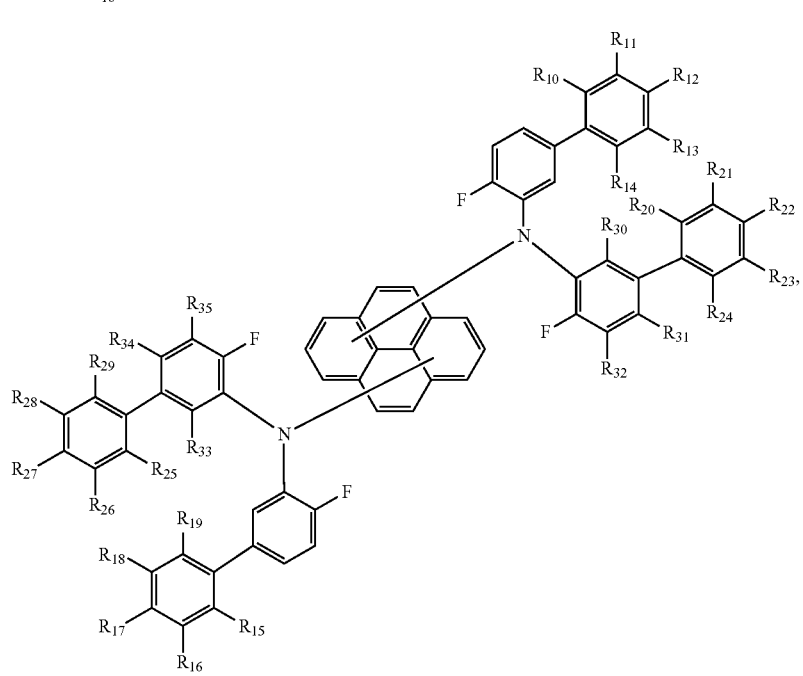

wherein each of $R_{20}$ to $R_{29}$ is independently one of hydrogen; deuterium; —F; —Cl; —Br; —I; —CN; a hydroxyl group; a nitro group; an amino group; an amidino group; hydrazine; hydrazone; a carboxyl group or a salt thereof; a sulfonic acid group or a salt thereof; a phosphoric acid group or a salt thereof; a $C_1$-$C_{60}$ alkyl group, a $C_1$-$C_{60}$ alkoxy group, a $C_2$-$C_{60}$ alkenyl group, a $C_2$-$C_{60}$ alkynyl group; a $C_1$-$C_{60}$ alkyl group, a $C_1$-$C_{60}$ alkoxy group, a $C_2$-$C_{60}$ alkenyl group, or a $C_2$-$C_{60}$ alkynyl group substituted with at least one of deuterium, —F, —Cl, —Br, —I, —CN, a hydroxyl group, a nitro group, an amino group, an amidino group, hydrazine, hydrazone, a carboxyl group or a salt thereof, a sulfonic acid group or a salt thereof, or a phosphoric acid group or a salt thereof; a $C_3$-$C_{60}$ cycloalkyl group, a $C_3$-$C_{60}$ cycloalkenyl group, a $C_6$-$C_{60}$ aryl group, a $C_2$-$C_{60}$ heteroaryl group, a $C_6$-$C_{60}$ aralkyl group, a $C_6$-$C_{60}$ aryloxy group, or a $C_6$-$C_{60}$ arylthio group; $C_3$-$C_{60}$ cycloalkyl group, $C_3$-$C_{60}$ cycloalkenyl group, $C_6$-$C_{60}$ aryl group, $C_2$-$C_{60}$ heteroaryl group, $C_6$-$C_{60}$ aralkyl group, $C_6$-$C_{60}$ aryloxy group, or a $C_6$-$C_{60}$ arylthio group substituted with at least one of deuterium, —F, —Cl, —Br, —I, —CN, a hydroxyl group, a nitro group, an amino group, an amidino group, hydrazine, hydrazone, a carboxyl group or a salt thereof, a sulfonic acid group or a salt thereof, a phosphoric acid group or a salt thereof, a $C_1$-$C_{60}$ alkyl group, a $C_1$-$C_{60}$ alkyl group substituted with at least one —F, a $C_1$-$C_{60}$ alkoxy group, a $C_2$-$C_{60}$ alkenyl group, a $C_2$-$C_{60}$ alkynyl group, a $C_6$-$C_{60}$ aryl group, a $C_6$-$C_{60}$ aryl group substituted with at least one —F, or a $C_2$-$C_{60}$ heteroaryl group; —N($Q_1$)($Q_2$); or —Si($Q_3$)($Q_4$)($Q_5$) where each of $Q_1$ to $Q_5$ is independently one of a $C_1$-$C_{60}$ alkyl group, a $C_1$-$C_{60}$ alkoxy group, a $C_2$-$C_{60}$ alkenyl group, a $C_2$-$C_{60}$ alkynyl group, a $C_3$-$C_{60}$ cycloalkyl group, a $C_3$-$C_{60}$ cycloalkenyl group, a $C_6$-$C_{60}$ aryl group, a $C_2$-$C_{60}$ heteroaryl group, a $C_6$-$C_{60}$ aralkyl group, a $C_6$-$C_{60}$ aryloxy group, or a $C_6$-$C_{60}$ arylthio group.

11. The pyrene-based compound of claim 10, wherein in Formulae 1-(1) and 1-(2), at least one of $R_{10}$ to $R_{14}$ and at least one of $R_{15}$ to $R_{19}$ are independently selected from the group consisting of —F; —CN; a $C_1$-$C_{10}$ alkyl group substituted with at least one —F; and a phenyl group, a naphthyl group, and an anthryl group that are substituted with at least one of —F, —CN, and a $C_1$-$C_{10}$ alkyl group substituted with at least one —F.

12. The pyrene-based compound of claim 10, wherein the pyrene-based compound is represented by Formula 1-(1) above, and in Formulae 1-(1), at least one of $R_{20}$ to $R_{24}$ and at least one of $R_{25}$ to $R_{29}$ are independently selected from the group consisting of —F; —CN; a $C_1$-$C_{10}$ alkyl group; a $C_1$-$C_{10}$ alkyl group substituted with at least one —F; and a phenyl group, a naphthyl group, and an anthryl group.

13. The pyrene-based compound of claim 10, wherein the pyrene-based compound is represented by Formula 1-(2) above, and in Formulae 1-(2), at least one of $R_{20}$ to $R_{24}$ and at least one of $R_{25}$ to $R_{29}$ are independently selected from the group consisting of —F; —CN; a $C_1$-$C_{10}$ alkyl group; a $C_1$-$C_{10}$ alkyl group substituted with at least one —F; a phenyl group, a naphthyl group, and an anthryl group; and a phenyl group, a naphthyl group, and an anthryl group that are substituted with at least one of —F, and —CN.

14. The pyrene-based compound of claim 1, wherein the pyrene-based compound is one of Compounds 1 to 50:

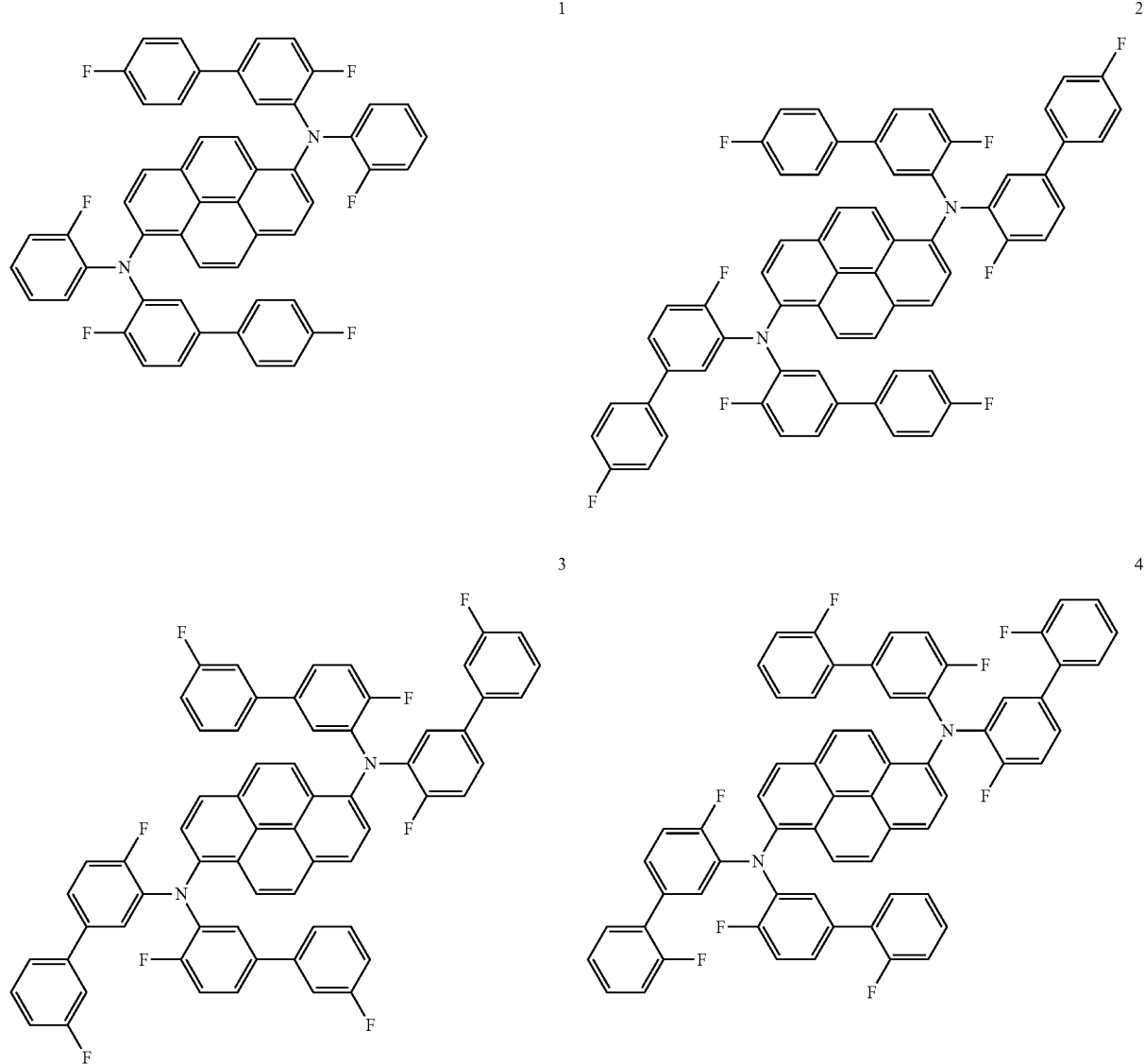

-continued
5
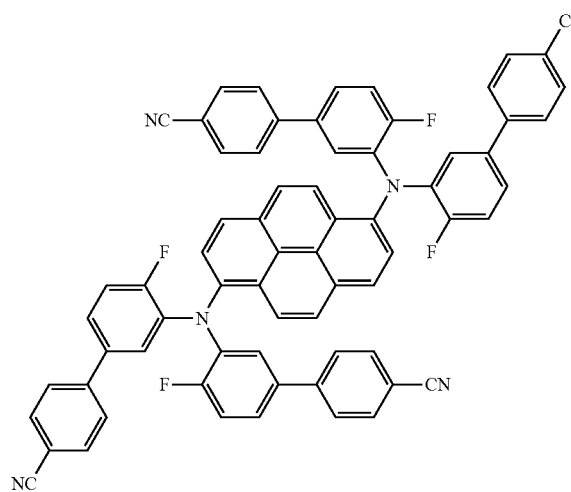
6
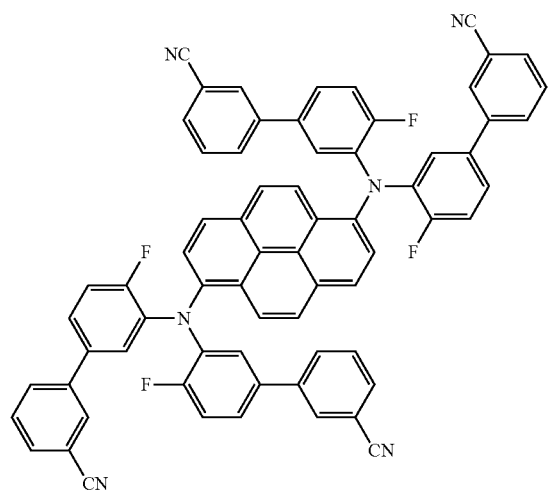
7
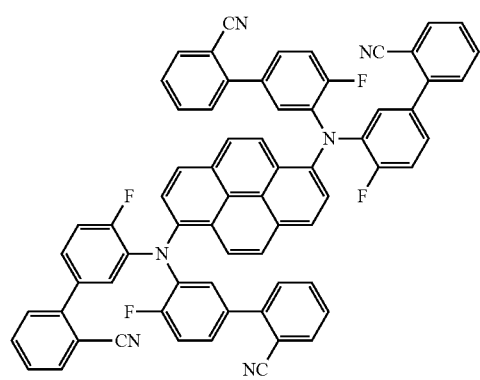
8
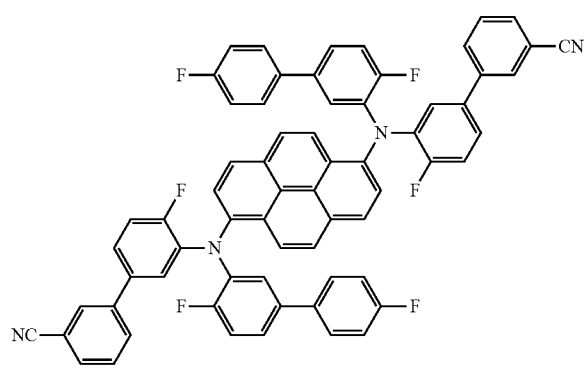
9
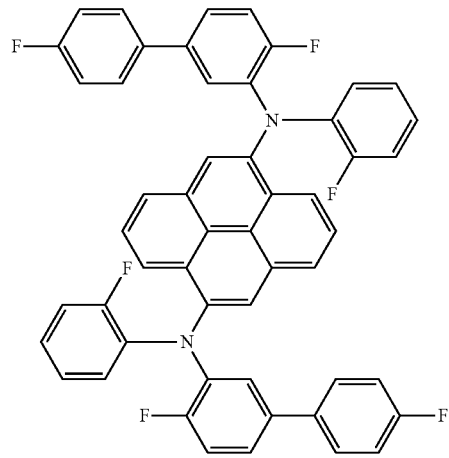
10
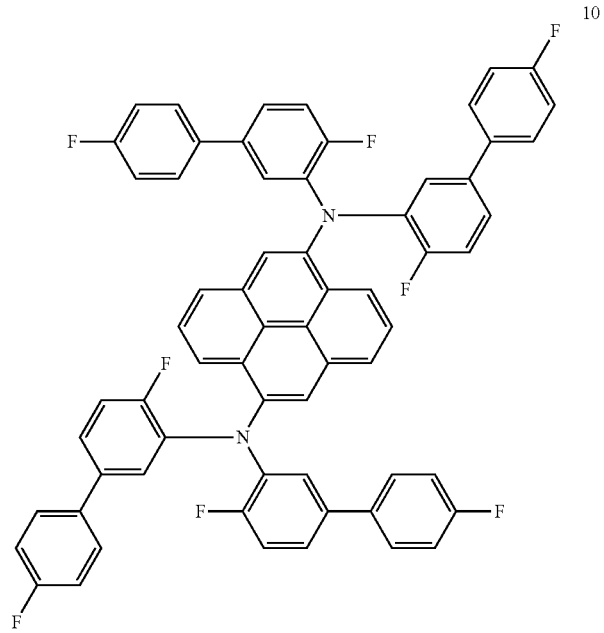

-continued
11
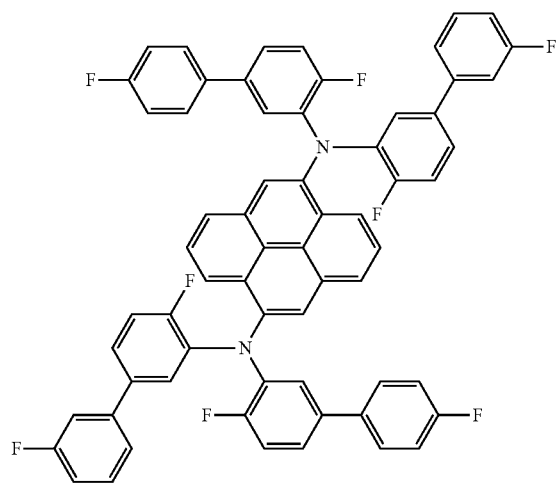
12
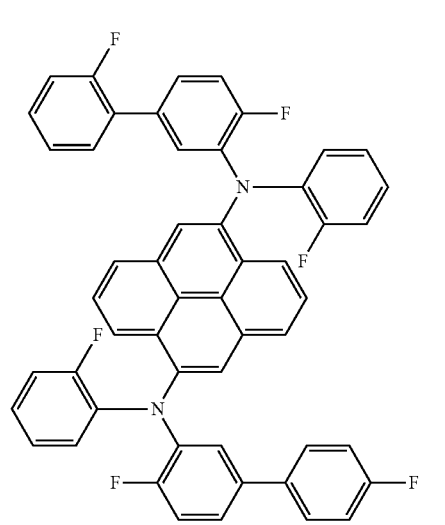
13
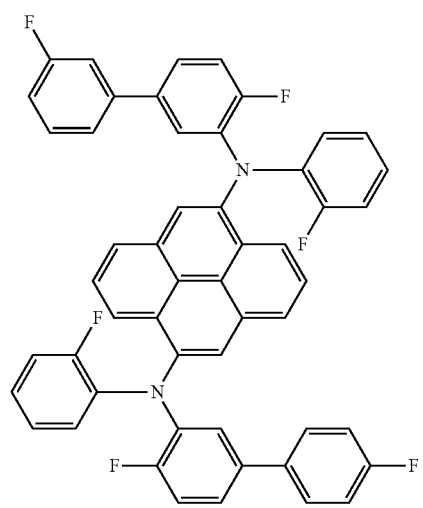
14
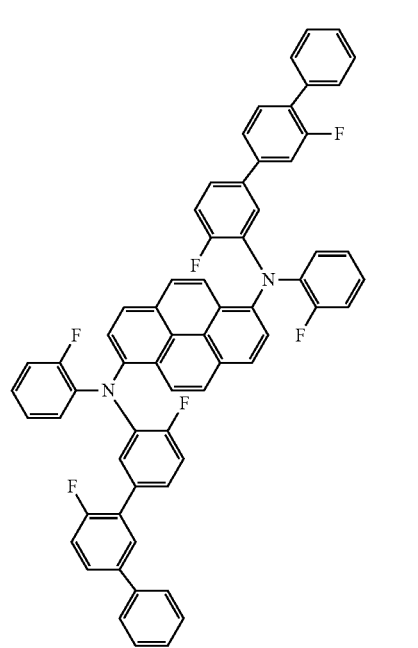
15
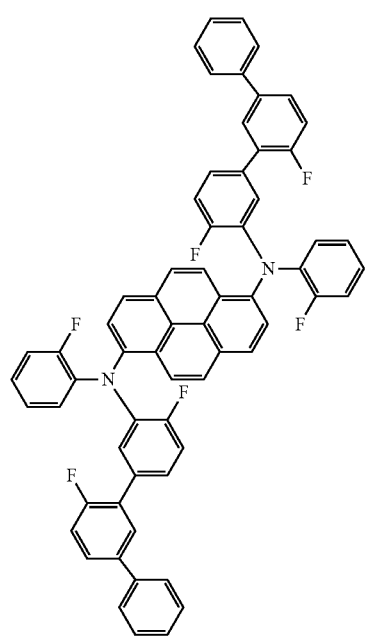
16

-continued
17
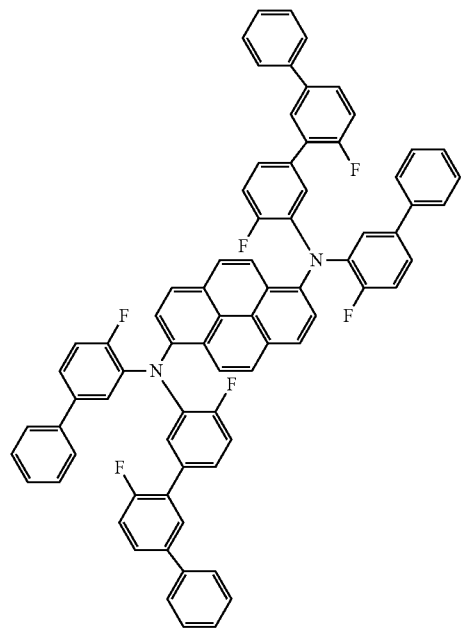
18
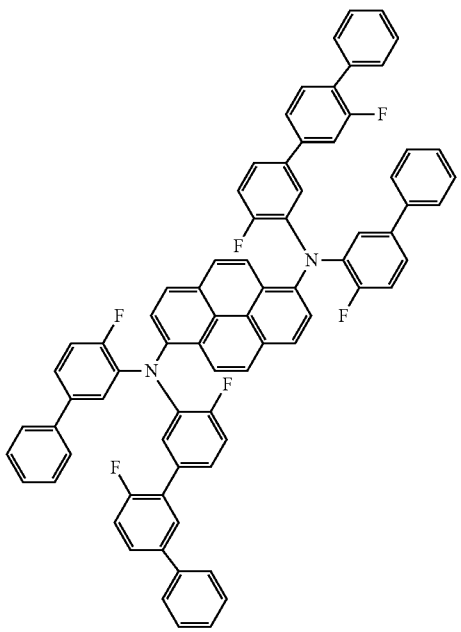
19
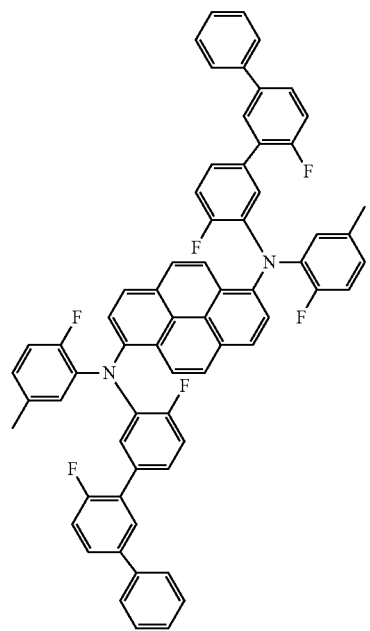
20
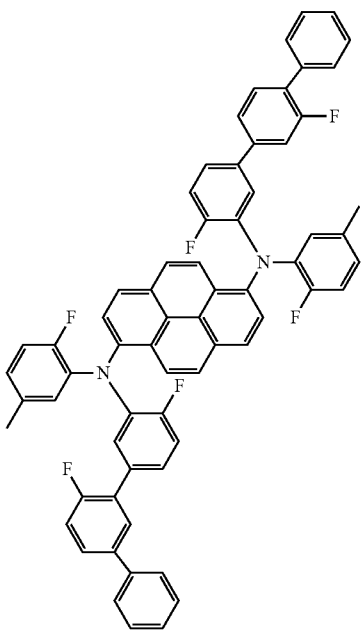

-continued
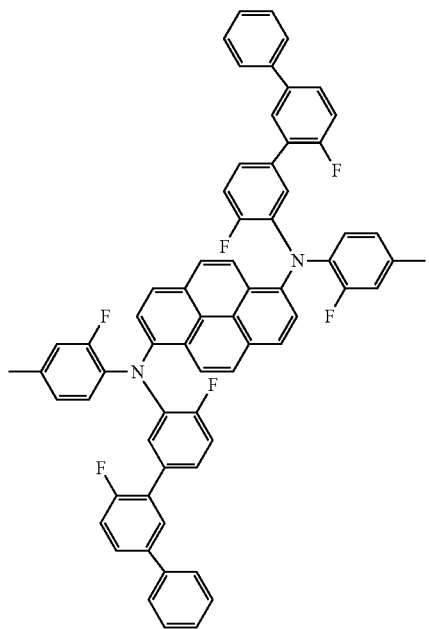
21
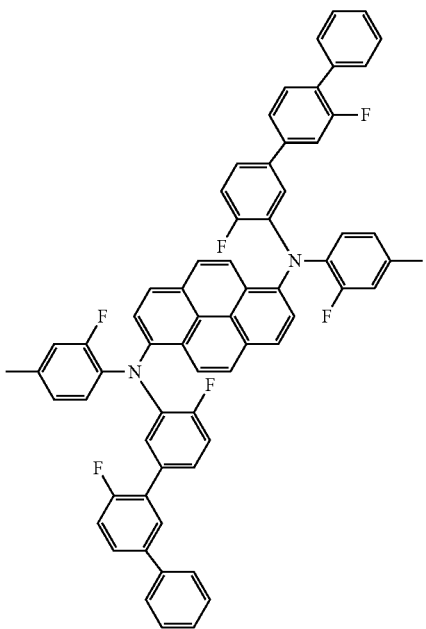
22
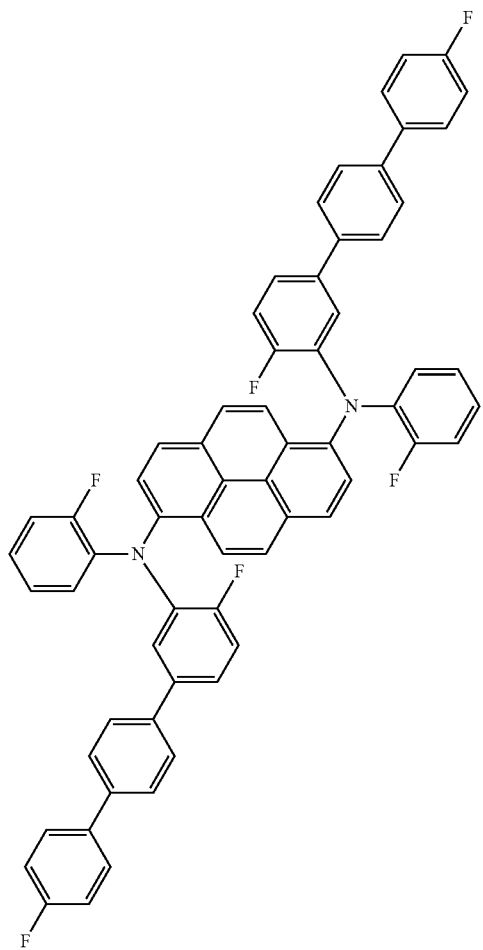
23
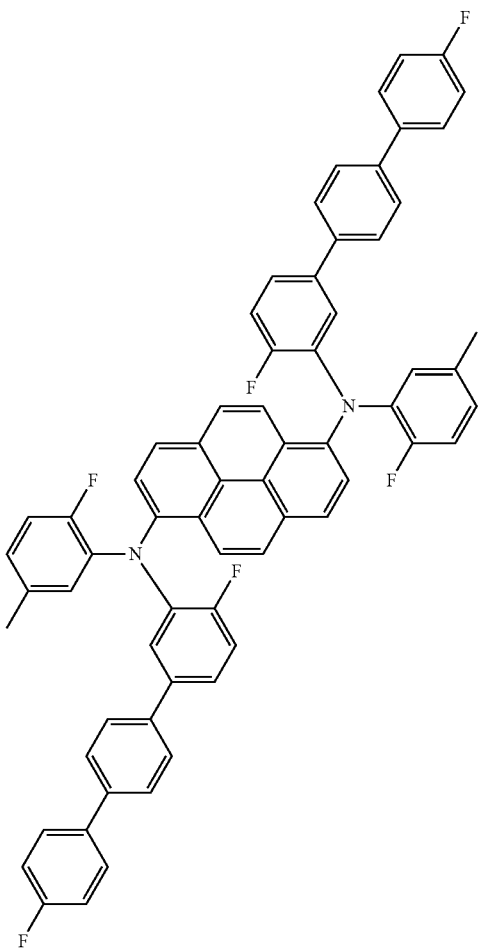
24

123
124
-continued
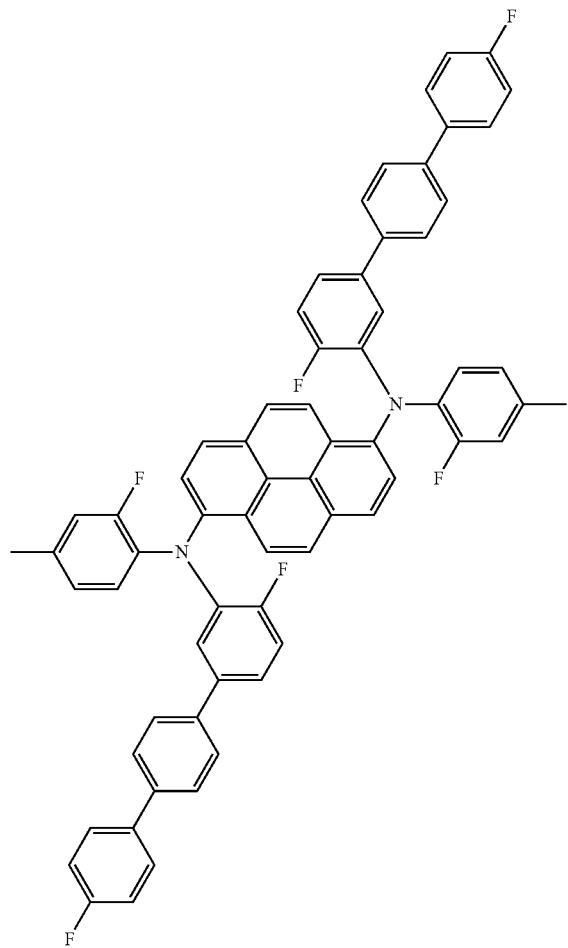
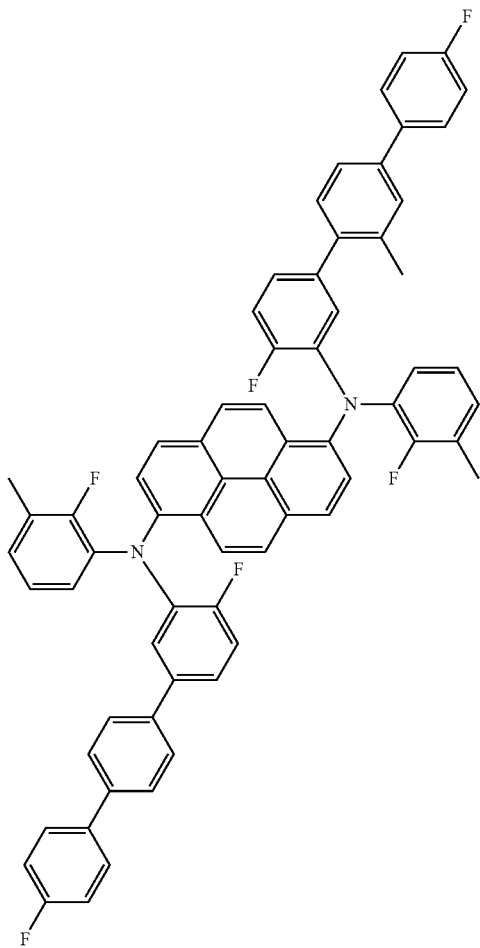

27
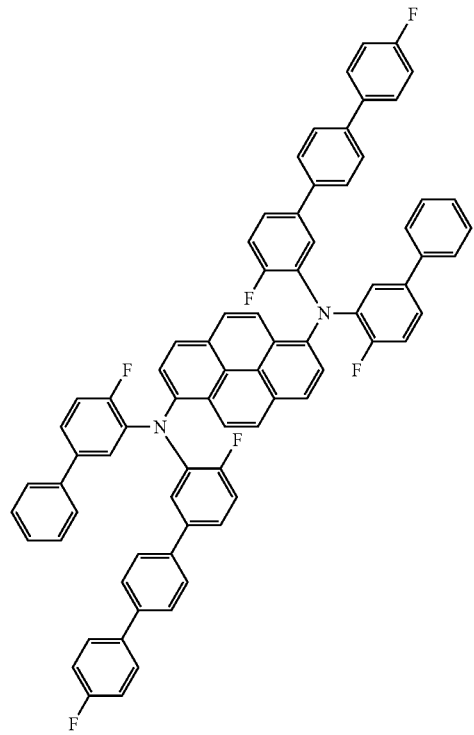
28
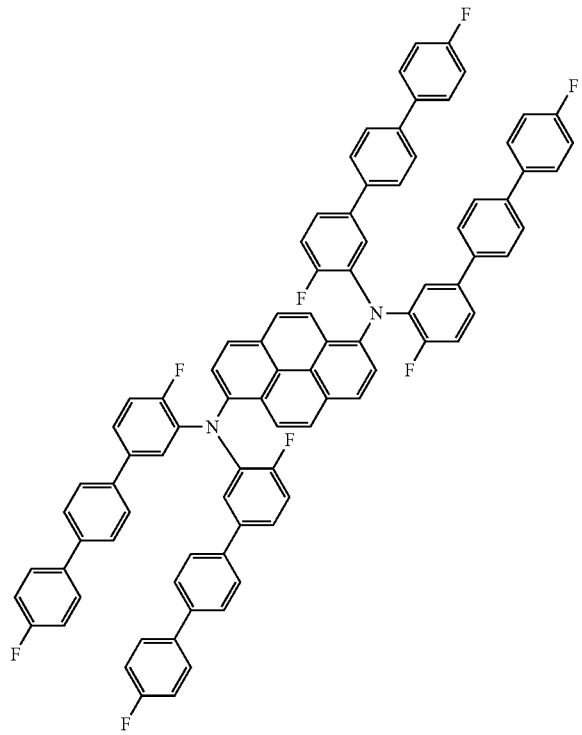
29
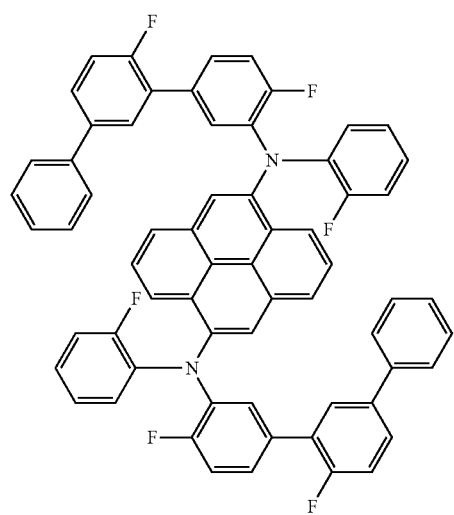
30
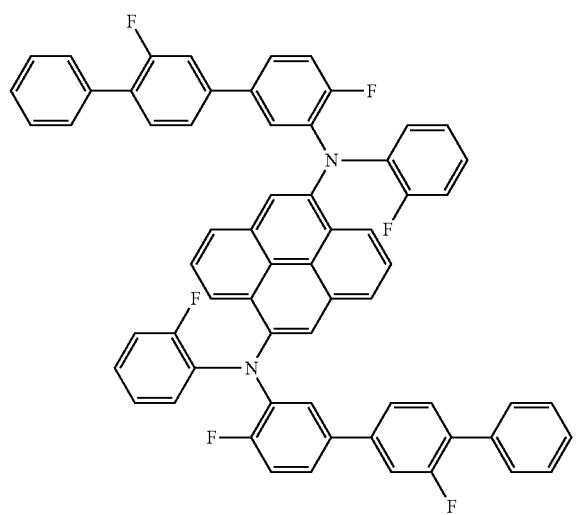

-continued
31
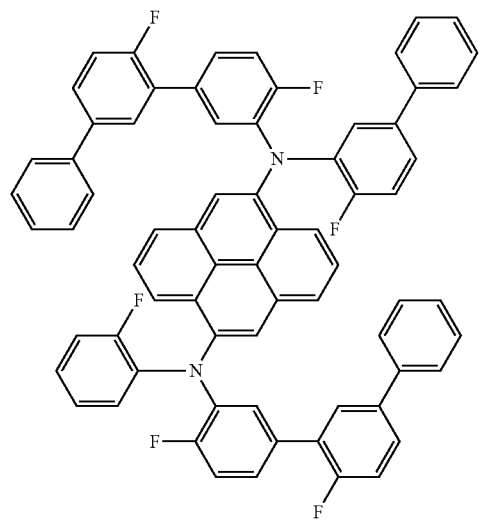
32
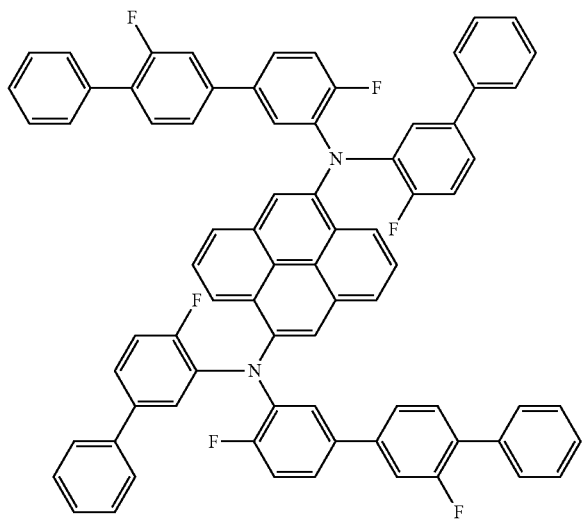
33
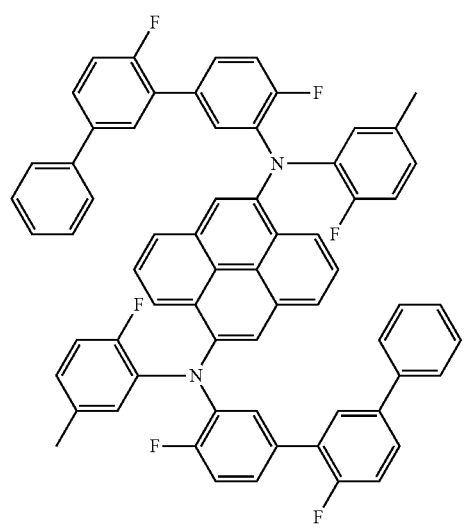
34
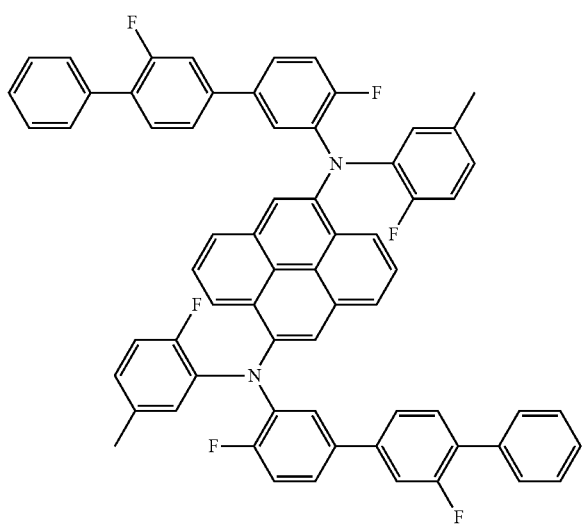
35
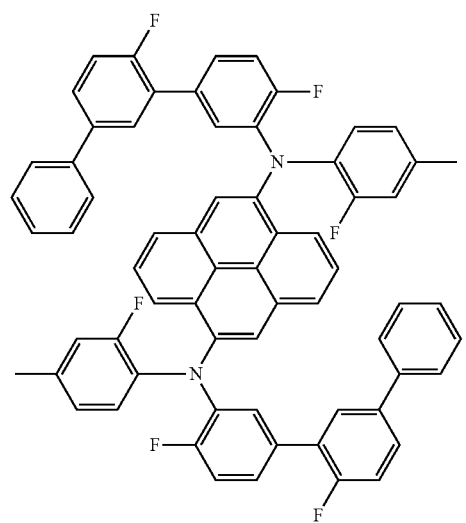
36
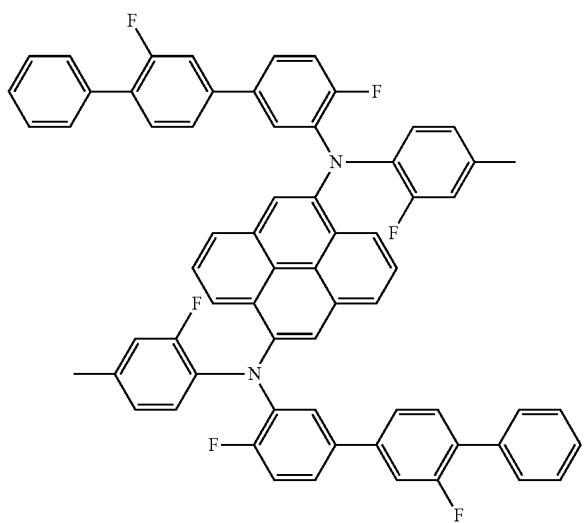

-continued
37
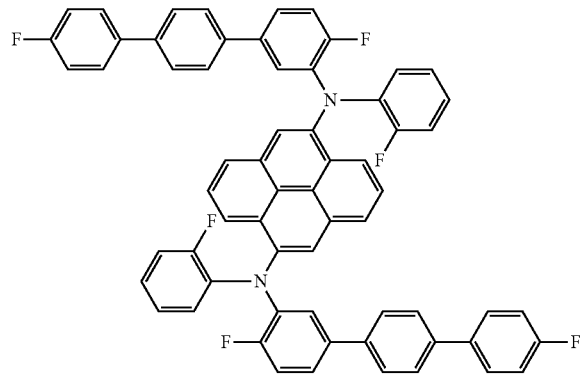
38
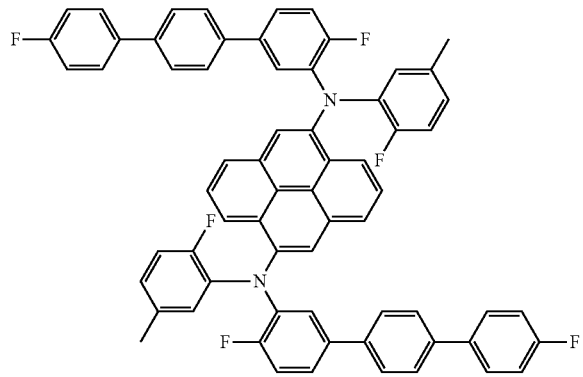
39
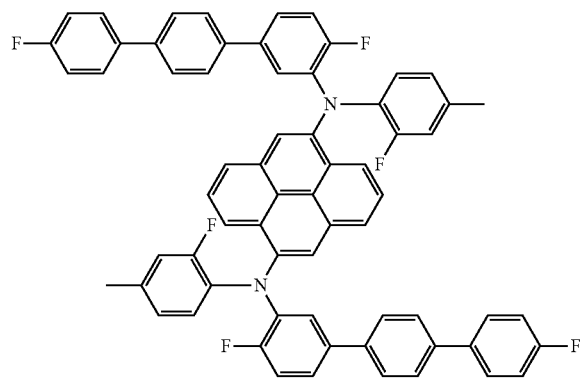
40
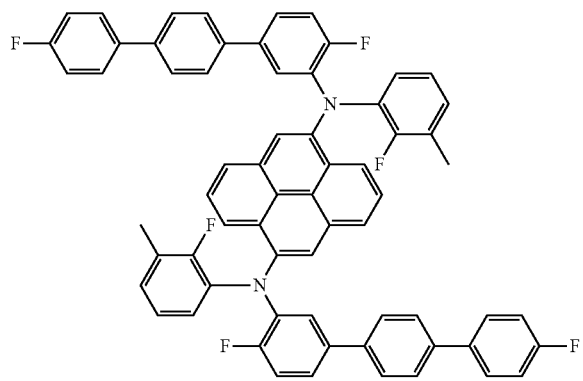
41
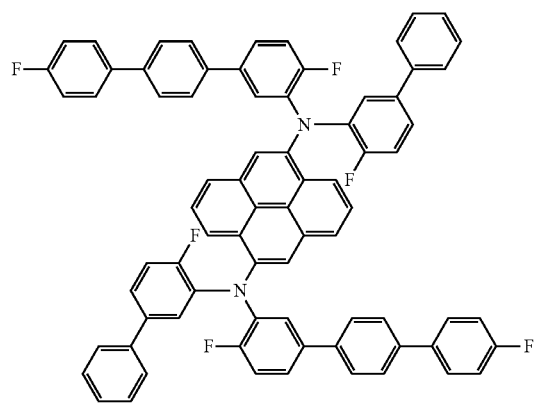
42
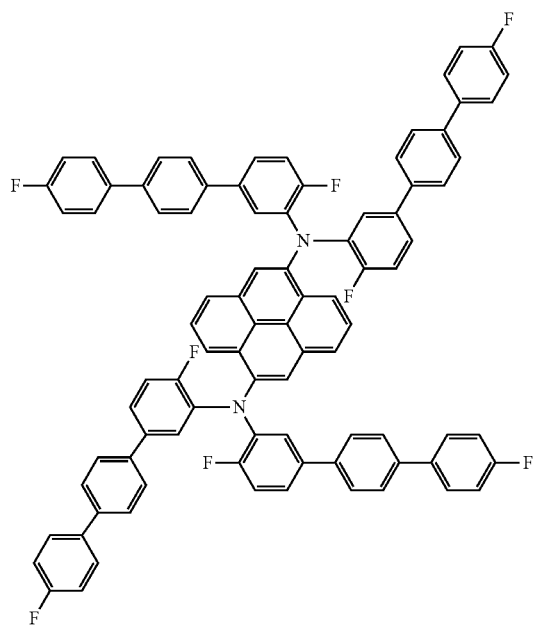

-continued
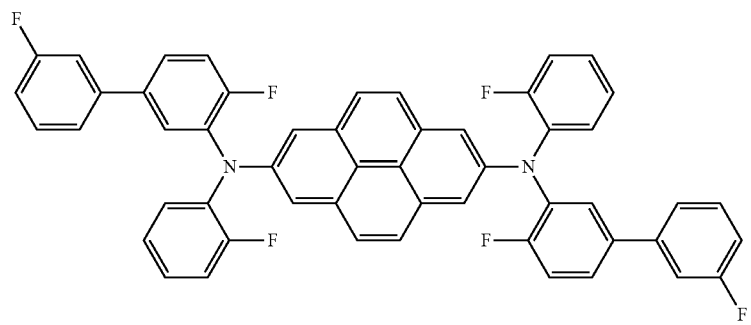
43
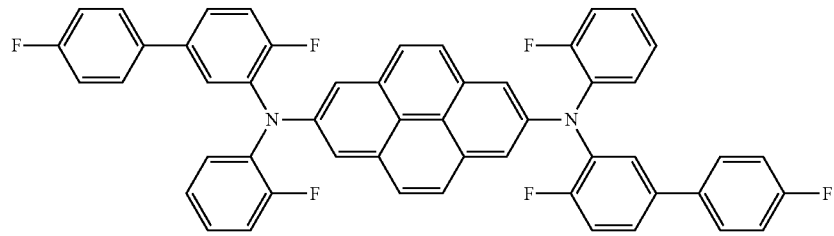
44
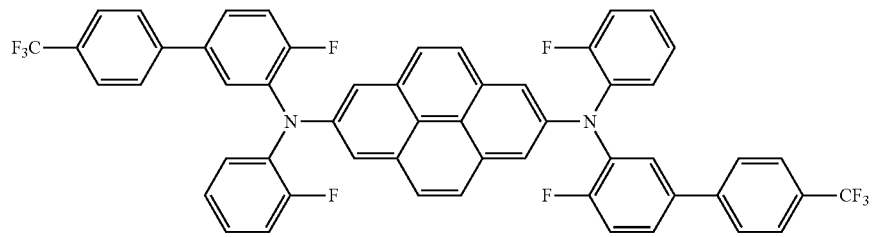
45
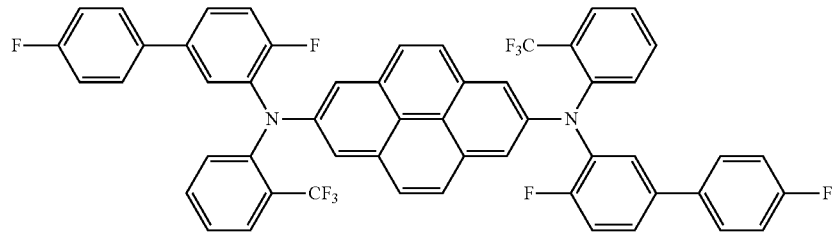
46
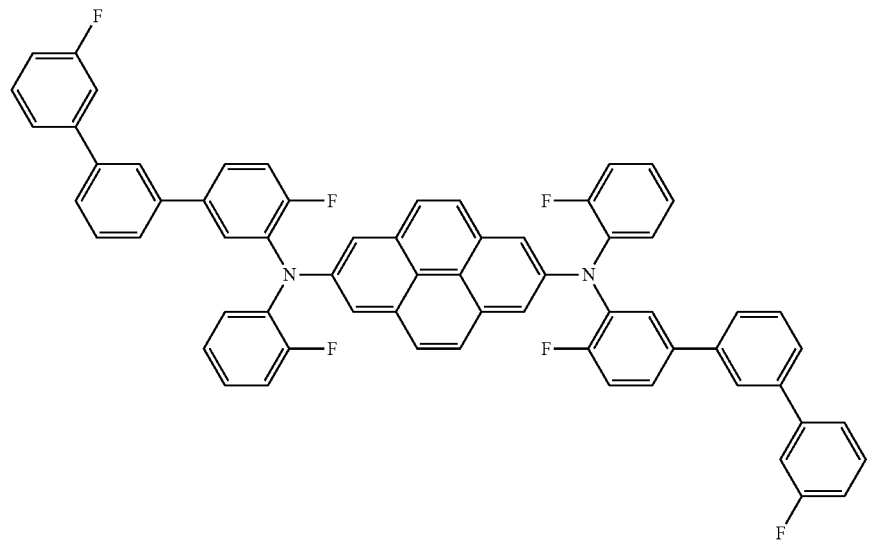
47

-continued

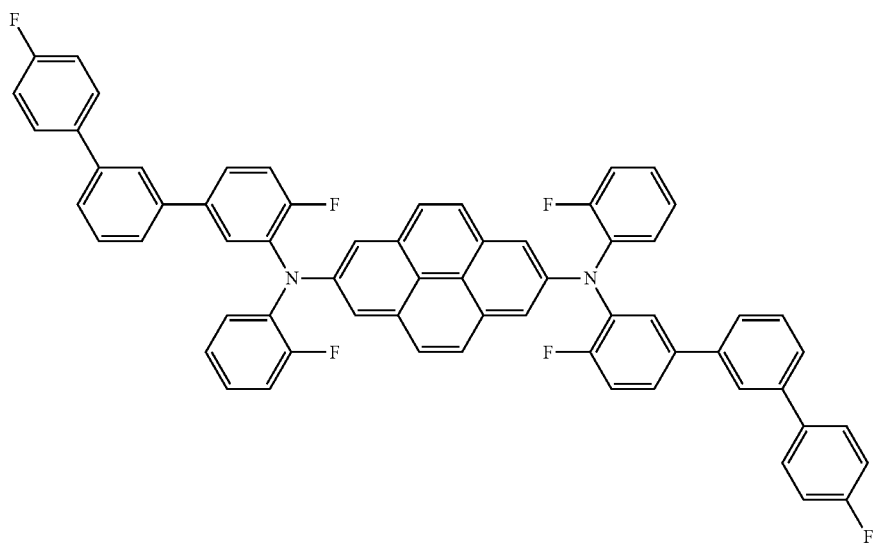

48

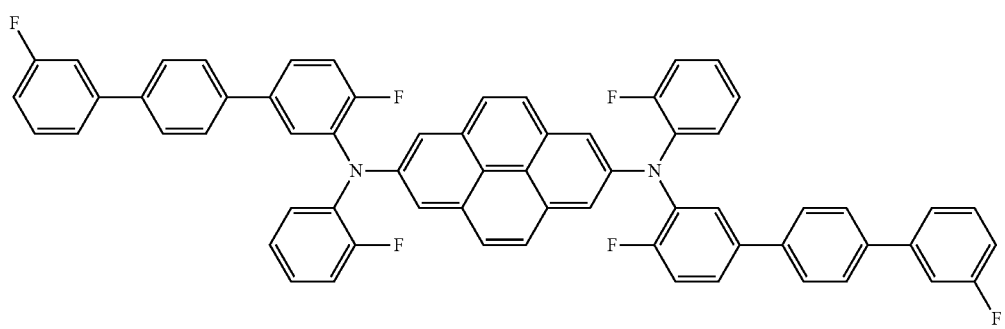

49

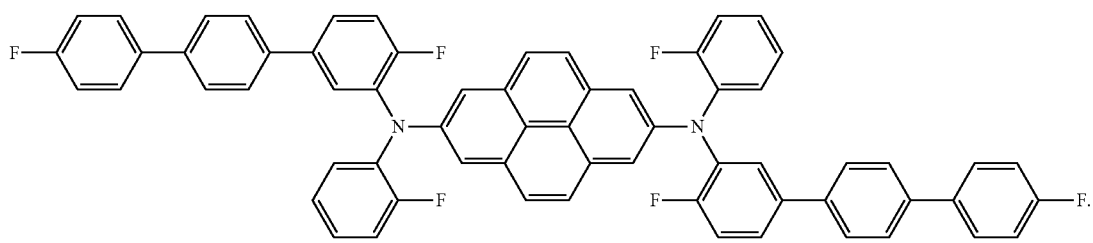

50

15. An organic light-emitting diode (OLED) comprising:
a first electrode;
a second electrode opposite the first electrode; and
an organic layer between the first electrode and the second electrode,
wherein the organic layer comprises at least one of the pyrene-based compound of claim 1.

16. The OLED of claim 15, wherein the organic layer comprises at least one of a hole injection layer (HIL), a hole transport layer (HTL), a functional layer having hole injection and hole transport abilities, a buffer layer, an electron blocking layer (EBL), an emission layer (EML), a hole blocking layer (HBL), an electron transport layer (ETL), an electron injection layer (EIL), and a functional layer having electron transport and electron injection abilities.

17. The OLED of claim 16, wherein the organic layer comprises an EML, and the EML comprises the pyrene-based compound.

18. The OLED of claim 17, wherein the pyrene-based compound in the EML is a dopant, and the EML further comprises a host.

19. The OLED of claim 18, wherein the host comprises at least one anthracene-based compound represented by Formulae 400 and 401:

Formula 400

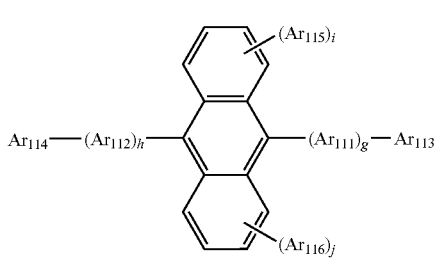

-continued

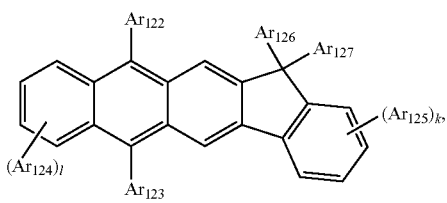

Formula 401 wherein each of $Ar_{111}$ and $Ar_{112}$ is independently a substituted or unsubstituted $C_6$-$C_{60}$ arylene group; each of $Ar_{113}$ to $Ar_{116}$ and $Ar_{122}$ to $Ar_{125}$ is independently a substituted or unsubstituted $C_1$-$C_{10}$ alkyl group or a substituted or unsubstituted $C_6$-$C_{60}$ aryl group; each of $Ar_{126}$ to $Ar_{127}$ is independently a $C_1$-$C_{10}$ alkyl group; and each of g, h, i, j, k and l is independently an integer of 0 to 4.

20. An organic light-emitting apparatus, comprising:
a substrate comprising first subpixels, second subpixels, and third subpixels;
a plurality of first electrodes comprising a first electrode for the first subpixels, a first electrode for the second subpixels, and a first electrode for the third subpixels;
a second electrode opposite the first electrode, the second electrode being a common electrode disposed commonly on the first, second, and third subpixels;
a first EML between the second electrode and the first electrode of the first subpixels, wherein the first EML is configured to emit light of a first color;
a second EML between the second electrode and the first electrode of the second subpixels, wherein the second EML is configured to emit light of a second color; and
a third EML between the second electrode and the first electrode of the third subpixels, wherein the third EML is configured to emit light of a third color,
wherein the first EML comprises the compound of claim 1, wherein the first electrodes are transparent electrodes or semitransparent electrodes, and the second electrode is a reflective electrode, or the first electrodes are reflective electrodes, and the second electrode is a transparent electrode or a semitransparent electrode;
wherein light from a mixture of the light of the first color, the light of the second color, and the light of the third color is white light, and the light of the first color is blue light.

* * * * *